(12) United States Patent
Popovitz

(10) Patent No.: US 11,938,029 B2
(45) Date of Patent: Mar. 26, 2024

(54) CIRCULATION REPLENISHING JOINT IMPLANT

(71) Applicant: Leon E. Popovitz, New York, NY (US)

(72) Inventor: Leon E. Popovitz, New York, NY (US)

( * ) Notice: Subject to any disclaimer, the term of this patent is extended or adjusted under 35 U.S.C. 154(b) by 0 days.

(21) Appl. No.: 15/963,981

(22) Filed: Apr. 26, 2018

(65) Prior Publication Data

US 2018/0243095 A1   Aug. 30, 2018

Related U.S. Application Data

(63) Continuation of application No. PCT/US2016/058932, filed on Oct. 26, 2016.
(Continued)

(51) Int. Cl.
*A61F 2/30* (2006.01)
*A61B 17/04* (2006.01)
(Continued)

(52) U.S. Cl.
CPC ................ *A61F 2/30* (2013.01); *A61B 17/04* (2013.01); *A61B 17/0401* (2013.01); *A61B 17/0642* (2013.01); *A61F 2/0811* (2013.01); *A61F 2/30749* (2013.01); *A61F 2/30756* (2013.01); *A61F 2/4603* (2013.01); *A61B 2017/0412* (2013.01); *A61B 2017/0414* (2013.01); *A61B 2017/0427* (2013.01); *A61B 2017/0646* (2013.01); *A61B 2017/0647* (2013.01); *A61B 2017/0648* (2013.01); *A61B 2217/007* (2013.01); *A61F 2002/0841* (2013.01); *A61F 2002/0858* (2013.01); *A61F 2002/0888* (2013.01); *A61F 2002/0894* (2013.01);
(Continued)

(58) Field of Classification Search
CPC . A61B 17/04; A61B 17/0485; A61B 17/0401; A61B 17/0642; A61B 2017/0646; A61F 2/0811
See application file for complete search history.

(56) References Cited

U.S. PATENT DOCUMENTS 4,988,351 A   1/1991   Paulos et al.
5,413,585 A   5/1995   Pagedas
(Continued)

FOREIGN PATENT DOCUMENTS

EP   0595782 A2   5/1994
RU   2111718 C1   5/1998

OTHER PUBLICATIONS

EP Application No. 16860720.8, EP Search Report dated Jul. 2, 2019, consists of 7 pages.
(Continued)

*Primary Examiner* — Marcia L Watkins

(57) ABSTRACT

A joint implant device is presented. In embodiments, the device may include a central cylindrical anchor with a sharp distal end and a substantially flat proximal portion. In embodiments, the anchor may be provided with at least one longitudinally extending microtube, to convey at least one of blood and nutrients from the distal end to a proximal end. In embodiments, there may be a plurality of microtubes, each having an intake in the distal end and multiple outflows in the proximal portion. In some embodiments the device may include an eyelet through which a suture may be provided for additional fixation into a joint.

19 Claims, 94 Drawing Sheets

Related U.S. Application Data

(60) Provisional application No. 62/246,218, filed on Oct. 26, 2015.

(51) Int. Cl.
    *A61B 17/064*     (2006.01)
    *A61F 2/08*     (2006.01)
    *A61F 2/46*     (2006.01)

(52) U.S. Cl.
    CPC .............. *A61F 2002/30593* (2013.01); *A61F 2002/30691* (2013.01); *A61F 2002/30751* (2013.01)

(56) References Cited

U.S. PATENT DOCUMENTS

| | | | |
|---|---|---|---|
| 5,725,581 A | | 3/1998 | Br.ang.nemark |
| 5,743,912 A | * | 4/1998 | Lahille ................ A61B 17/742 606/65 |
| 6,210,376 B1 | * | 4/2001 | Grayson .............. A61B 17/864 606/304 |
| 8,070,785 B2 | | 12/2011 | Biscup |
| 8,545,535 B2 | | 10/2013 | Hirotsuka et al. |
| 9,943,340 B2 | * | 4/2018 | Whipple .............. A61B 17/864 |
| 2002/0042615 A1 | | 4/2002 | Graf et al. |
| 2004/0034375 A1 | | 2/2004 | Ruiz et al. |
| 2004/0225292 A1 | | 11/2004 | Sasso et al. |
| 2005/0222619 A1 | * | 10/2005 | Dreyfuss ............ A61B 17/0401 606/232 |
| 2006/0100630 A1 | | 5/2006 | West, Jr. |
| 2007/0233123 A1 | * | 10/2007 | Ahmad ................ A61B 17/864 606/307 |
| 2007/0233151 A1 | | 10/2007 | Chudik |
| 2009/0192546 A1 | | 7/2009 | Schmieding et al. |
| 2009/0318981 A1 | * | 12/2009 | Kang .................. A61B 17/864 606/62 |
| 2010/0042213 A1 | * | 2/2010 | Nebosky ................ A61B 17/56 623/16.11 |
| 2010/0042214 A1 | * | 2/2010 | Nebosky ............ A61B 17/8625 623/16.11 |
| 2010/0106199 A1 | | 4/2010 | Sawa et al. |
| 2010/0145386 A1 | * | 6/2010 | Greenhalgh ....... A61B 17/7059 606/246 |
| 2010/0211113 A1 | * | 8/2010 | Olson ................ A61B 17/8625 606/301 |
| 2010/0262184 A1 | * | 10/2010 | Dreyfuss ............ A61B 17/0401 606/228 |
| 2010/0292732 A1 | | 11/2010 | Hirotsuka et al. |
| 2011/0004258 A1 | | 1/2011 | Stone et al. |
| 2011/0054612 A1 | | 3/2011 | Dehnad et al. |
| 2011/0060373 A1 | * | 3/2011 | Russell .............. A61B 17/0401 606/304 |
| 2012/0197296 A1 | * | 8/2012 | Mayer ................ A61B 17/0401 606/232 |
| 2013/0197578 A1 | | 8/2013 | Gregoire et al. |
| 2013/0218214 A1 | | 8/2013 | Beyar et al. |
| 2013/0253594 A1 | | 9/2013 | Zucherman et al. |
| 2013/0267998 A1 | | 10/2013 | Vijay et al. |
| 2015/0164498 A1 | | 6/2015 | Dreyfuss et al. |
| 2016/0367371 A1 | * | 12/2016 | de Beaubien ....... A61F 2/30907 |

OTHER PUBLICATIONS

International Search Report and Written Opinion dated Jan. 30, 2017 for International Application No. PCT/US2016/058932, 11 pages.

International Preliminary Report on Patentability dated May 11, 2018 for International Application No. PCT/US2016/058932, 13 pages.

RU Application No. 2018118027, RU Search Report dated Sep. 14, 2020, consists of 2 pages.

RU Application 2018118027, Office Action dated Sep. 21, 2020 consists of 5 pages, English Transalation attached.

\* cited by examiner

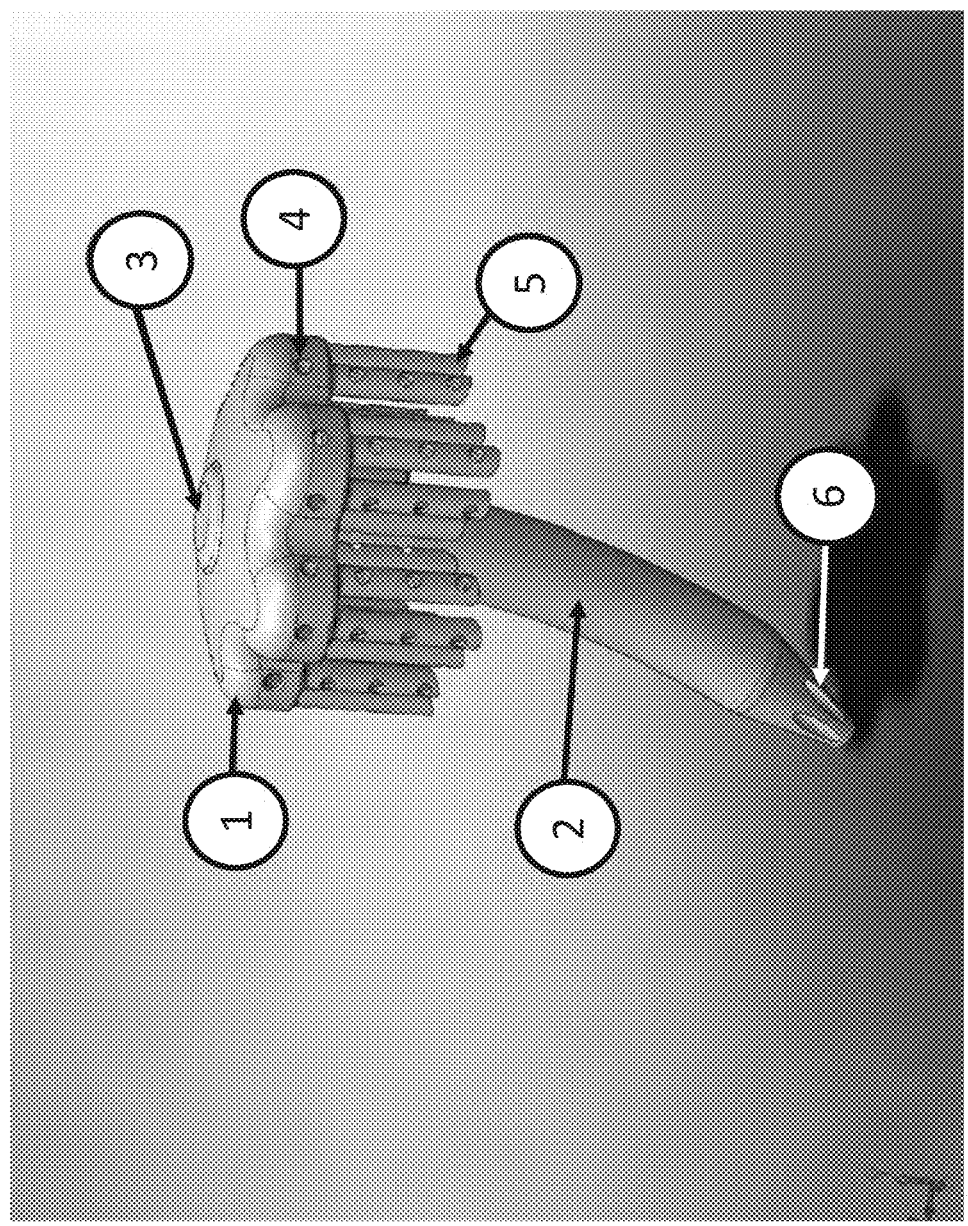
FIG. 12

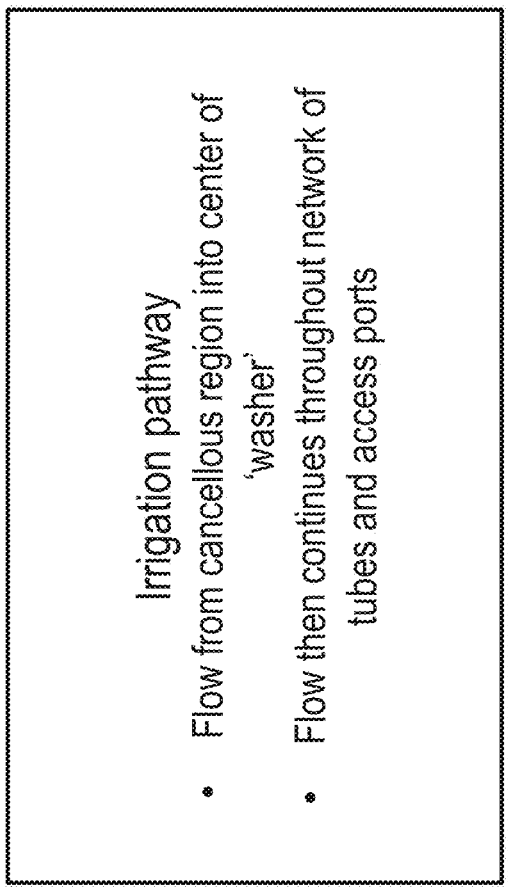
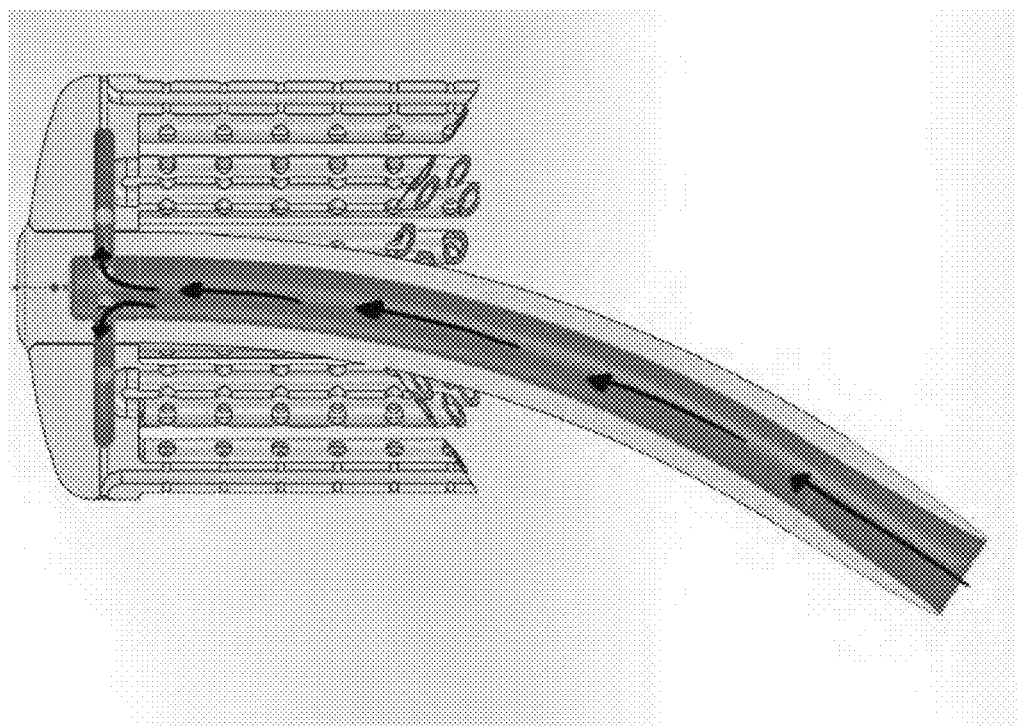
FIG. 17

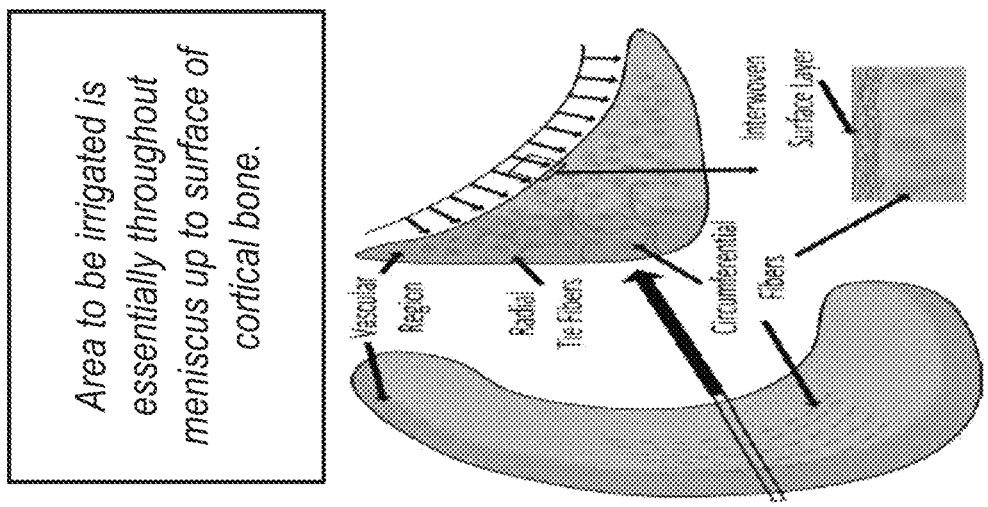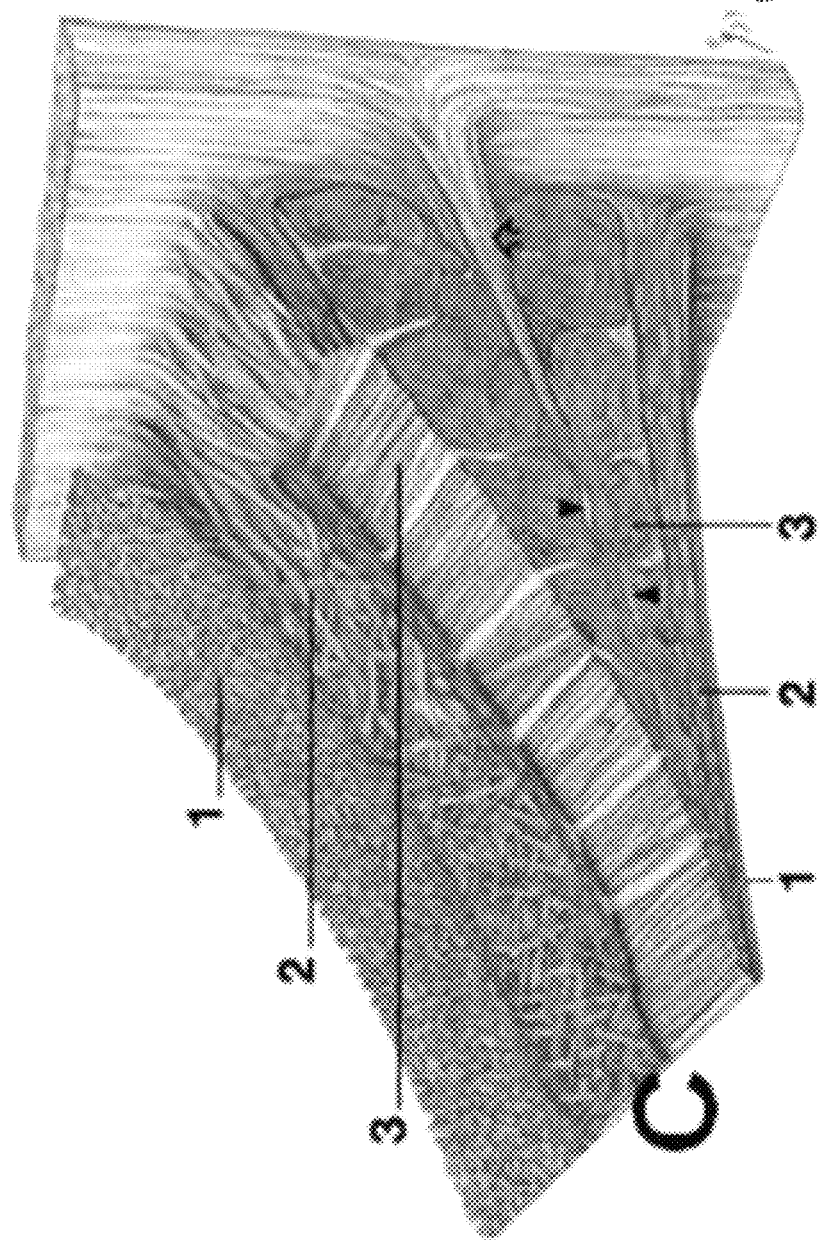
FIG. 19
Cut away of meniscus showing various bundle components: 1) superficial bundle network; 2) tie fibers; and 3) circumferentially oriented fiber bundles.

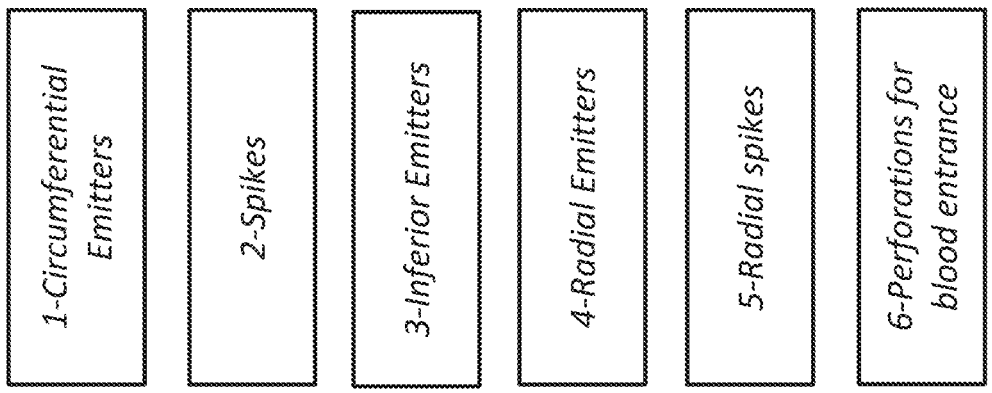
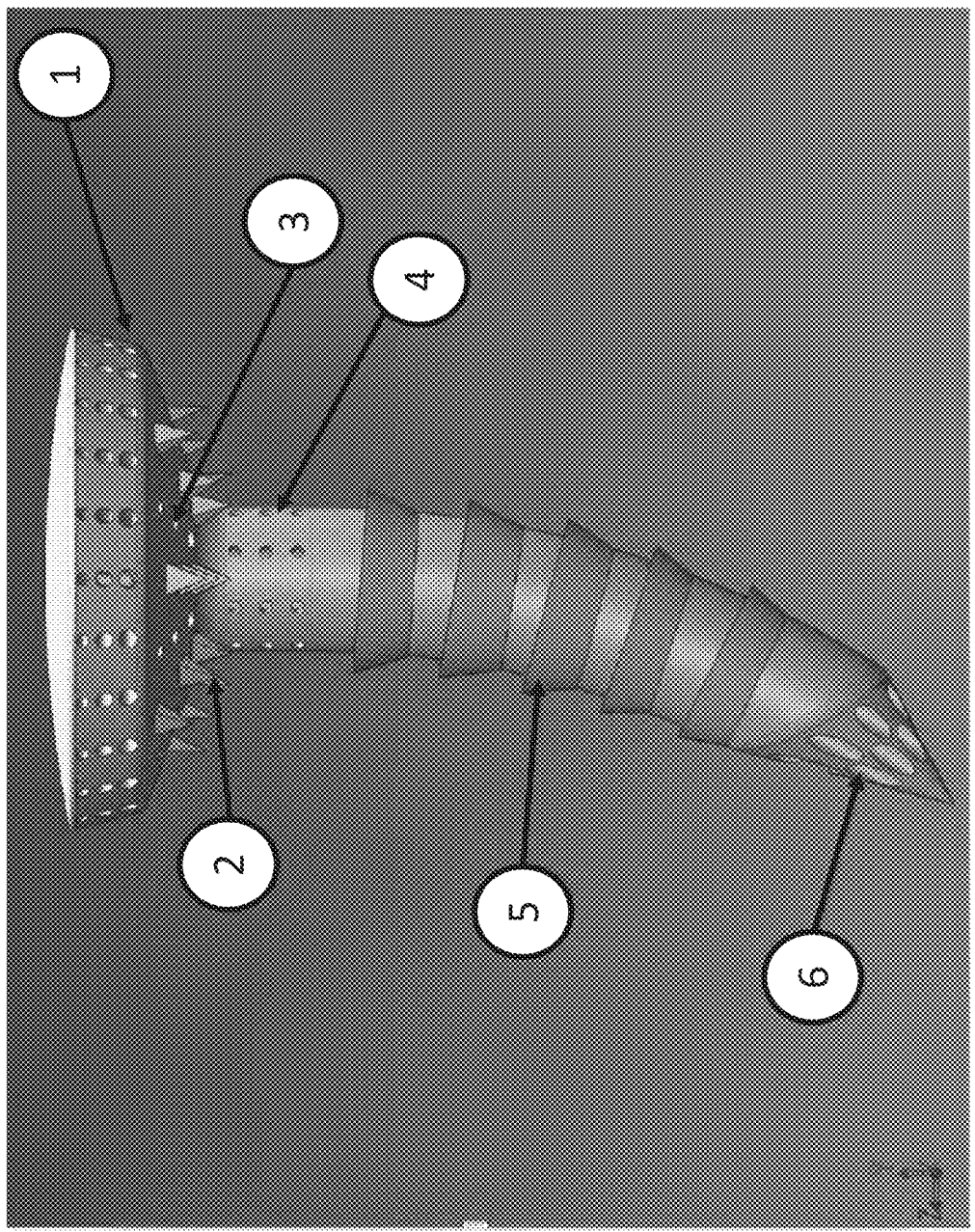
FIG. 22

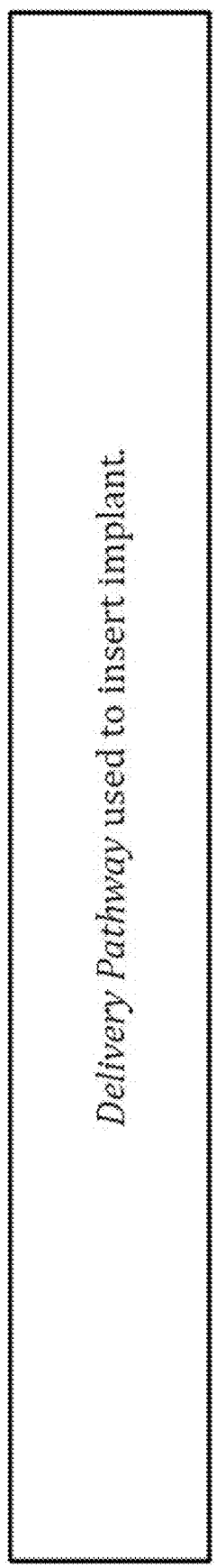
*Delivery Pathway used to insert implant.*
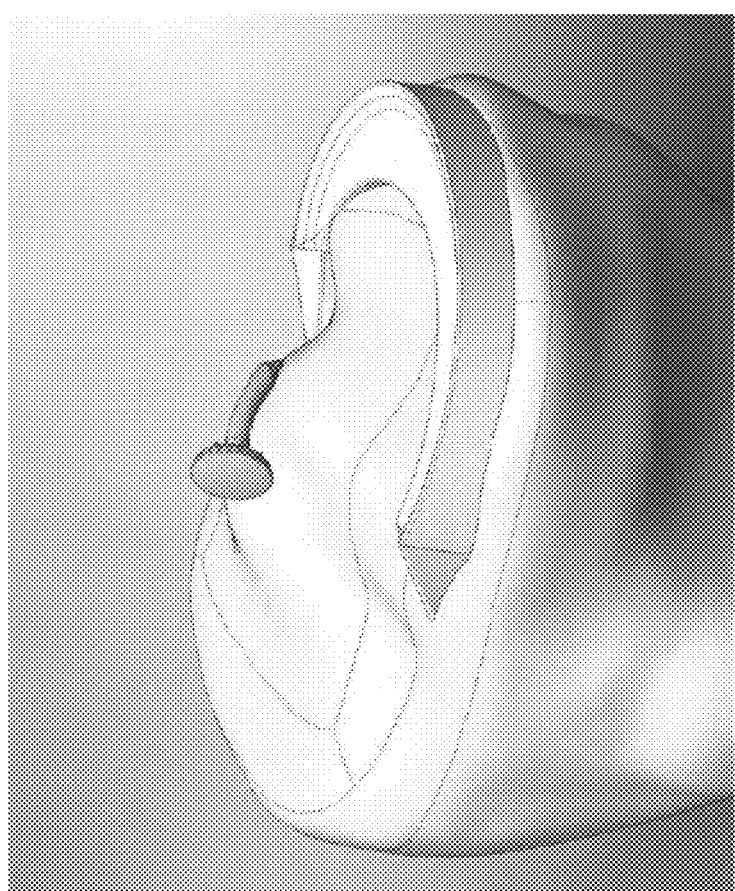
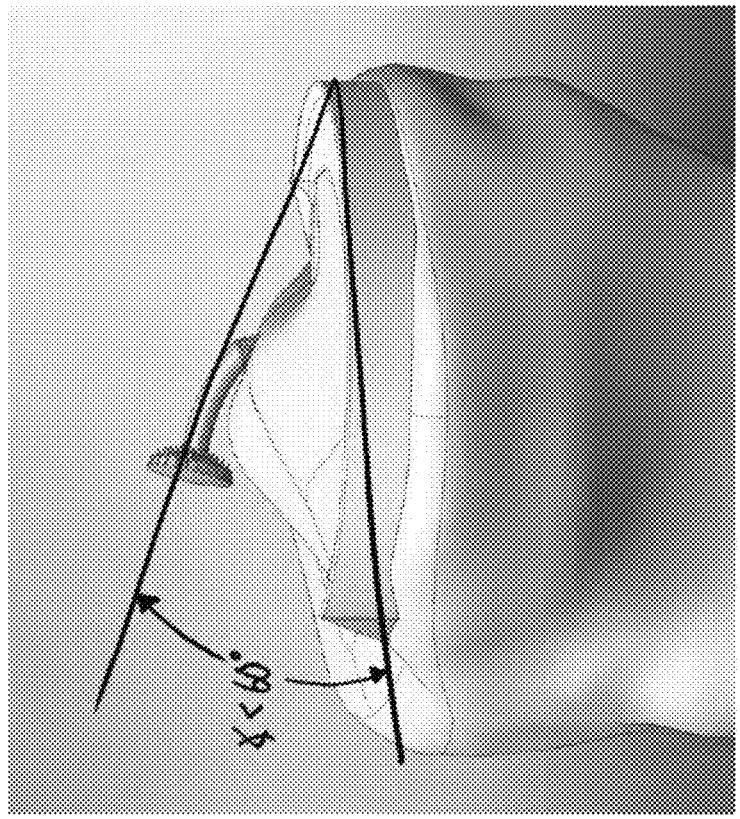
FIG. 26

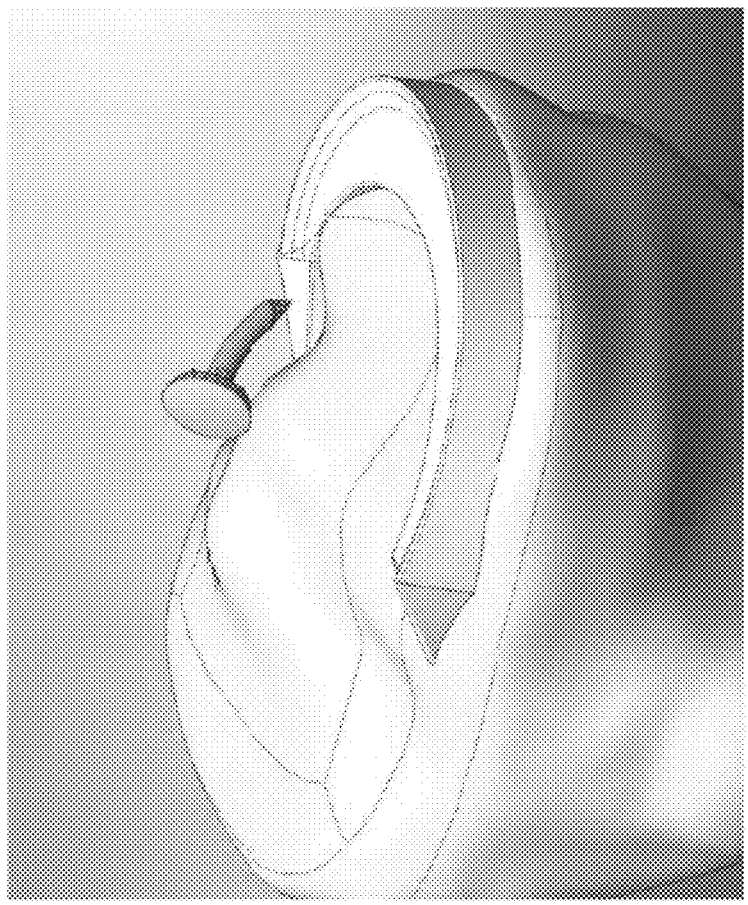
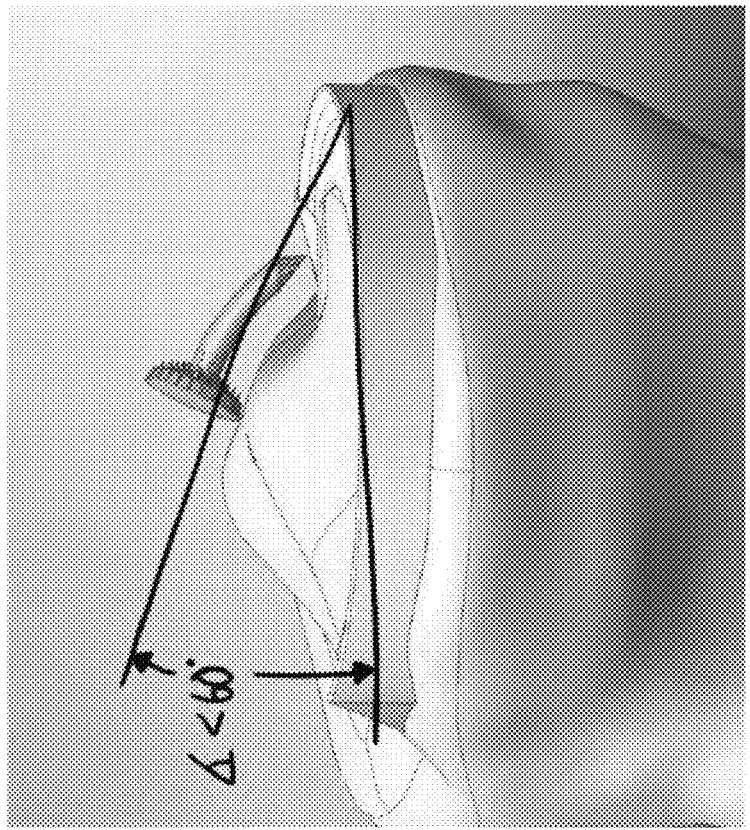
*Delivery Pathway used to insert implant.*
FIG. 27

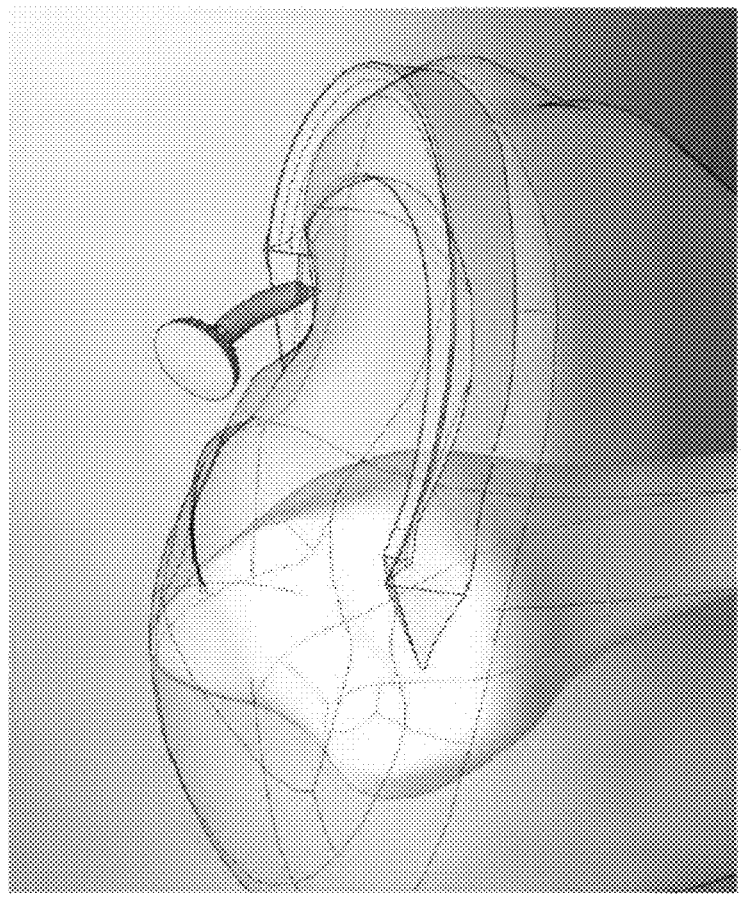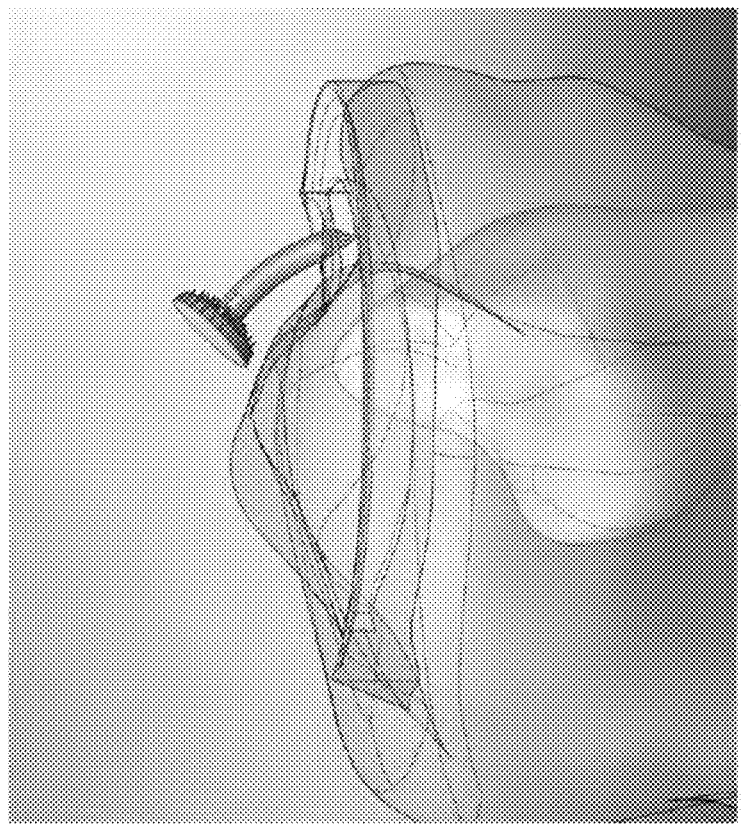
*Delivery Pathway used to insert implant.*
FIG. 28

*Delivery Pathway used to insert implant.*
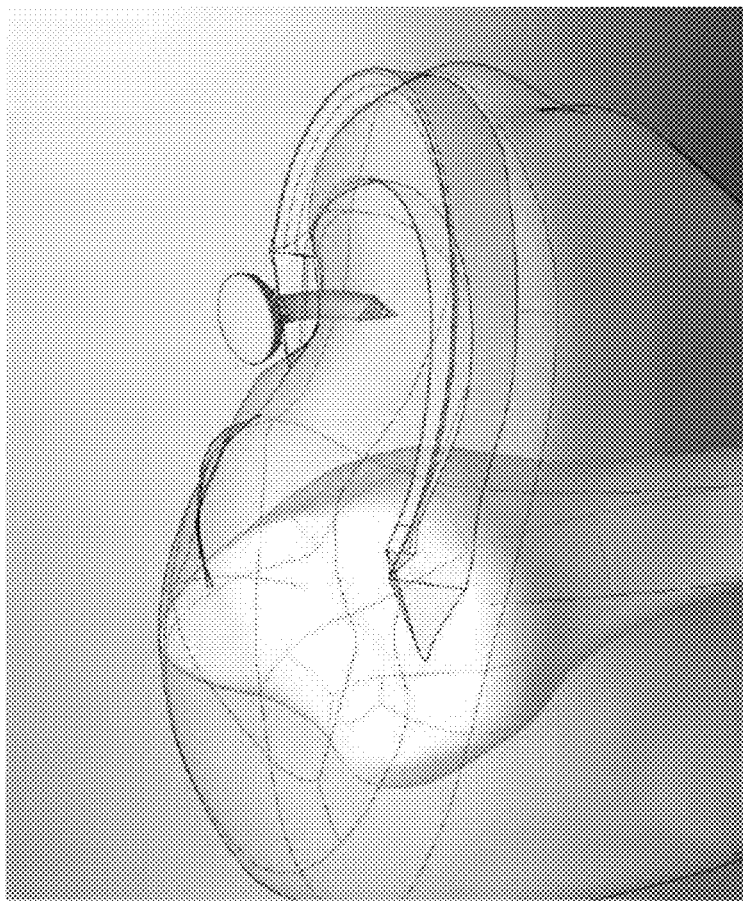
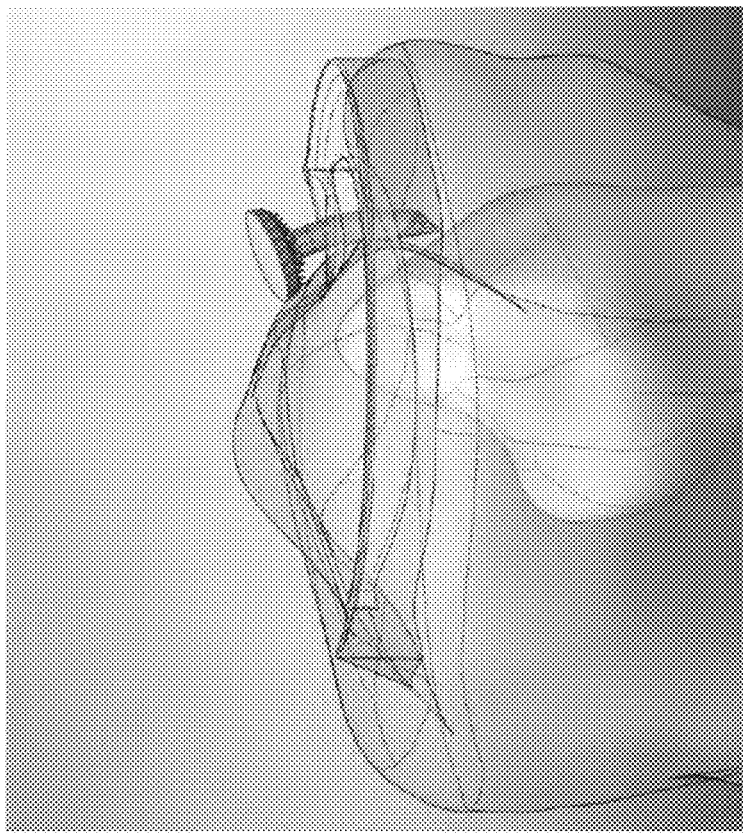
FIG. 29

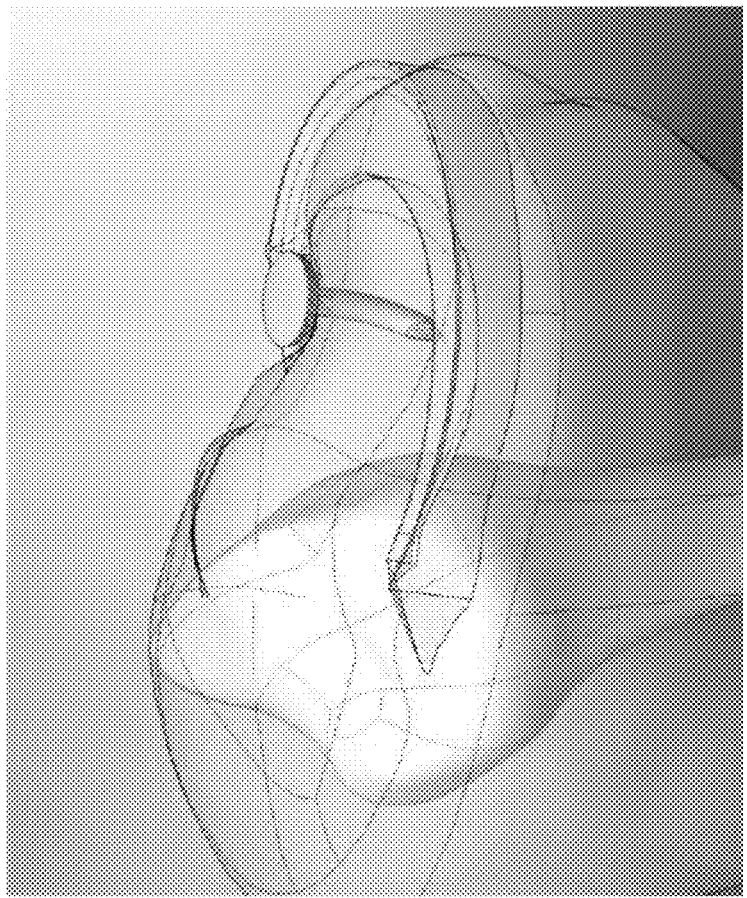
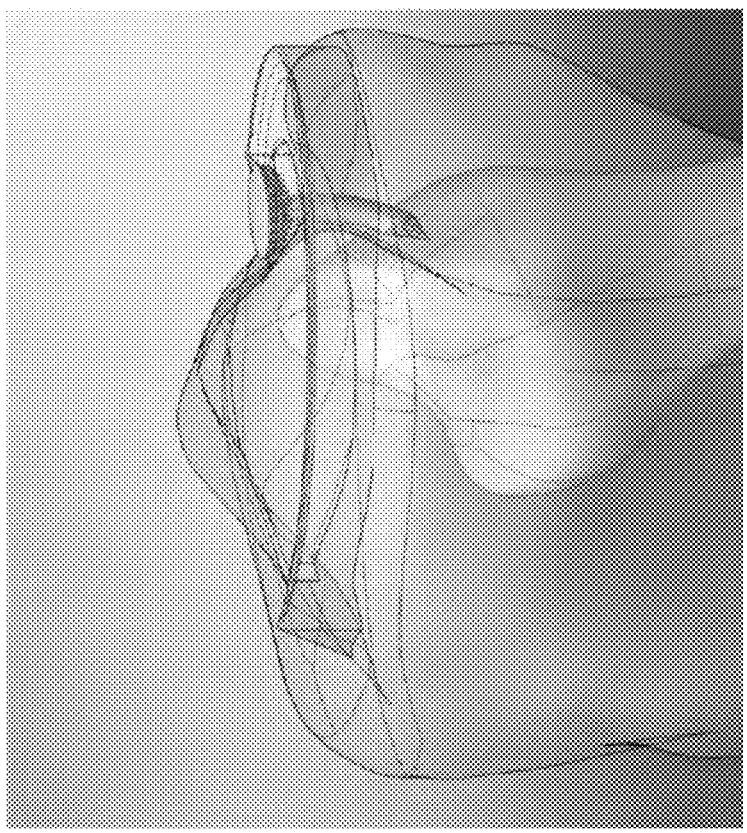
*Delivery Pathway used to insert implant.*
FIG. 30

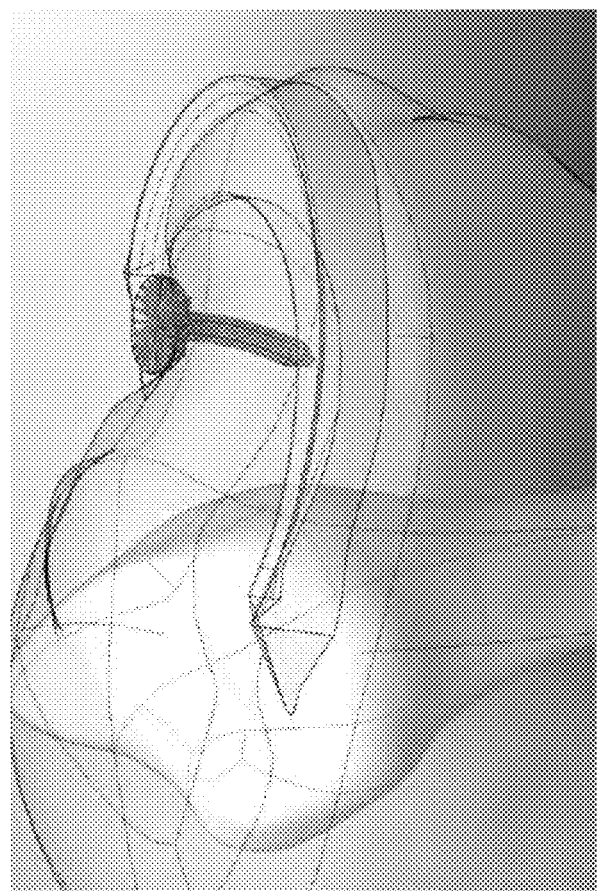
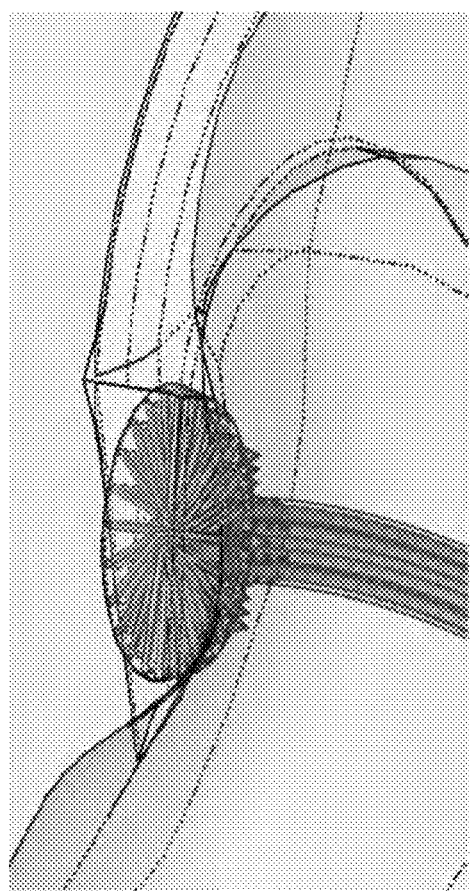
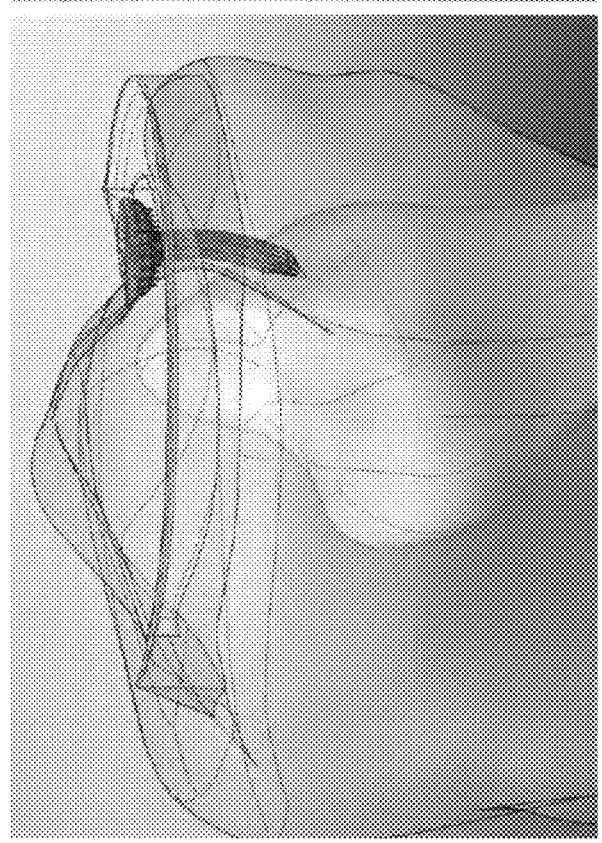
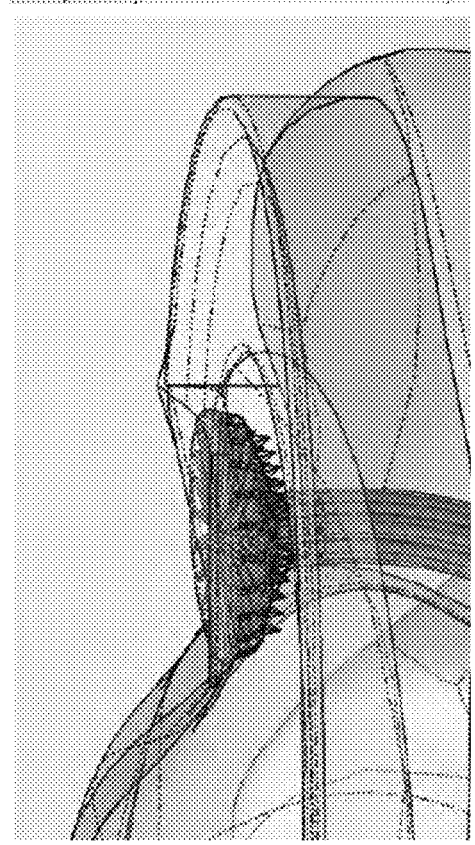
FIG. 31

Estimate Channel Size
- Ø .30mm (est)
Benefits
- Low cost at volume
Challenges
- Channel diameter
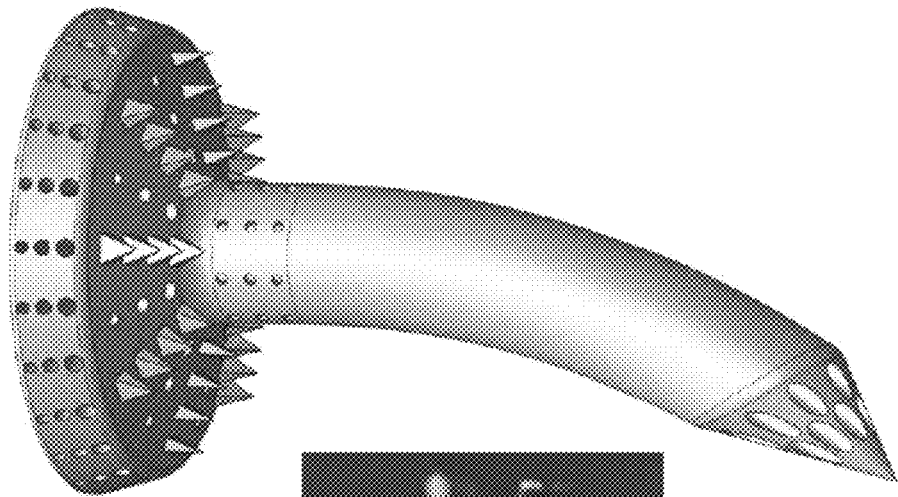
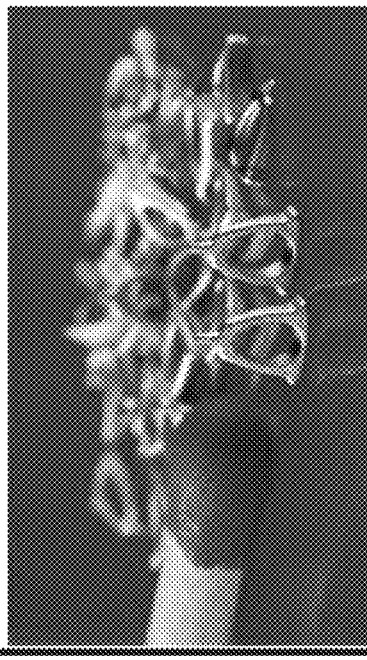
FIG. 39

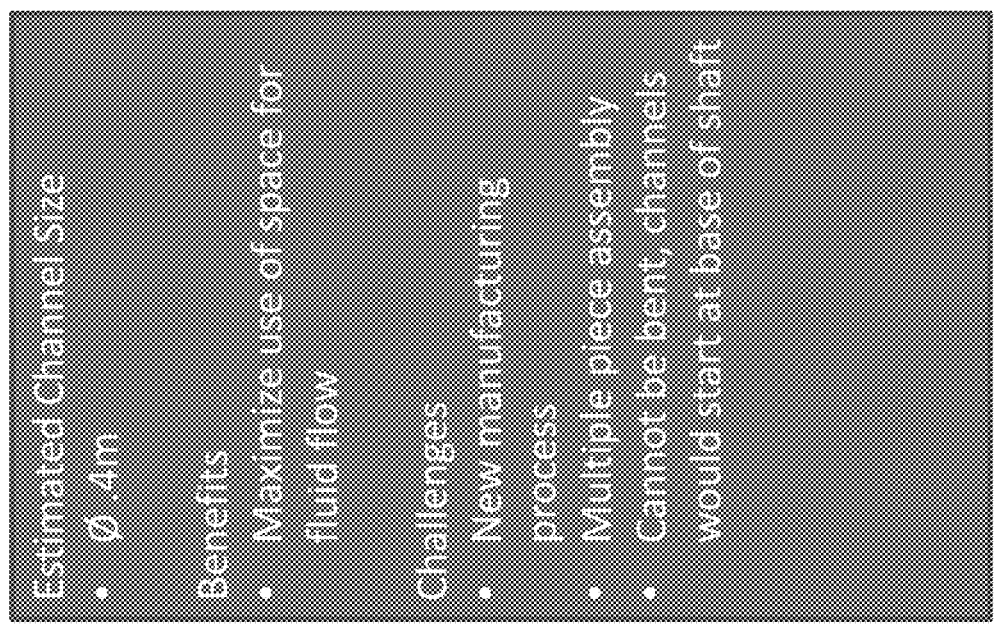
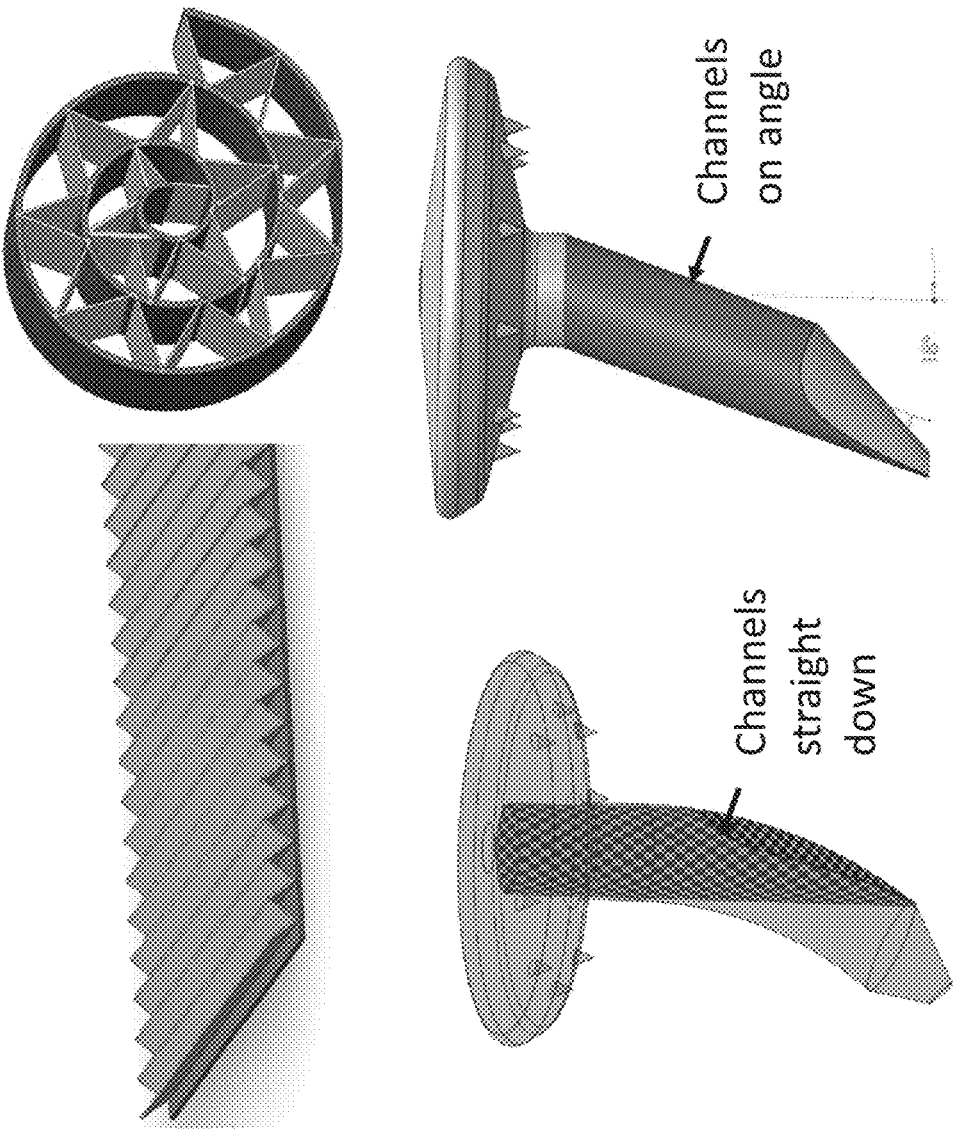
FIG. 45

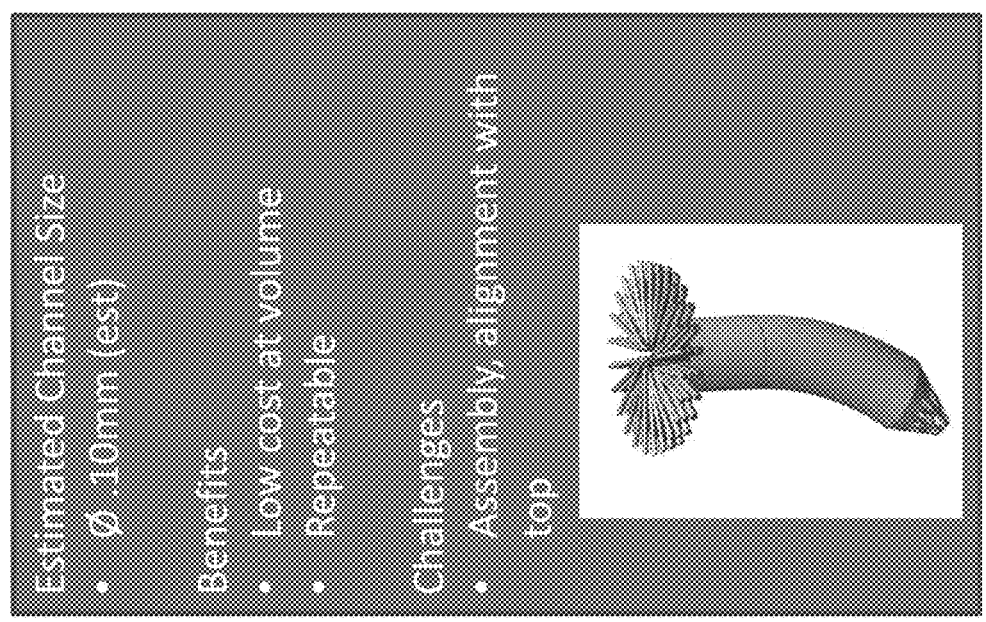
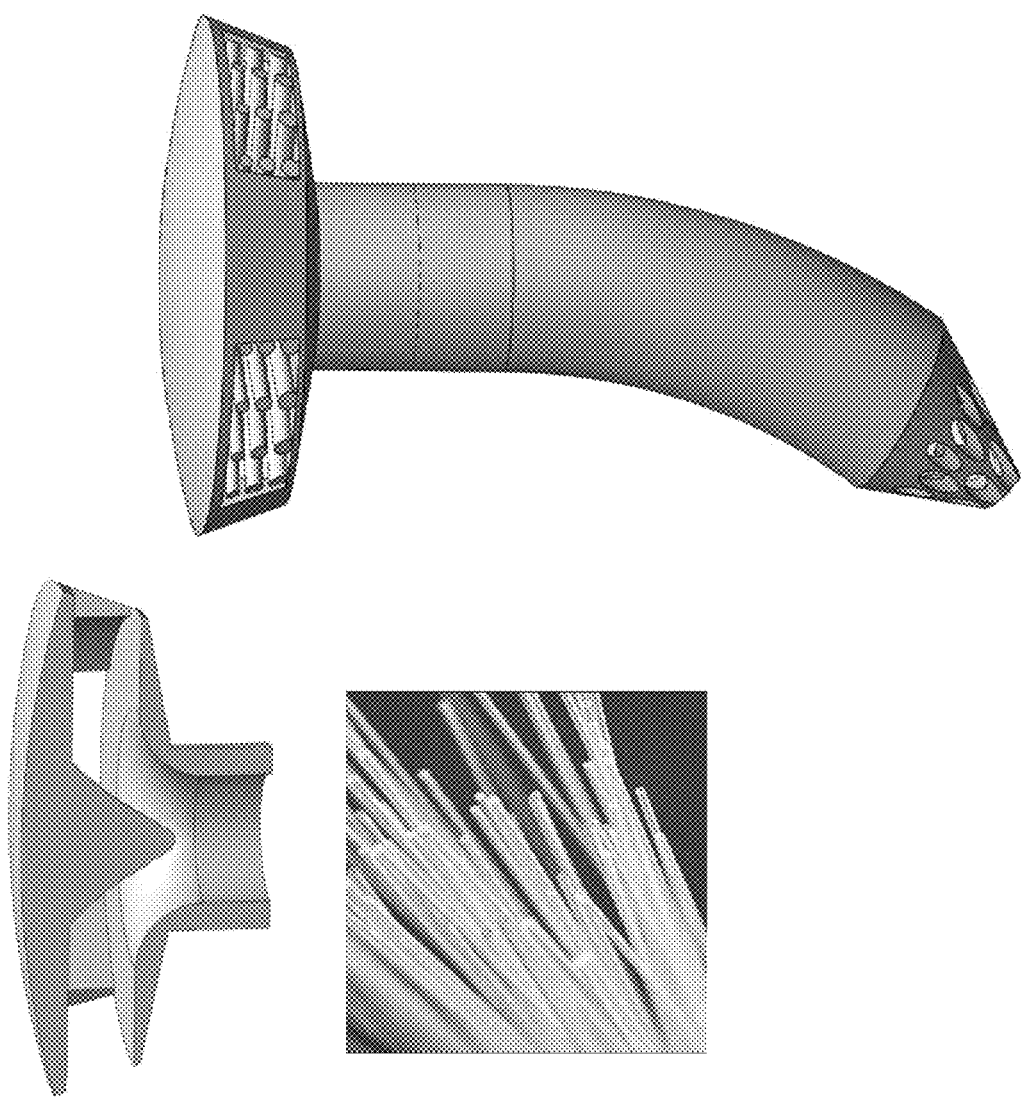
FIG. 47

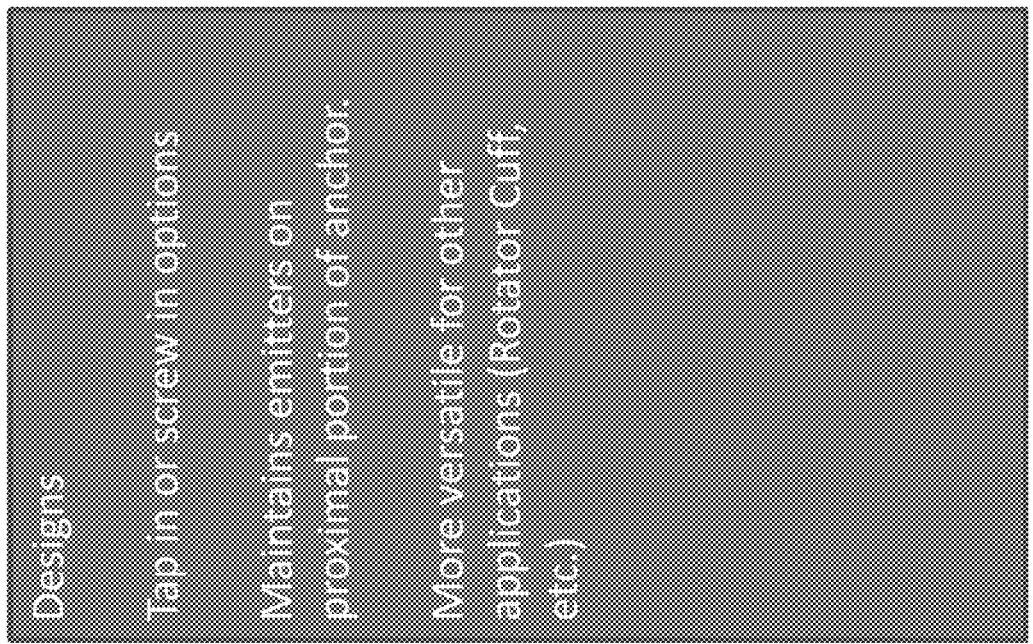
FIG. 57
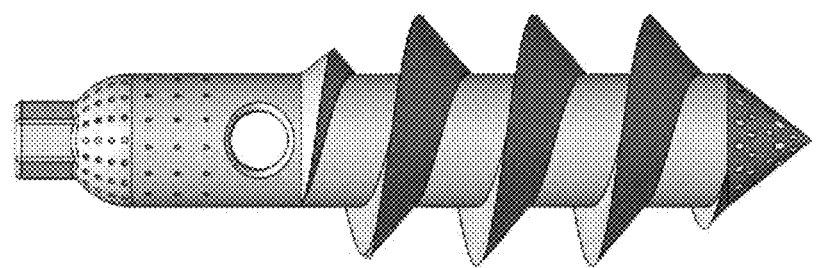
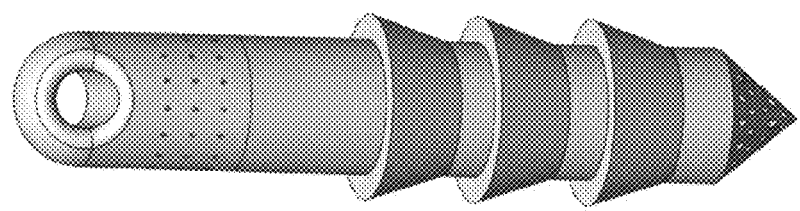

Optimizing Channel Sizes and Quantity

| mm | # | mm^2 | Flow rate (r^4) | # Emmiters per Blade Channel (Flow rate equation) | # Emmitters (@.050mm) | Total Emitter flow mm^2 |
|---|---|---|---|---|---|---|
| Channel size | CSA channels | Total Blade flow CSA | $Q = \frac{\Delta P \pi r^4}{8 \eta l}$ | | | |
| 0.05 | 220 | 0.432 | 0.0013750000 | 1.000 | 220 | 172.7 |
| 0.1 | 120 | 0.942 | 0.0220000000 | 16.000 | 1920 | 1507.2 |
| 0.15 | 80 | 1.413 | 0.1113750000 | 81.000 | 6480 | 5086.8 |

Configurations Data

| Feature | A | B | C | D | E |
|---|---|---|---|---|---|
| 1mm straight channels penetrating eyehole | X |   |   | X | X |
| 1mm around eyelet |   |   | X |   |   |
| .8mm side shafts | X | X |   |   |   |
| Driver feature | X | X | X | X | X |
| Proximal Emitters |   | X | X | X | X |

FIG. 66

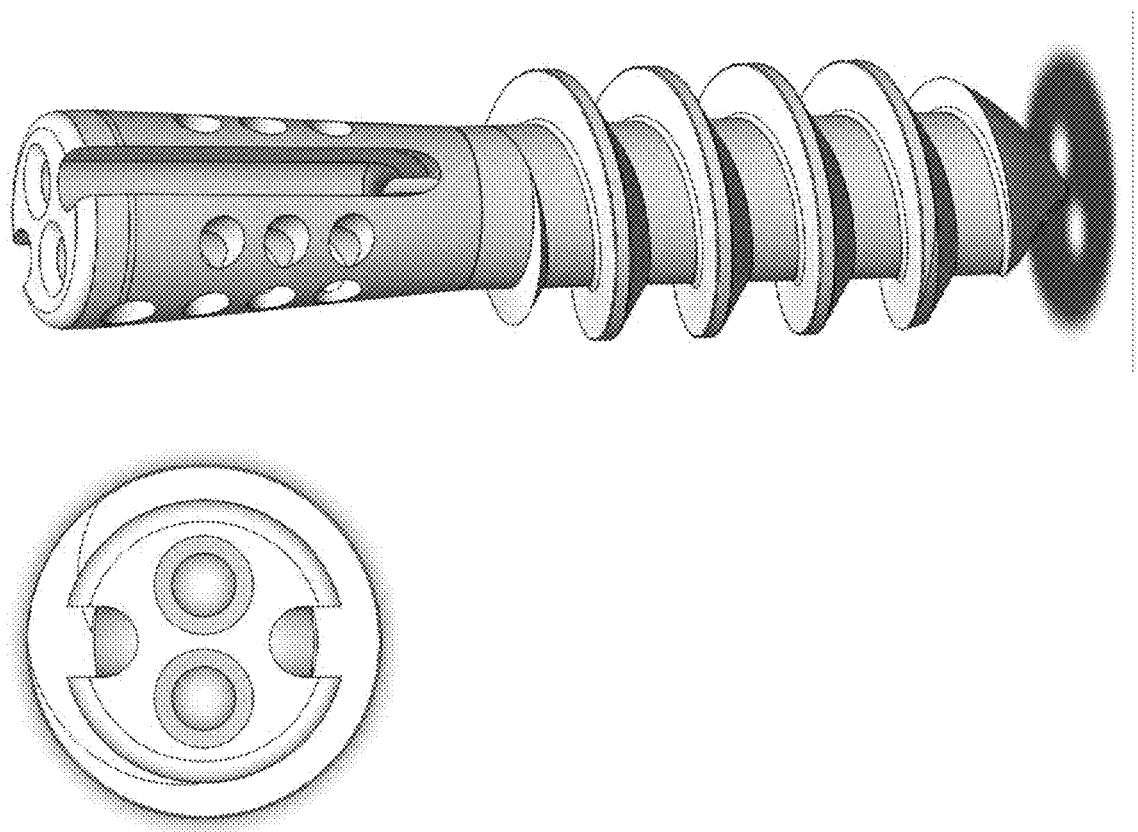
Concept E
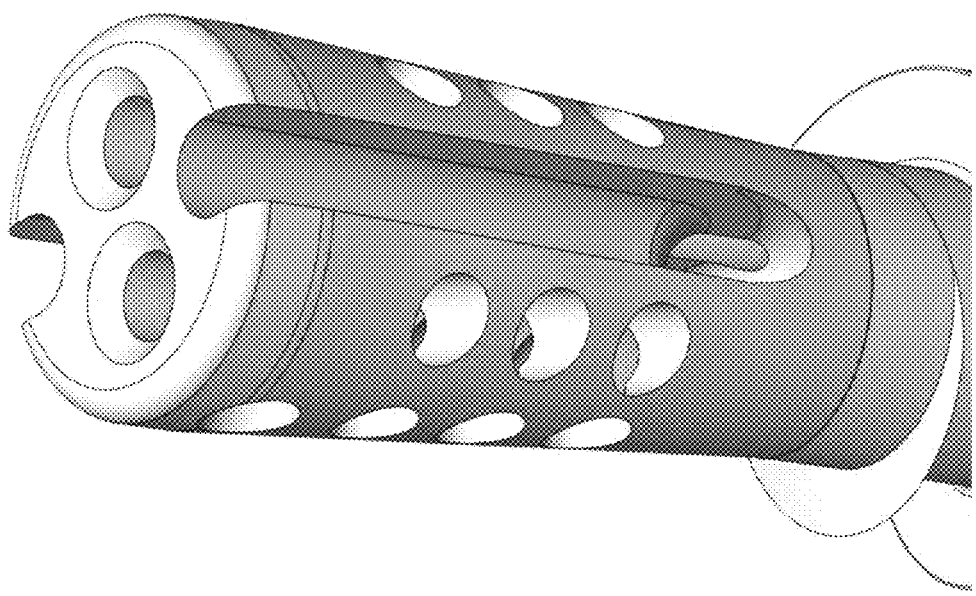
FIG. 69

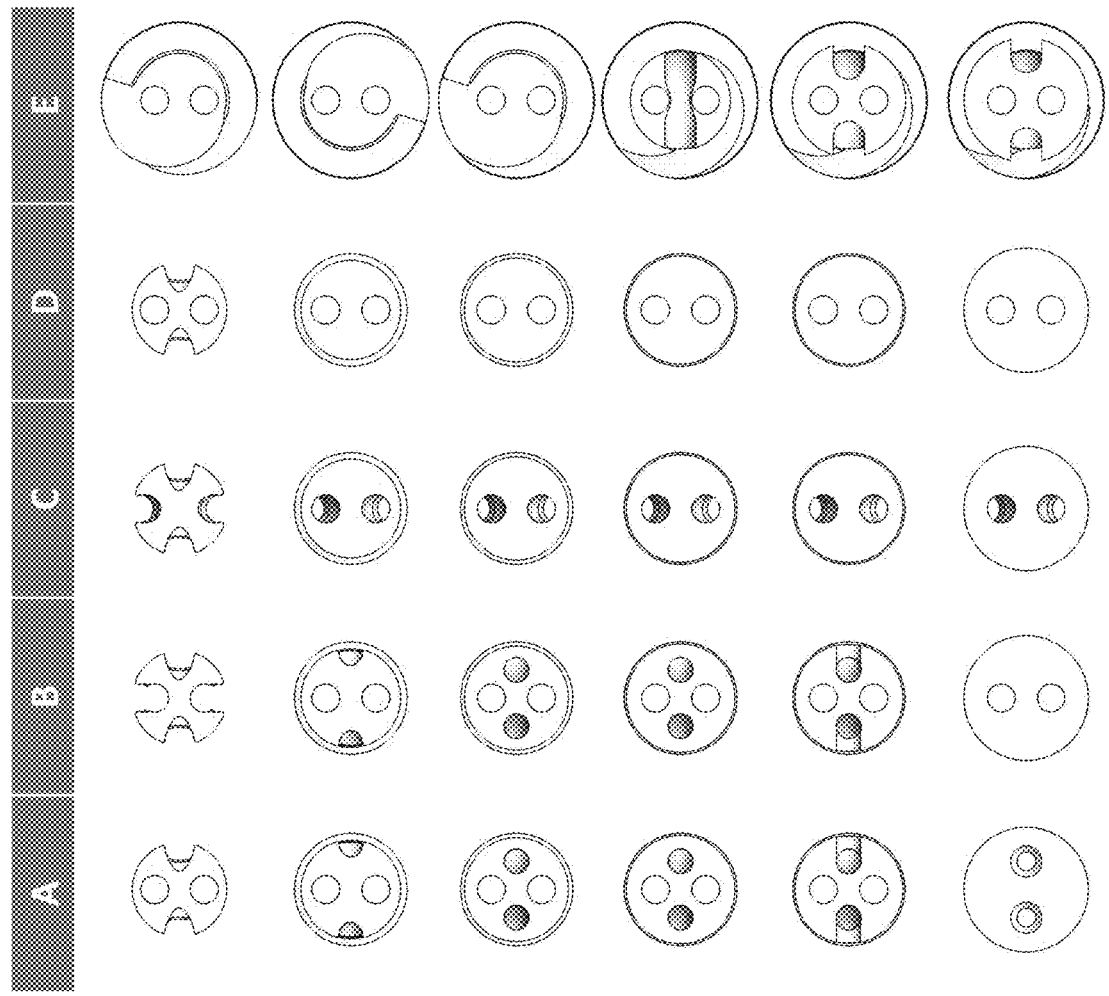
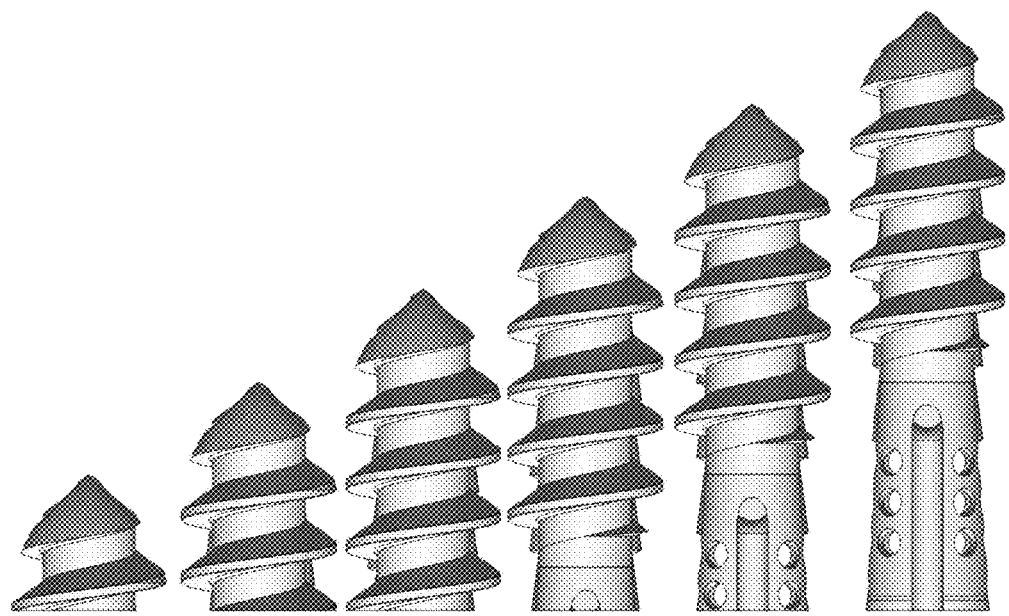
FIG. 75

FIG. 88

| Joint Feature | BLOKS (49) Interreader (weighted κ)* | KOSS (30) Interreader (ICC: weighted κ) | KOSS (30) Intrareader (ICC: weighted κ) | WORMS (31) Interreader Agreement (ICC) |
|---|---|---|---|---|
| Cartilage morphology | 0.72 (0.59, 0.85) | 0.64 (0.58, 0.69), 0.57 | 0.78 (0.74, 0.81), 0.67 | 0.89 |
| Cartilage 2 (BLOKS only) | 0.73 (0.60, 0.85) | Not applicable | Not applicable | Not applicable |
| Osteochondral defects (KOSS only) | Not applicable | 0.63 (0.55, 0.70), 0.66 | 0.87 (0.83, 0.90), 0.87 | Not applicable |
| Bone marrow lesion size | 0.72 (0.58, 0.87) | 0.91 (0.88, 0.93), 0.88 | 0.93 (0.91, 0.94), 0.91 | 0.74 |
| Bone marrow lesion percentage area (BLOKS only) | 0.69 (0.55, 0.82) | Not applicable | Not applicable | Not applicable |
| Percentage of lesion bone marrow lesion (BLOKS only) | 0.72 (0.58, 0.87) | Not applicable | Not applicable | Not applicable |
| Osteophytes | 0.65 (0.52, 0.77) | 0.77 (0.67, 0.76), 0.67 | 0.76 (0.72, 0.80), 0.79 | 0.97 |
| Synovitis | 0.62 (0.05, 1.00) | 0.74 (0.58, 0.85), 0.69 | 0.81 (0.69, 0.89), 0.77 | 0.74 |
| Effusion | 0.61 (0.06, 0.85) | Scores combined† | Scores combined† | Scores combined† |
| Meniscal extrusion or subluxation | 0.51 (0.24, 0.78) | 0.67 (0.57, 0.75), 0.65 | 0.82 (0.75, 0.86), 0.82 | Not applicable |
| Meniscal signal intensity and/or intrasubstance degeneration | 0.68 (0.44, 0.93) | 0.78 (0.68, 0.86), 0.66 | 0.76 (0.66, 0.83), 0.56 | Not applicable |
| Meniscal tear | 0.79 (0.40, 1.00) | 0.70 (0.61, 0.77), 0.70 | 0.78 (0.70, 0.83), 0.78 | 0.87 |
| Ligaments | Not applicable | Not applicable | Not applicable | 1.0 |
| Subchondral cysts | Part of bone marrow lesion percentage score | 0.87 (0.83, 0.89), 0.83 | 0.90 (0.87, 0.92), 0.87 | 0.94 |
| Baker cysts | Not applicable | 0.89 (0.76, 0.95), 0.80 | 0.96 (0.90, 0.98), 0.91 | Not applicable |

CIRCULATION REPLENISHING JOINT IMPLANT

CROSS-REFERENCE TO RELATED APPLICATIONS

This application is a continuation of PCT/US2016/058932, filed on Oct. 26, 2016, which published as WO 2017/075095, and is titled "CIRCULATION REPLENISHING JOINT IMPLANT", the entire disclosure of which is hereby incorporated herein by this reference. This application also claims the benefit of, and priority to, U.S. Provisional Patent Application No. 62/246,218, filed on Oct. 26, 2015, the entire disclosure of which is hereby incorporated herein by this reference.

TECHNICAL FIELD

The present disclosure is directed to medical devices, and in particular to a joint implant that provides both fixation and irrigation of the meniscal root to cure meniscal root tears, prevent meniscal root tears or degenerative meniscal tears, and prevent the progression or onset of osteoarthritis of the joint (degenerative disease) and rejuvenate the joint.

BACKGROUND OF THE INVENTION

The present disclosure addresses an injured or weak human meniscus. A weakened meniscus may lead to osteoarthritis (OA). While the following discussion focuses on the knee as an ongoing example, it is equally applicable to various other human joints.

It is well known that the primary cause of knee osteoarthritis (OA) is excessive biomechanical loading (1)[1]. Such overloading may include mal-alignment, previous trauma, obesity, or occupational hazards, combined with degeneration of the meniscal matrix (which is related to early OA), leading to meniscal fatigue, rupture and eventual extrusion (2). Once the meniscus loses its load distribution function, articular cartilage loss develops, leading to osteoarthritis (3).

[1] In this application, numbers in parentheses refer to the references provided at the end of the disclosure.

SUMMARY OF THE INVENTION

Joint implants, delivery systems, and associated insertion techniques are presented. In embodiments, these may be used, for example, to cure meniscal root tears, prevent meniscal root tears or degenerative meniscal tears, prevent the progression or onset of osteoarthritis of the joint (degenerative disease) and rejuvenate the joint. In embodiments, an implant may also be used to repair and cure rotator cuff tears, labral tears and any tears of soft tissue that require the blood form bone (to which it is fixed) for healing. A minimally invasive technique for (i) repairing the meniscal root that recreates the natural anatomy without requiring violating trans tibial drill holes, and that (ii) provides for recirculation of blood flow and nutritional healing elements into the meniscal root, using an implant device, are thus described. Exemplary implants may include an anchor and a washer, or an integrated tack device, or a suture anchor type implant, that each protrude into bone underneath a meniscal root attachment site. In accordance with various embodiments, implants may each contain microtubes to allow for blood and nutrients to flow from the bone interior into the meniscal root and meniscus. Thus, in embodiments, an implant may function as an "irrigation system" for the meniscus, which effectively revascularizes it, thereby allowing it to repair itself (heal). As such, in embodiments, implants and related techniques may slow down or even stop the progression of osteoarthritis in the knee by rejuvenation of the meniscal root and, subsequently, the meniscus itself. This may allow for maintaining the dissipation of hoop stresses and, as a result, may protect the articular cartilage and may prevent the development of osteoarthritis.

BRIEF DESCRIPTION OF THE DRAWINGS

FIGS. 12, 13, 13A, 13B and 13C respectively depict details and exemplary dimensions of the exemplary blade and washer of FIG. 6 according to an exemplary embodiment of the present invention;

FIG. 17 illustrates an alternate embodiment of exemplary irrigation canals and irrigation pathways within the blade and washer combination;

FIG. 19 depicts a knee meniscus and its various components;

FIGS. 21, 22 and 23 each depict various close-up views of an exemplary tack embodiment according to an exemplary embodiment of the present invention;

FIG. 26 depicts an exemplary delivery pathway used to insert an example implant according to an exemplary embodiment of the present invention;

FIG. 27 depicts an alternate view of the delivery pathway of FIG. 26;

FIG. 28 depicts the alternate view of the delivery pathway of FIG. 26 with the anatomical areas semi-transparent;

FIG. 29 depicts the alternate view of FIG. 28 with the device partially inserted into the tissue;

FIG. 30 depicts the view of FIG. 29 with the device fully inserted into the tissue;

FIG. 31 depicts various partially transparent views of the exemplary tack embodiment of FIGS. 21-23 as positioned in an example meniscus, showing the outer contour of the device transparently and the various irrigation pathways;

FIG. 39 illustrates exemplary materials and channel sizes using a micro-metal injection molding (micro-MIM) manufacturing process for the exemplary tack embodiment of FIGS. 22-26;

FIG. 45 illustrates exemplary materials and channel sizes using a corrugated sheet metal manufacturing process for the exemplary tack embodiment of FIGS. 21-23;

FIG. 47 illustrates exemplary materials and channel sizes using a single lumen extrusion manufacturing process for the exemplary tack embodiment of FIGS. 21-23;

FIG. 57 illustrates variant versions of a suture anchor type implant without the cap;

FIG. 66 is a chart presenting the various features of each of the configurations A through E of the suture anchor type implant of FIG. 65;

FIG. 69 depicts various magnified views of Configuration E;

FIG. 75 depicts various horizontal cross sections taken at various points along the respective shafts of Configurations A through E of FIG. 65, respectively;

FIG. 88 is a chart listing the MRI characteristics of osteoarthritis.

DETAILED DESCRIPTION OF THE INVENTION

In general, a meniscus is a crescent shaped fibrocartilaginous structure on either side of the knee joint. Similar structures are found in most human joints such as the wrist, hip, acromioclavicular joint and shoulder joint.

Figure 1:
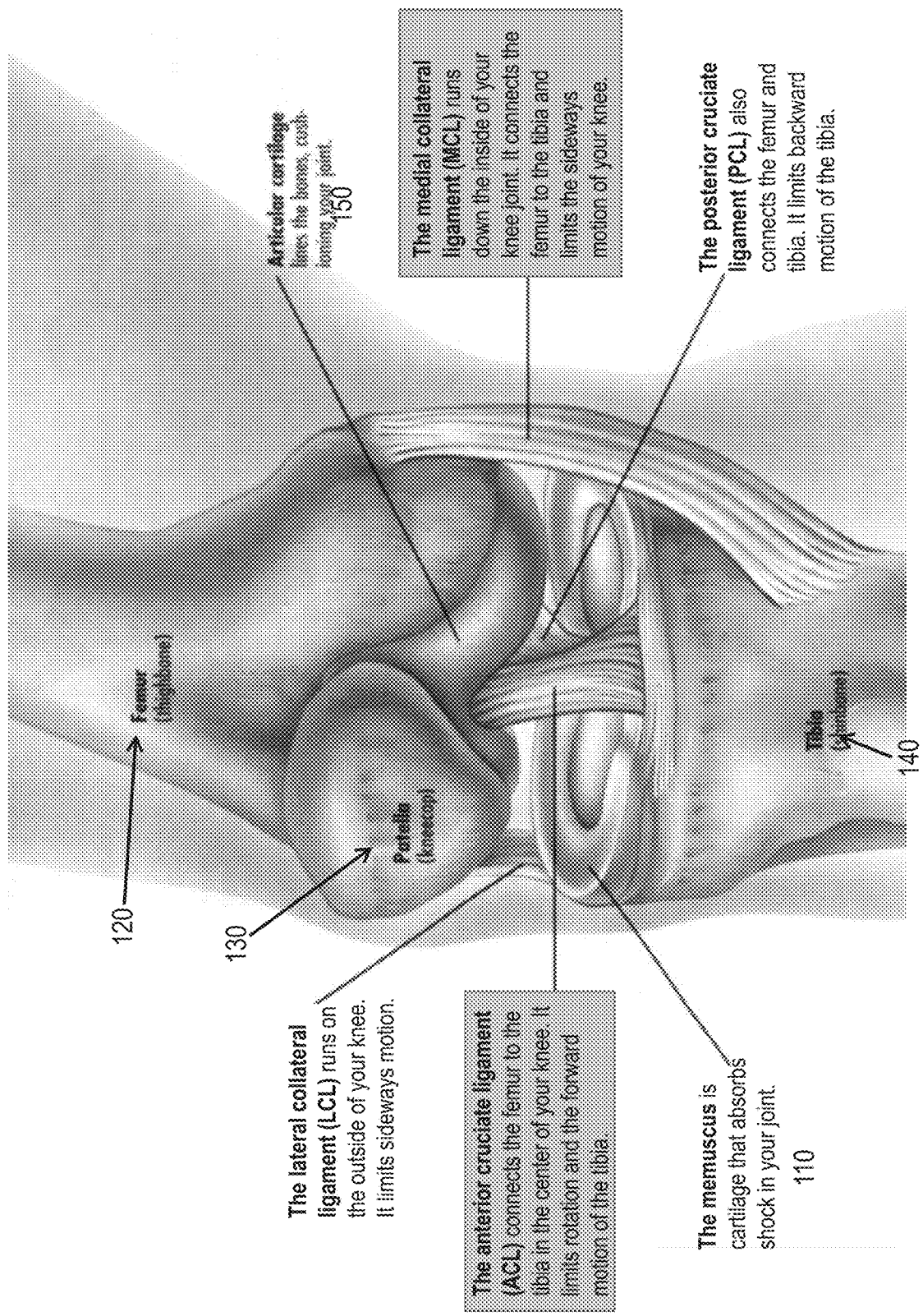
FIG. 1 illustrates basic anatomy of the human knee.
Figure 2A:
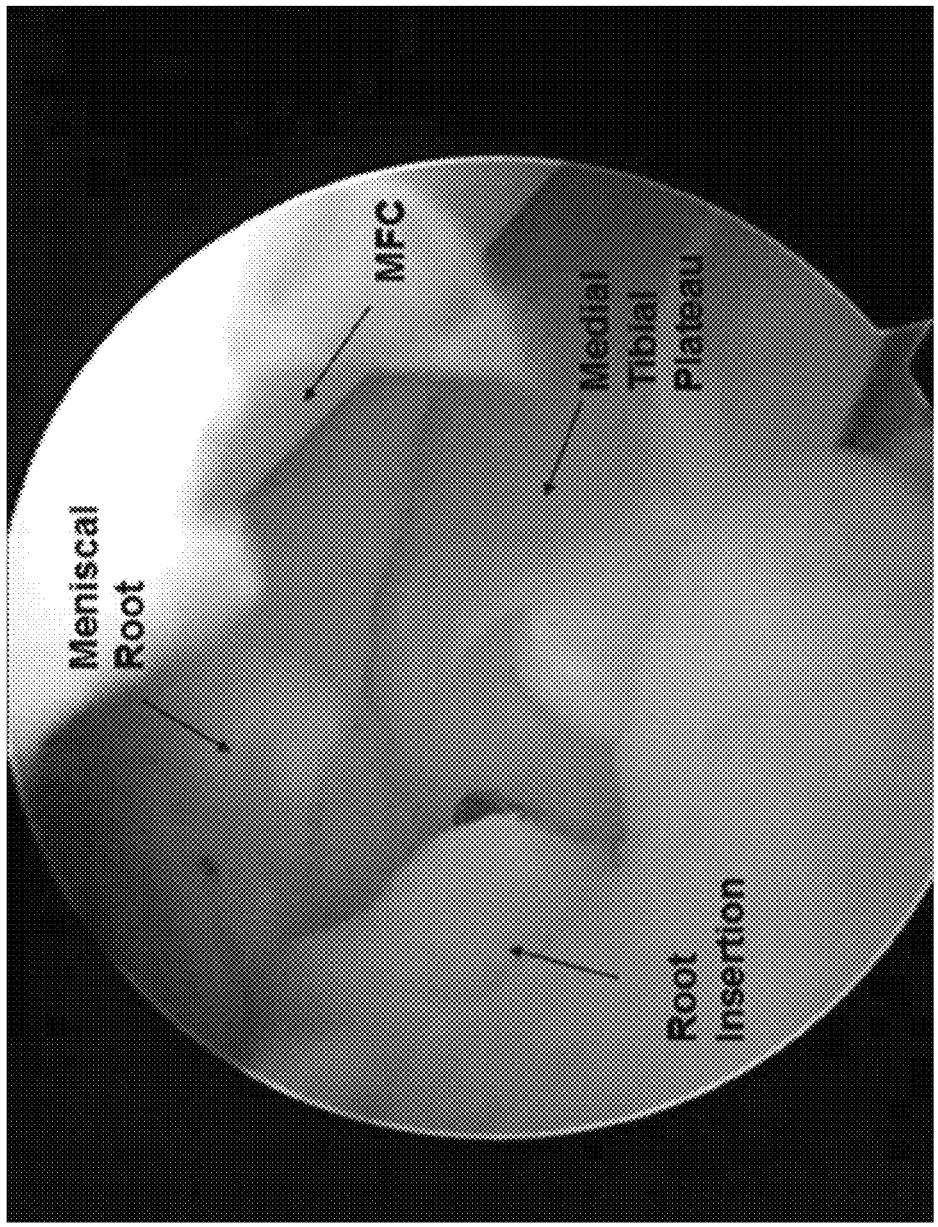
FIG. 2A depicts an internal view of the meniscal root, the Medial Femoral Condyle (MFC) and Medial-Tibial Plateau.
Figure 2B:
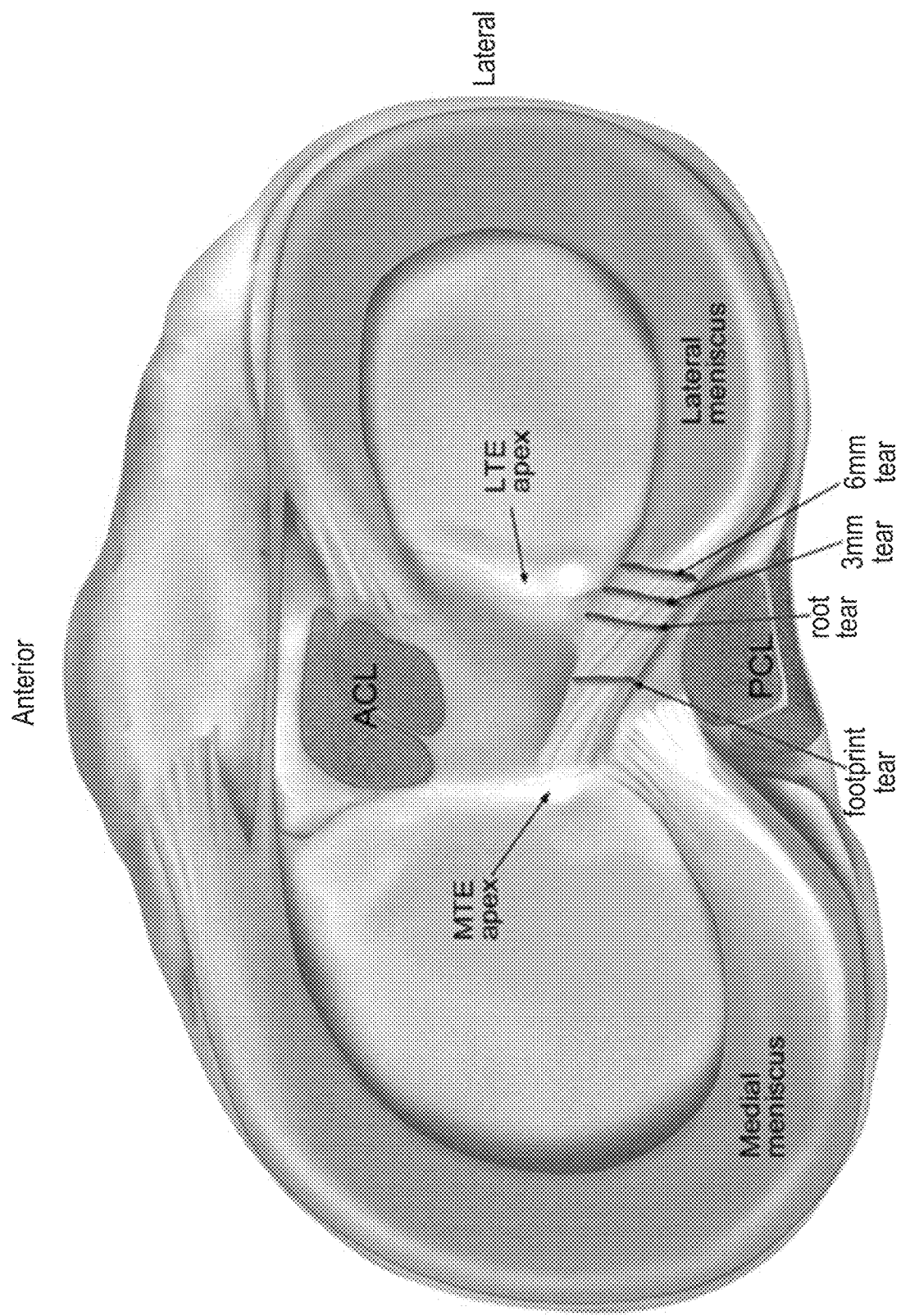
FIGS. 2B and 2C depict transverse views of the knee, FIG. 2B showing various types of meniscal root tears, and FIG. 2C showing the anterior and posterior roots, as well as the various neighboring ligaments.
Figure 2C:
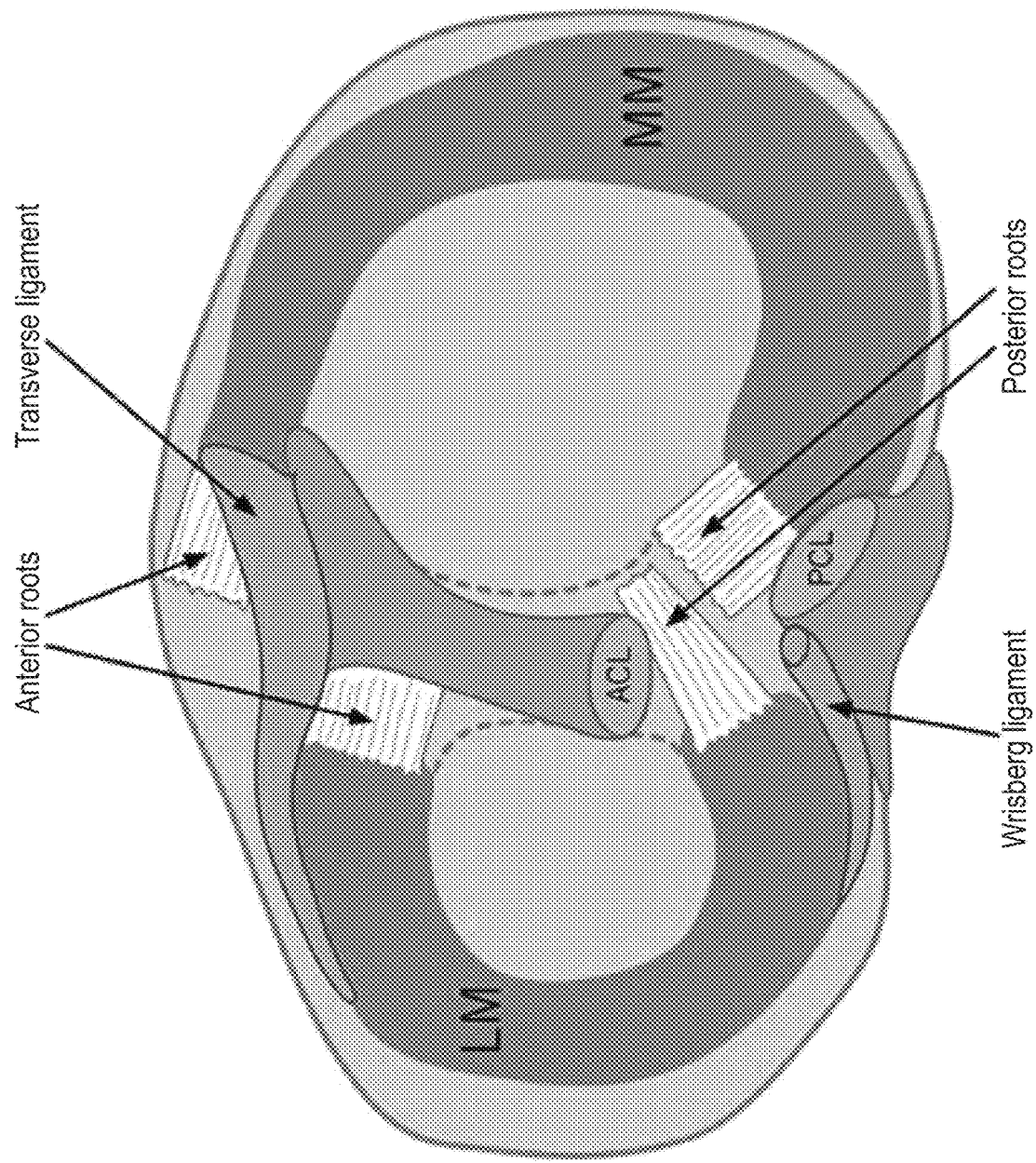

For ease of reference, FIG. 1 depicts the basic anatomy of the human knee, including the meniscus. Referring to FIG. 1, meniscus 110 is primarily composed of Type 1 collagen. As known, the meniscus comprises fibers in semi-circular patterns. It expands during compressive forces, which increases its contact area. It thus spreads out the load from the bone, and as a result, it protects Articular Cartilage 150 that lines the joint. It is the meniscus' circumferential fibers that allow for the dissipation of hoop stresses and, as a result, protection of the articular cartilage (see references 4, 10, 11). Once the meniscal root tears, the insertion of the meniscus to the tibia bone detaches and it can no longer sustain pressure from the bone.

Actually, a degenerative meniscal tear is believed to be an early sign of the development of osteoarthritis (see references 5, 6, 7, 8, 9). Moreover, it has been discovered that the peak contact pressure after a meniscal root tear is the same is in a total medial meniscectomy (11). Because after a root tear the circumferential fibers of the meniscus are disrupted, this may cause a loss of hoop strength, eventual extrusion of the meniscus, and altered biomechanical properties, causing dramatically accelerated degenerative changes in the knee joint. It is known that if the meniscus is removed, osteoarthritis tends to develop at an exponentially rapid rate. Moreover, even after a root tear, within 5-6 years many patients develop advanced arthritis. Therefore, the treatment of most meniscal root tears is indicated for the prevention of progression into osteoarthritis of the knee, as well as for symptomatic relief (12).

Various techniques have been used for the repair of the meniscal root. These include, for example, transosseus repair, stitch configuration and suture anchor repair (12, 13 Nicholas). No optimal location of the suture anchor placement has yet been determined (12). The current clinical "gold standard" is a transosseus technique: the transtibial pullout repair technique using a single transtibial bone tunnel (13). Here sutures are passed through the meniscal root and then through a bone tunnel drilled at the center of the posterior root of the medial meniscus. The sutures are then secured over a surgical button on the anterior medial tibia. An alternative transtibial technique has been proposed using two drilled tunnels. One is drilled through the center of the entire meniscal root while the second is passed through the attachment of the root fibers (13).

Nonetheless, these techniques have proven to be cumbersome and demanding, because of the small area in which drill guides, drills and sutures need to pass. Moreover, drilling, in itself, in this tiny and fragile area may be violating, and further may fail to preserve the integrity of the original anatomy. Finally, no known technique promotes resurgence of circulation to the meniscal root, which is understood by the inventor as crucial to healing, and preservation of the biomechanics of the knee joint.

These and other problems are addresses in exemplary embodiments. Moreover, implants according to various embodiments may be used prophylactically to prevent meniscal root tears and/or the onset or progression of osteoarthritis.

In accordance with various embodiments, an injured or weak human meniscus is addressed. It is noted that a weakened meniscus can lead to osteoarthritis (OA). While the following discussion focuses on the knee, it is equally applicable to addressing various other human joint maladies, such as, but not limited to, rotator cuff tears, labral tears and any tears of soft tissue that require the blood form bone (to which it is fixed) for healing. All of which are to be understood as the subject of various embodiments disclosed herein.

In accordance with various embodiments, various techniques, using various implant devices and delivery systems, may be used to cure meniscal root tears, prevent meniscal root tears or degenerative meniscal tears, and prevent the progression or onset of osteoarthritis of the joint (degenerative disease) and rejuvenate the joint.

In accordance with various embodiments, implants and associated techniques may (i) comprise a minimally invasive technique for repairing the meniscal root that recreates the natural anatomy without requiring violating drill holes, and may (ii) provide for recirculation of blood flow and nutritional healing elements into the meniscal root.

As understood by the inventor, significant recent medical evidence proves that meniscal root tears may lead to a destructive cycle of progression of knee arthritis. Millions of people suffer from osteoarthritis with gradual onset evidenced only by subtle early findings on MRI and X-rays. Most of these patients do not have overt tears of the meniscal root and a definitive cause of the OA is often never determined. The present inventor believes that patients with the insidious onset of knee osteoarthritis have interstitial dysfunction or damage of the meniscal root—but without a tear. The meniscal root, equivalent to the roots in a tree, provides a nutritional bridge between the meniscus itself and the core of the bone marrow and the nutrition providing material produced therein. The bone marrow produces all the stimulating factors for healing and maintaining the meniscus. Compromise of this bridge—due to decreased vascularization through the root (e.g., through clogging)—leads to degeneration of the joint much like root disease leads to degeneration of a tree.

Therefore, a third and perhaps most significant goal of the present invention is to slow down or stop the progression of osteoarthritis in the knee by rejuvenation of the meniscal root. This allows for maintaining the dissipation of hoop stresses by the meniscus, and, as a result, protection of the articular cartilage and preventing the development of osteoarthritis.

It is the inventor's belief that patients with early and subtle findings of osteoarthritis, which may be diagnosed through X-ray and MRI imaging, would benefit from a meniscal root replenishment and repair because it would stop the progression of osteoarthritis. This would limit a significant amount of morbidity in the population as well as dramatically diminish the need for future total knee replacements. This, in turn, would prevent many medical complications (including death) as well as save billions of dollars in cost. The implant and technique of the present invention can provide the needed rejuvenation. FIGS. 88 and 89, discussed below, respectively provide exemplary X-ray and MRI diagnostic criteria for early findings of osteoarthritis, which may, in embodiments, be used to determine when to implant a device to, for example, forestall degradation of the meniscus, and thus stop the onset of osteoarthritis.

Exemplary Implant Devices

A. Blade and Washer Type Implant Device

Figure 20:
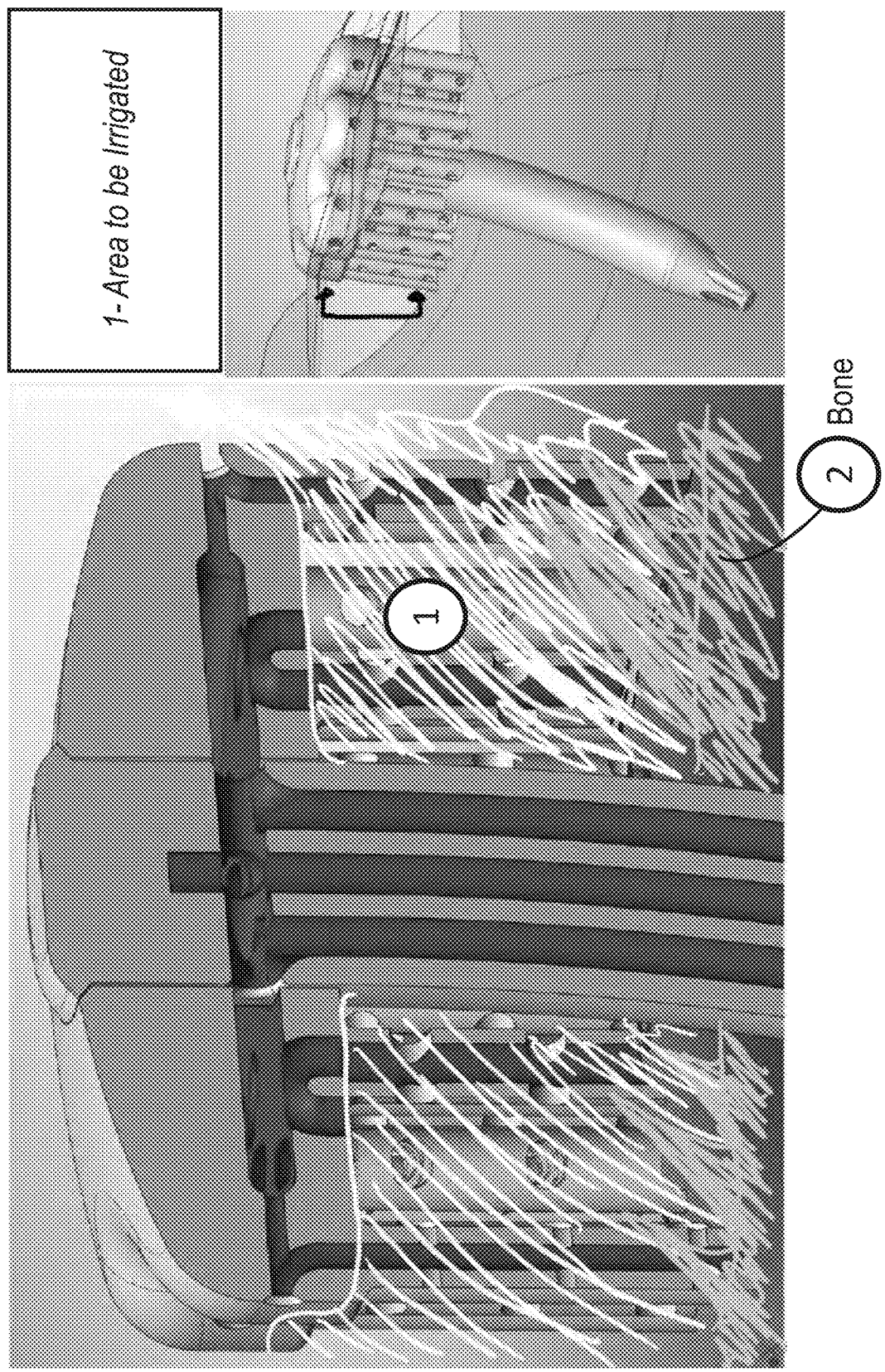
FIG. 20 illustrates the exemplary implant device of FIGS. 15 and 16 as positioned in a knee meniscus, showing an area of the meniscus to be irrigated.

An exemplary first embodiment of an implant device is shown in various views in FIGS. 3-18 and in FIG. 20. The exemplary implant includes two parts, known as the "anchor" or "blade" and the "washer" or "slider." A delivery device (see FIG. 4) may be initially attached to the anchor, with the washer or slider positioned on the upper portion of the shaft of the delivery device. Additionally provided may be a slider handle, which may later be used to slide the washer down the delivery device and into final position, surrounding the anchor. Once the anchor and washer are affixed to the patient's meniscal root, and the anchor affixed to the patient's bone, the delivery device and slider handle may be removed.

Figure 3:
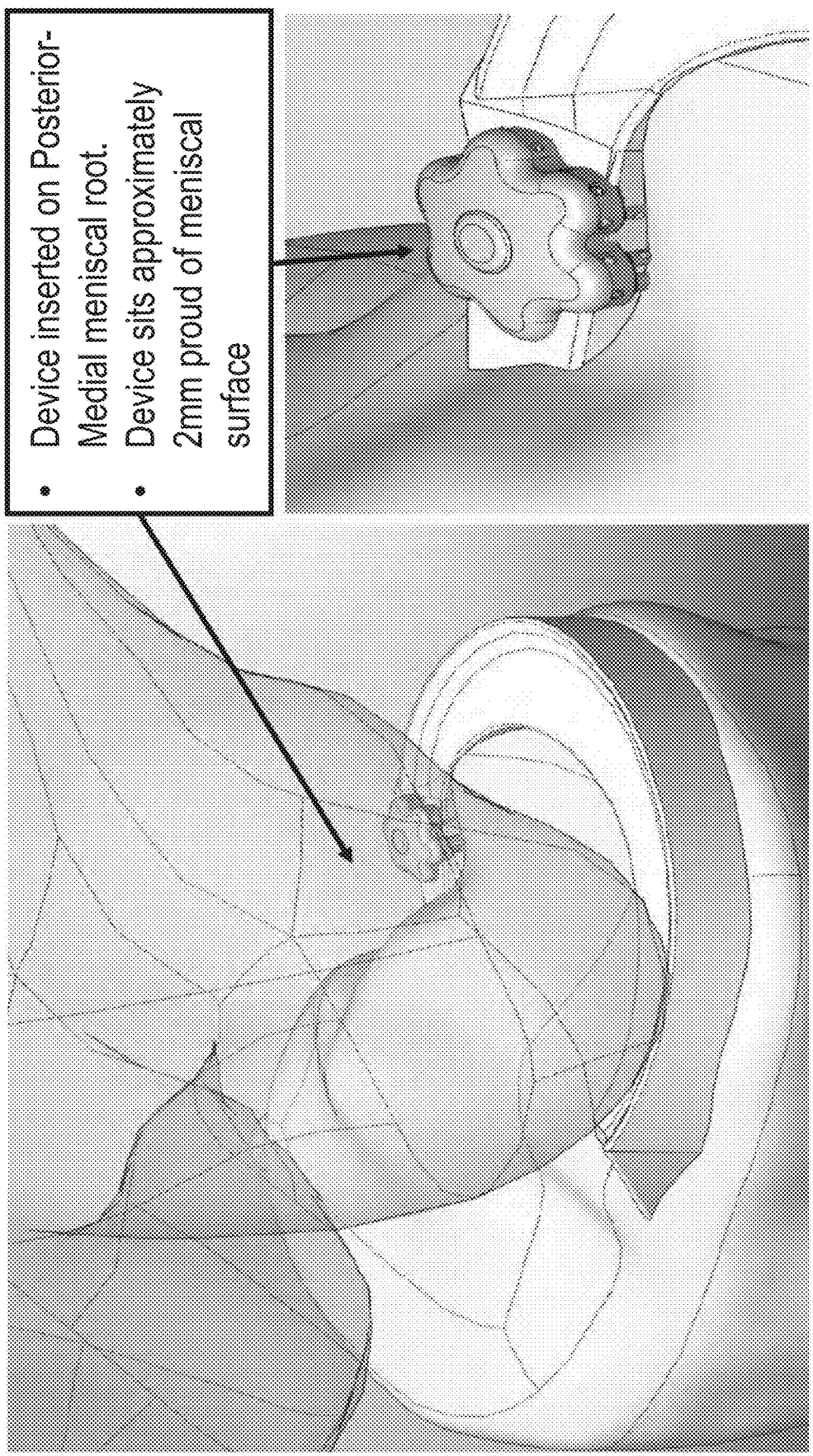
FIG. 3 depicts an exemplary implant device inserted in the posterior-medial meniscal root according to an exemplary embodiment of the present invention.

First described is an example implant device in accordance with various embodiments, that both secures the meniscus in place as well as creates a pathway (or multiple pathways) for the flow of blood and nutrients inside the bone to the meniscus. FIG. 3 depicts an exemplary implant device inserted in the posterior-medial meniscal root according to various embodiments. In the example shown in FIG. 3 the device may, for example, sit approximately 2 mm proud of the meniscal surface. However, in other embodiments, some of which are described below, the device need not be proud at all and may, for example, actually be flush with surrounding tissue, or sit slightly below the surface of surrounding tissue, having pulled some of the meniscus down with it, as described below.

Figure 4:
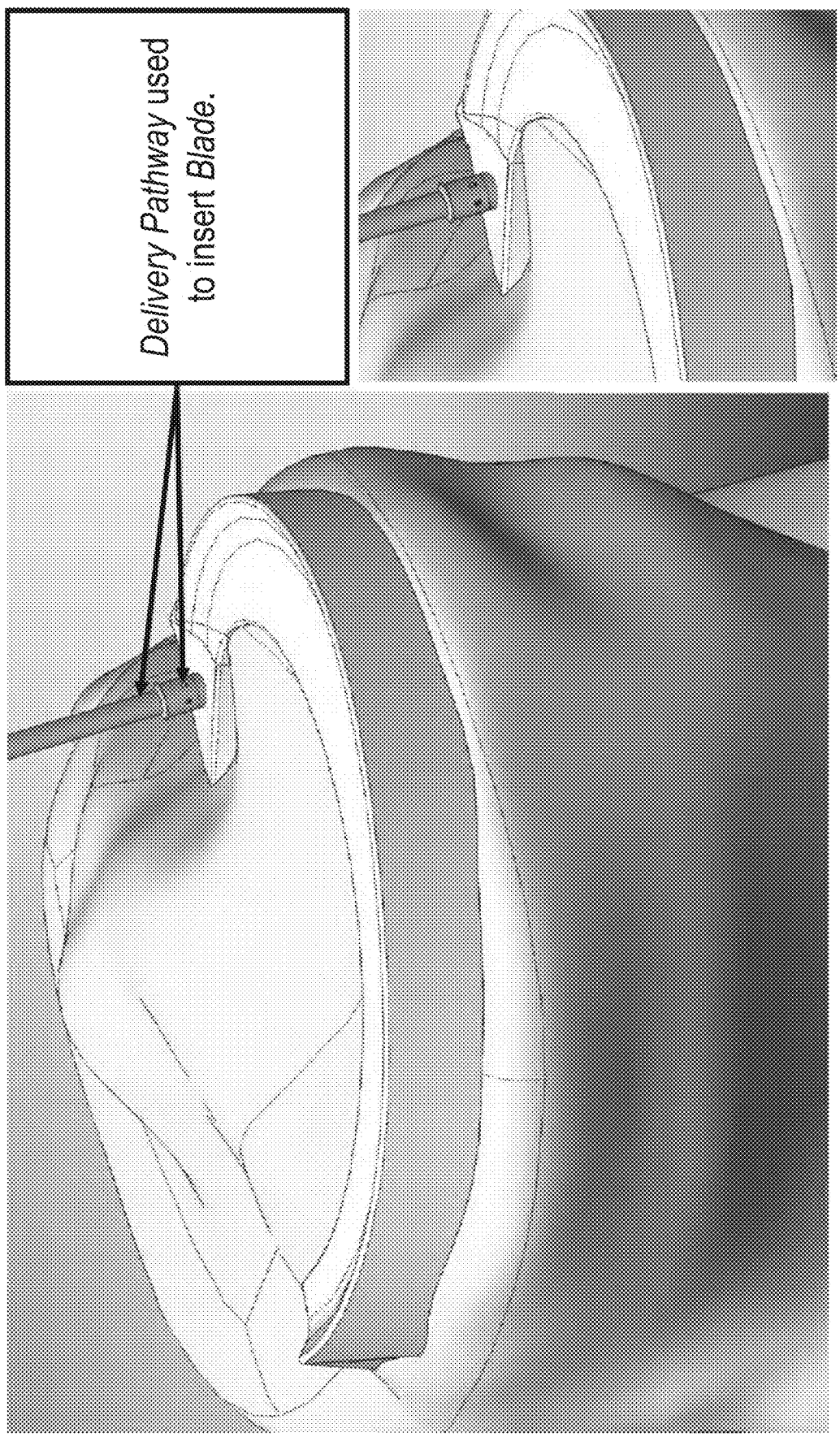
FIG. 4 illustrates a blade of the exemplary implant of FIG. 3 being inserted by a delivery device.

FIG. 4 illustrates a blade or central shaft of the exemplary implant of FIG. 3 being inserted by means of a delivery device. In this exemplary embodiment there are two components to an exemplary implant device, known as a "blade" or "central shaft" and a "washer" which fits around the central blade and provides pathways to spread out the blood and nutrients which are delivered by the device, and which may travel up the central shaft. In accordance with various embodiments, the central shaft may first be inserted into the meniscus, and once secured, the washer may be fit over it and clicked into placed as described below. Thus, FIG. 4 illustrates an initial step of using a delivery device to insert the central shaft or blade. The blade, or central shaft thus anchors the device into the patient's tissue and bone.

Figure 5:
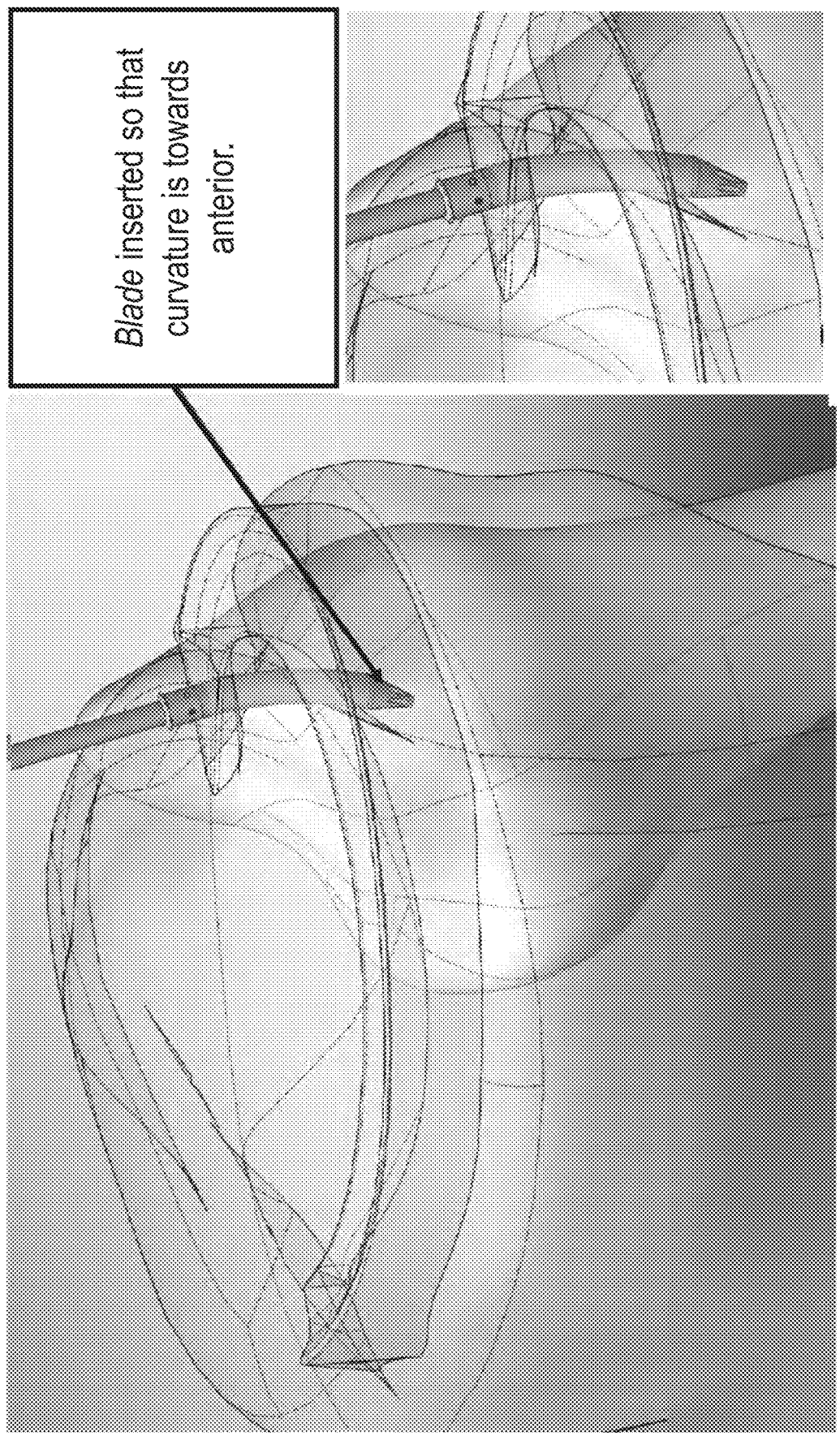
FIG. 5 illustrates how the blade is inserted such that the curvature is towards the anterior.

FIG. 5 illustrates that the blade may be inserted so that the curvature of its shaft faces toward the anterior portion of the knee, or the meniscus. This facilitates insertion, as a curved implant may, for example, be delivered to the meniscus from an anterior approach and then pushed into place. In general, other approaches may alternatively be used, as described below, such as, for example, a posterior medial portal, in which case the curve of the distal portion of the implant may be medial, or anterior medially. However, although possible, it is not preferred to have the distal tip curve posteriorly.

Figure 6:
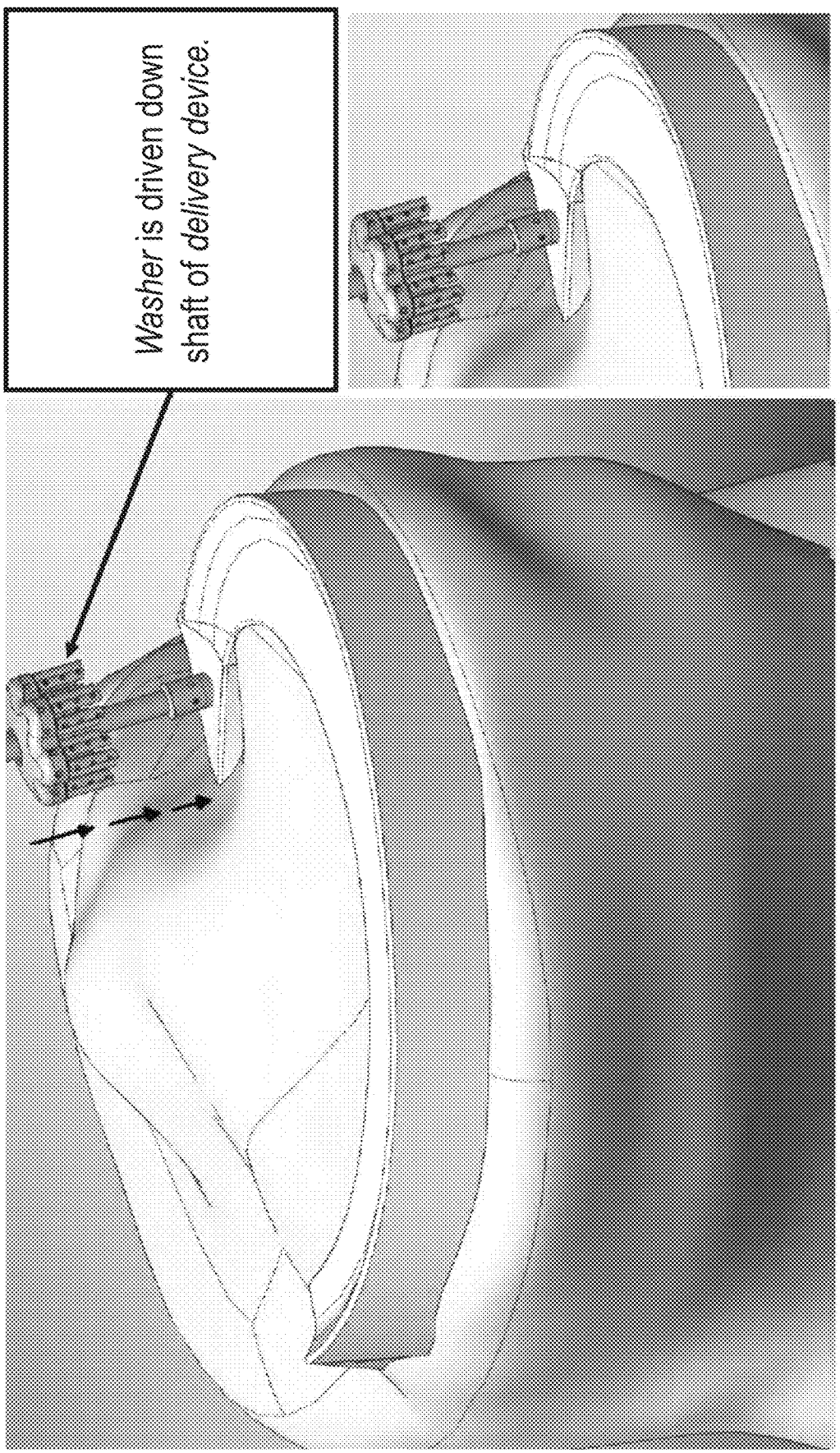
FIG. 6 depicts an exemplary washer being driven down the shaft of an exemplary delivery device according to an exemplary embodiment of the present invention.
Figure 7:
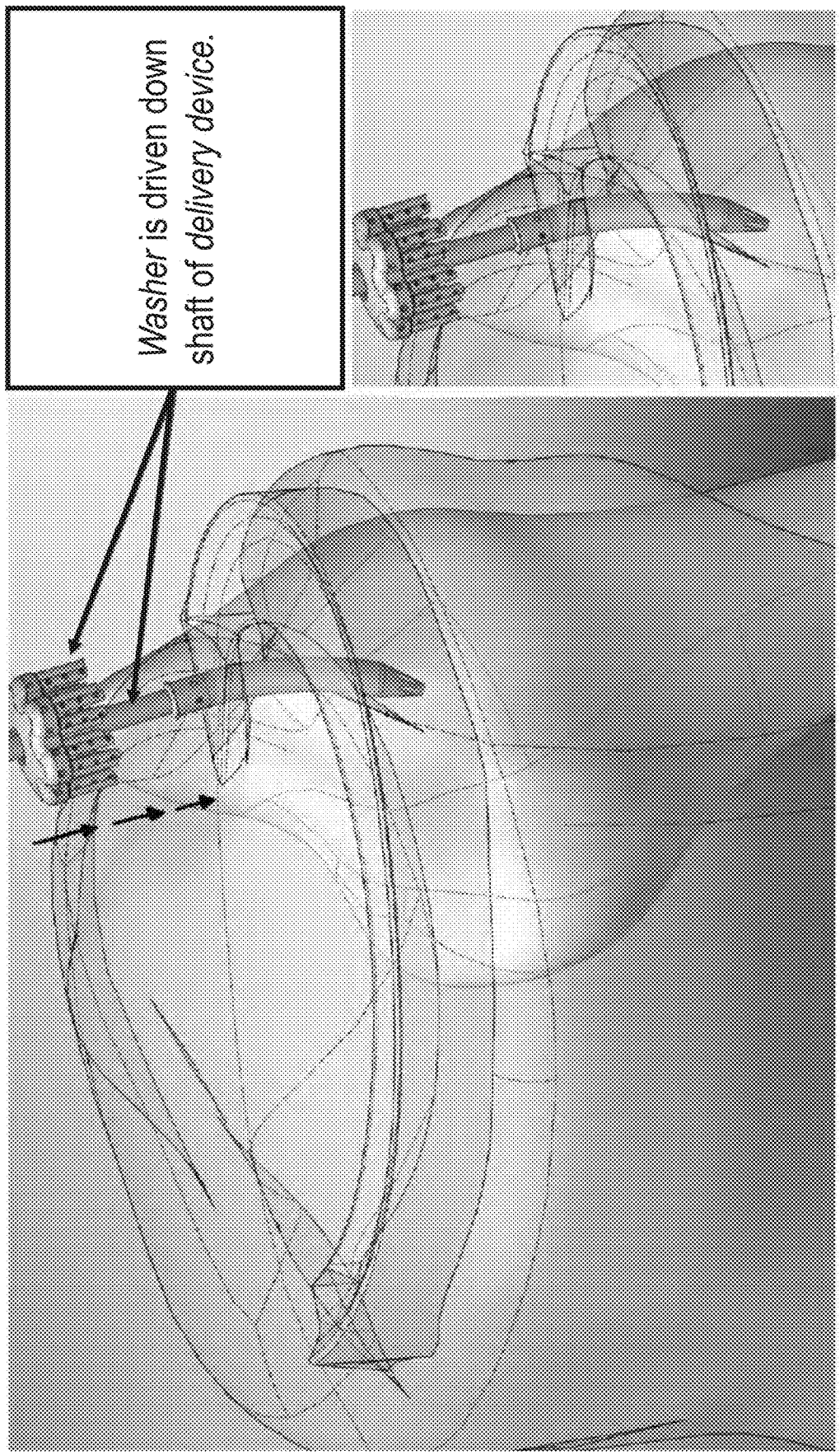
FIG. 7 depicts the exemplary washer and shaft of exemplary delivery device of FIG. 6, showing the relevant anatomy as semi-transparent.
Figure 8:
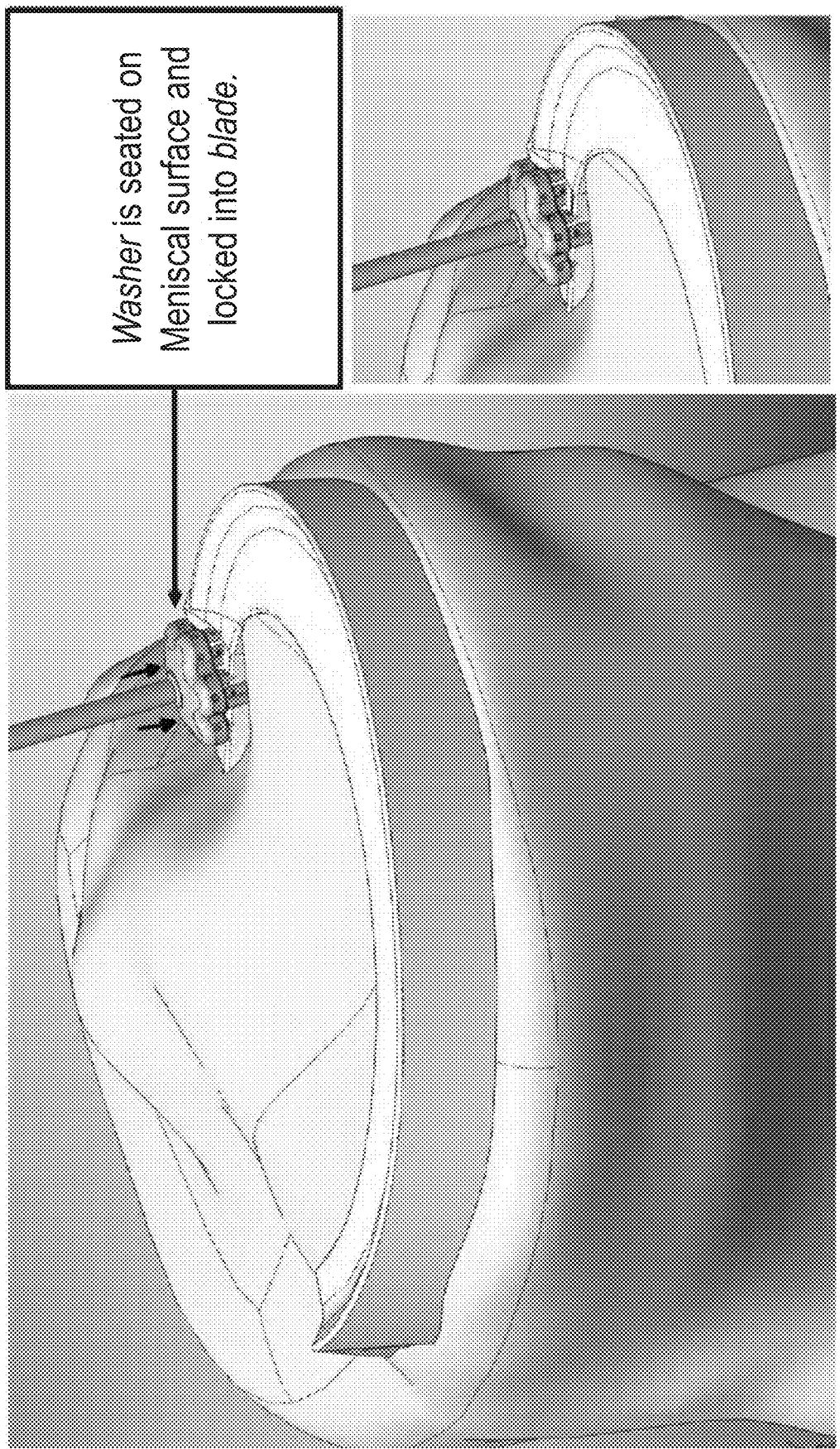
FIGS. 8 and 10 depict how the exemplary washer of FIG. 6 is seated on the meniscal surface and locked into an exemplary blade according to an exemplary embodiment of the present invention.

FIGS. 6 and 7 illustrate an exemplary washer being slid down the same delivery device used to insert the blade (as shown in FIGS. 4 and 5) which may then be pushed down and locked into place around the tip of the blade, as shown. It is noted that FIG. 6 depicts the meniscus and surrounding structures in the human knee as being opaque so that in the view of FIG. 6 one can only see the portion of the implant device that still protrudes above the meniscus. FIG. 7 is a transparent rendering of those same structures to allow for orientation of where the blade sits in its final position. Therefore, FIG. 8 shows the washer as seated on the meniscal surface and locked into the blade. As noted above, although this particular rendering depicts the washer as being slightly proud relative to the meniscus, it may, in embodiments, actually be flush with it, or even slightly below the surface of the meniscus and surrounding tissues, as described in greater detail below.

Figure 9:
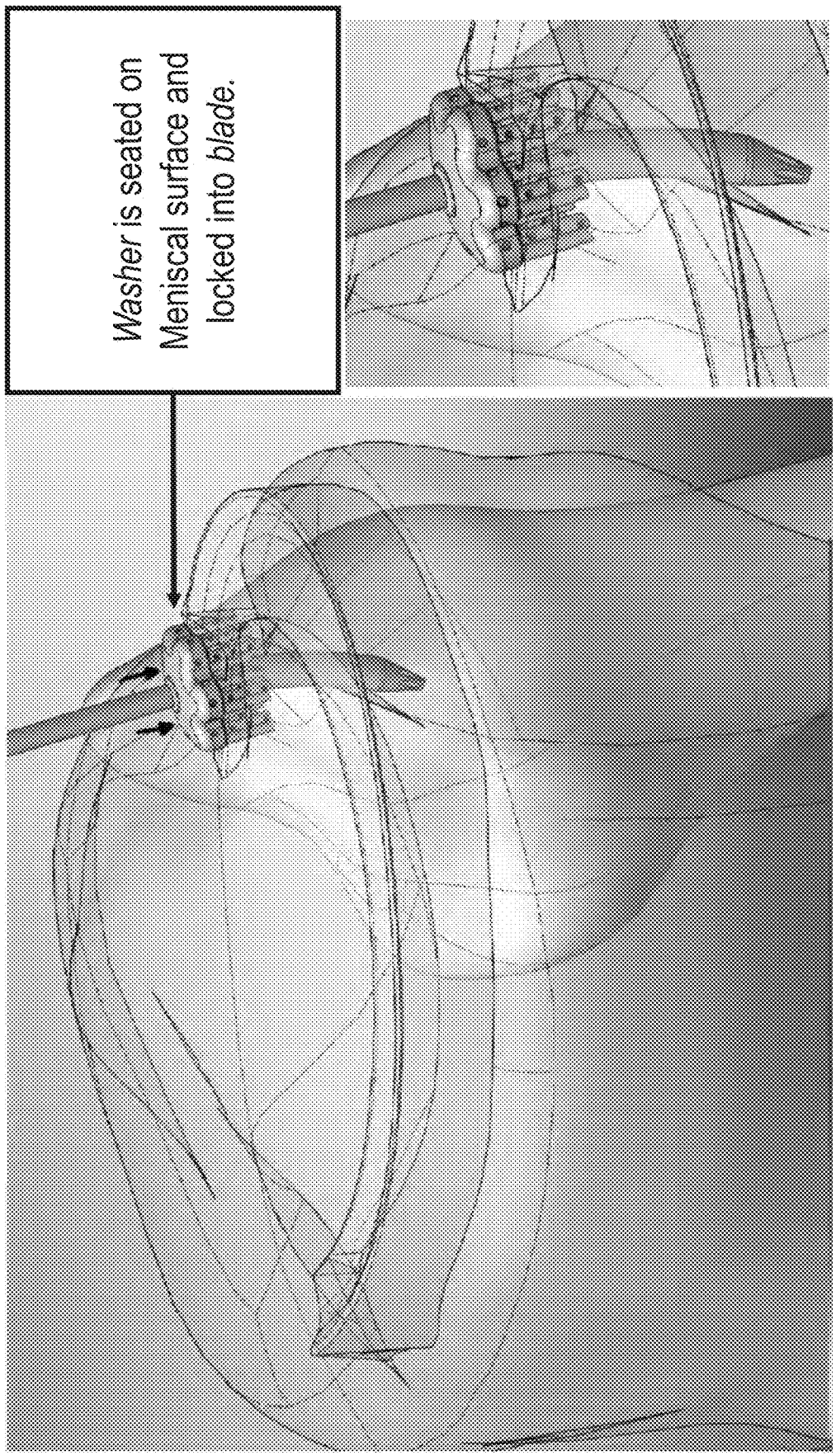
FIGS. 9 and 11 are transparent views of the process shown in FIGS. 8 and 10.

Similarly, FIG. 9 shows a transparent rendering of the washer as seated and locked onto the blade.

Figure 10:
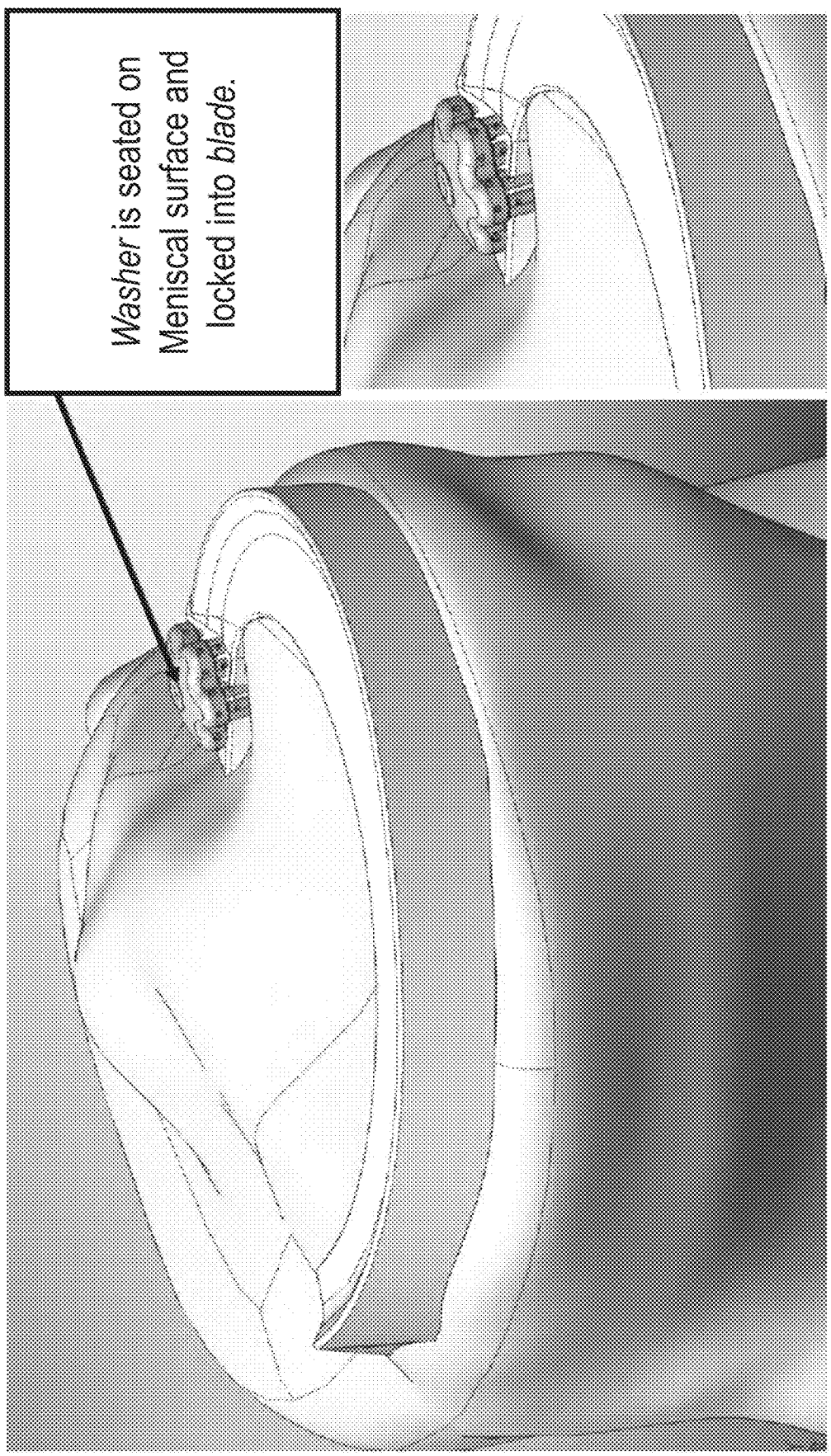
Figure 11:
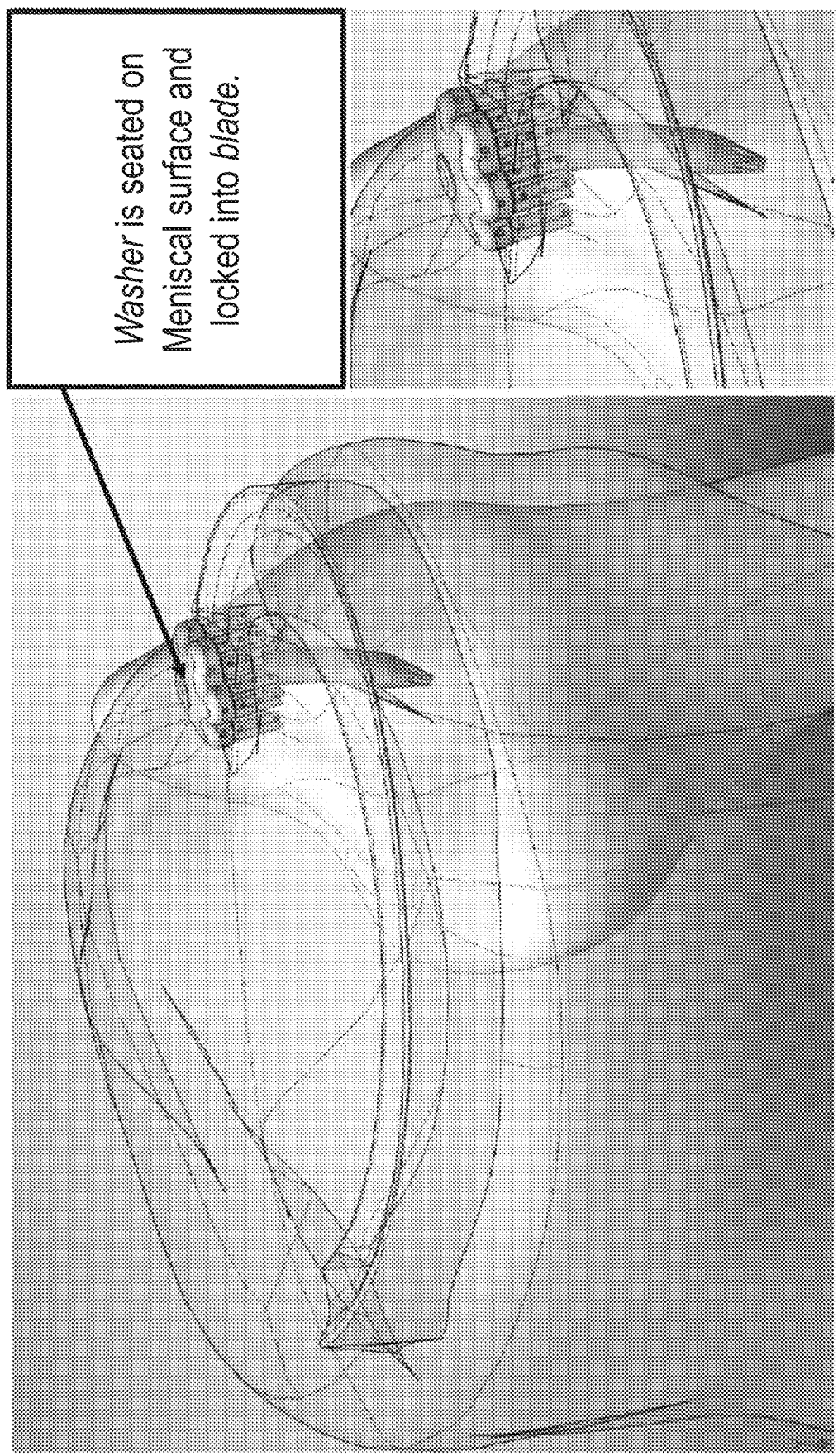

FIGS. 10 and 11 show the washer and blade in their final position, once the delivery device has been removed.

FIG. 12 shows exemplary elements of the exemplary implant device, in accordance with various embodiments. With reference thereto, there is shown Washer 1, Blade 2, Locking Interface 3, Perforations for blood flow 4, Microtubes 5 and Perforations 6 in the distal tip of the Blade for blood and nutrients to enter from inside the bone and travel upwards.

Figure 13:
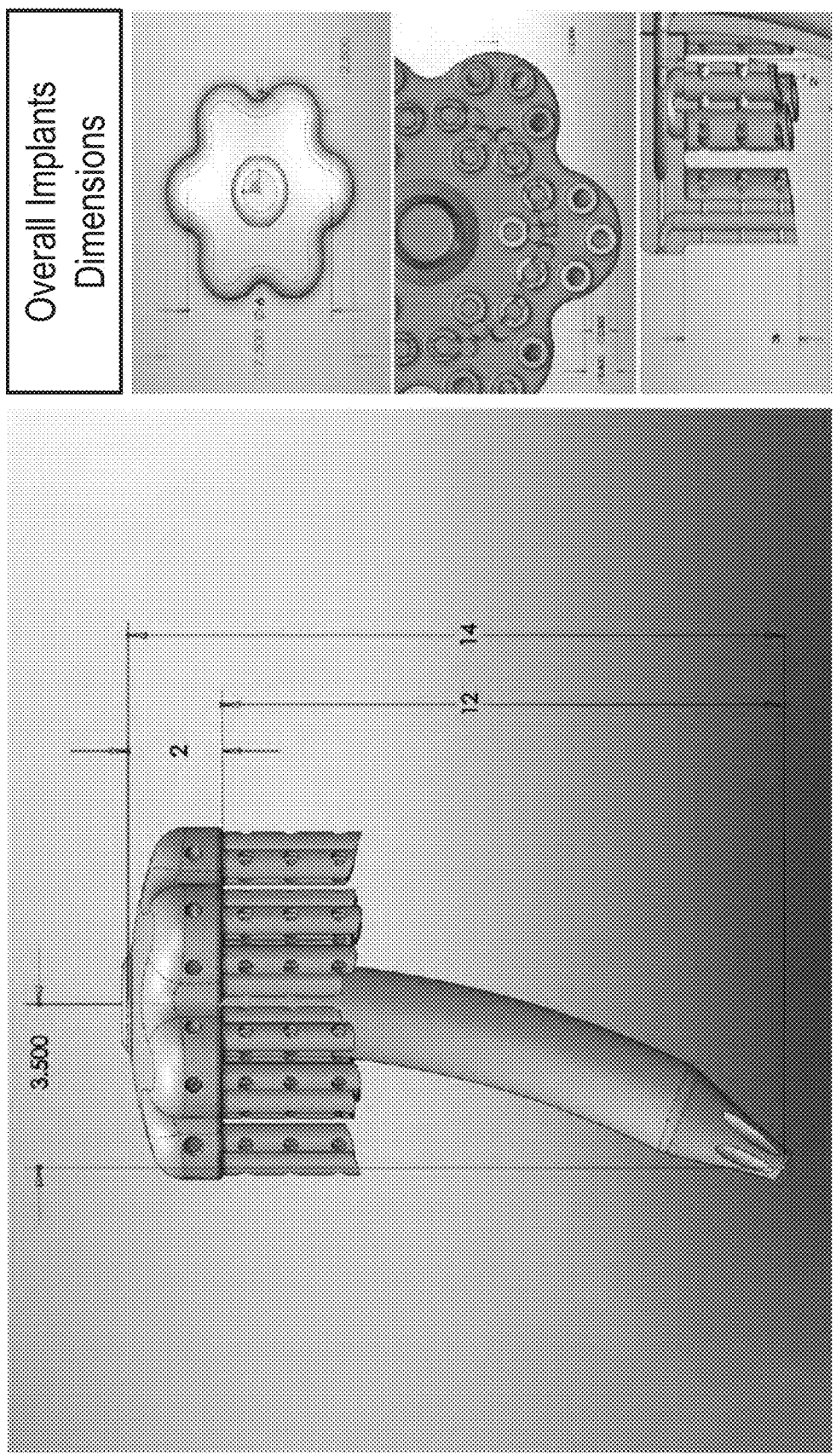
Figure 13A:
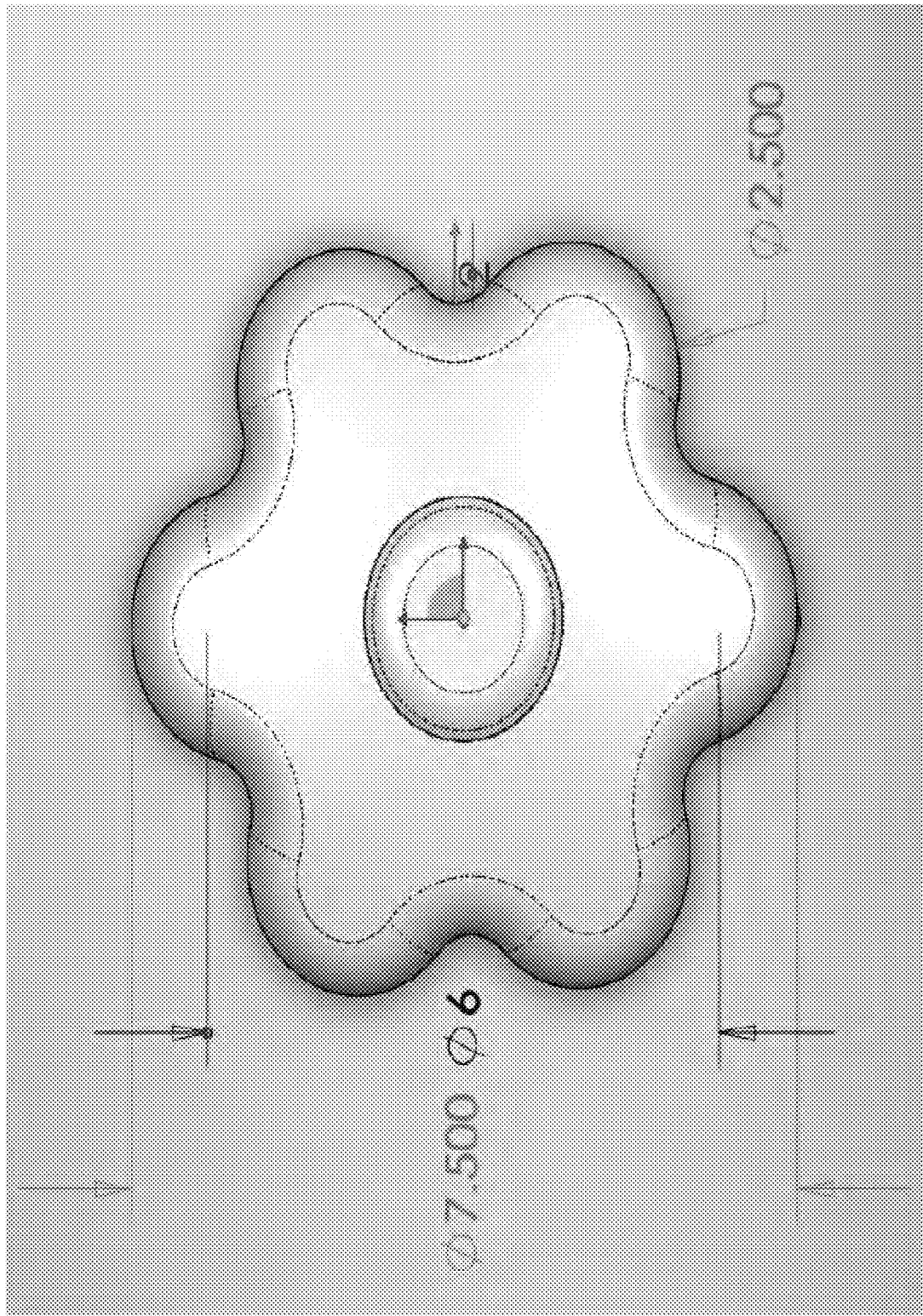
Figure 13B:
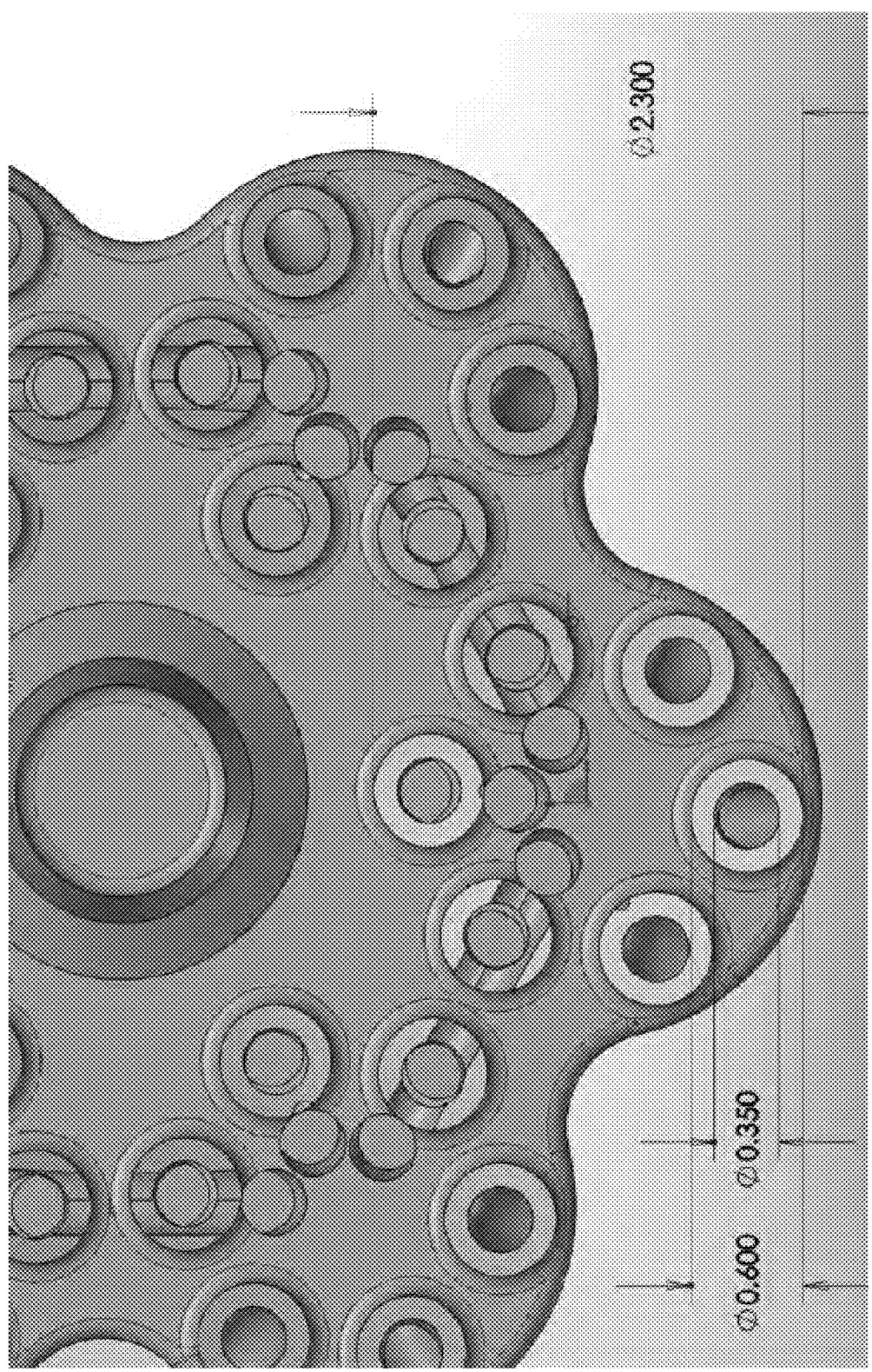
Figure 13C:
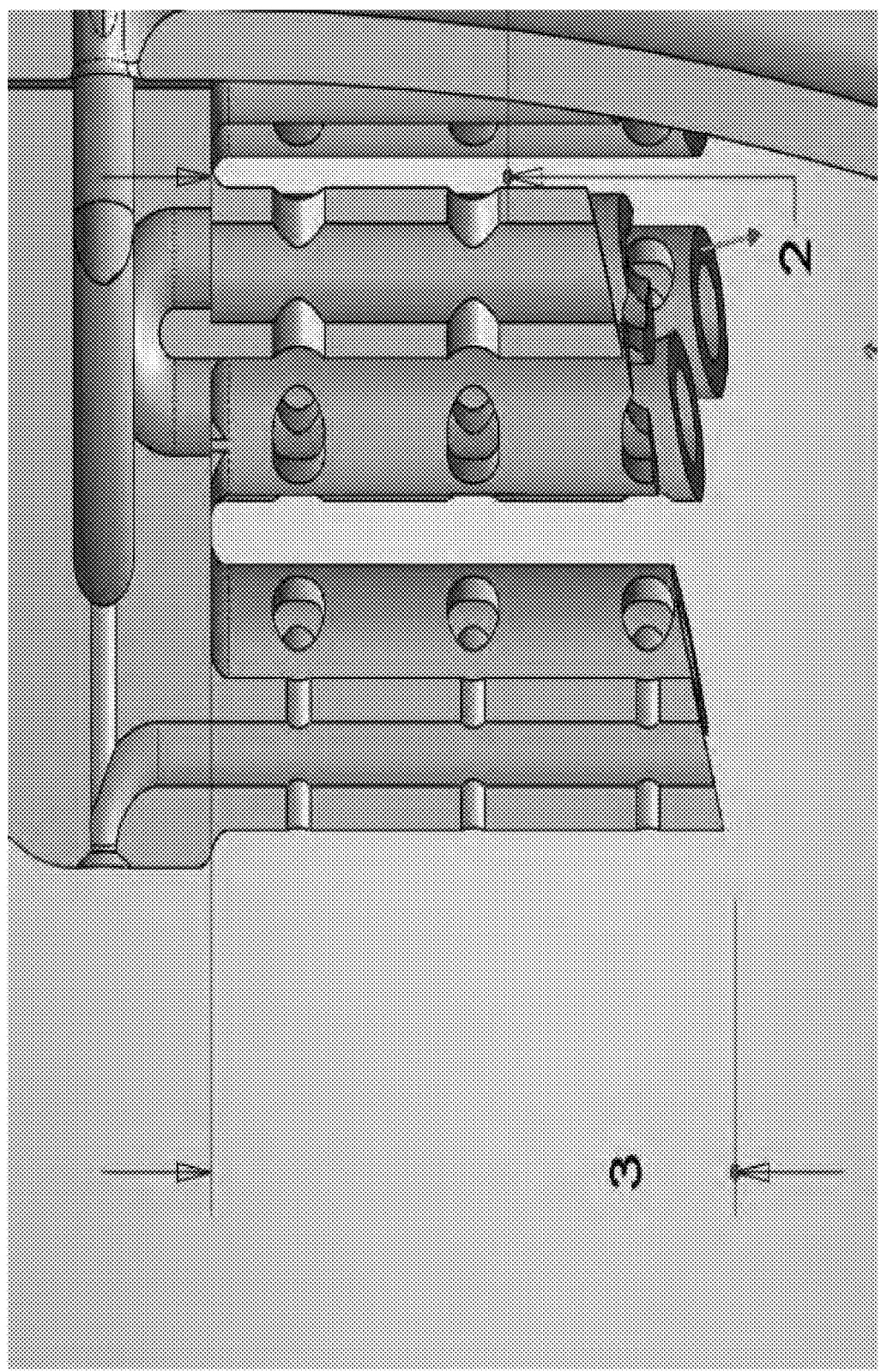

FIGS. 13, 13A, 13B and 13C show exemplary overall implant dimensions for the exemplary device of FIG. 12. These example dimensions are in millimeters. FIGS. 13A, 13B and 13C are magnified views of the three detailed images on the right side of FIG. 13. In FIG. 13A, for example, one can see the outer diameter of the Washer at 7.5 mm, a 6 mm diameter of an inscribed circle within the Washer, and a radius of curvature of a single fleurette of the washer of 2.5 mm.

FIG. 13B depicts an underside view of the Washer, and openings for various tubes that may protrude downward from the undersurface of the Washer (such as are depicted in FIGS. 12 and 13) showing a 0.35 mm inner diameter of an example tube, a 0.6 mm outer diameter of the example tube, and a 2-3 mm distance between an inner row of tubes and an outer most tube at the apex of a fleurette.

FIG. 13C is a magnified side view of structures in the Washer.

Figure 14:
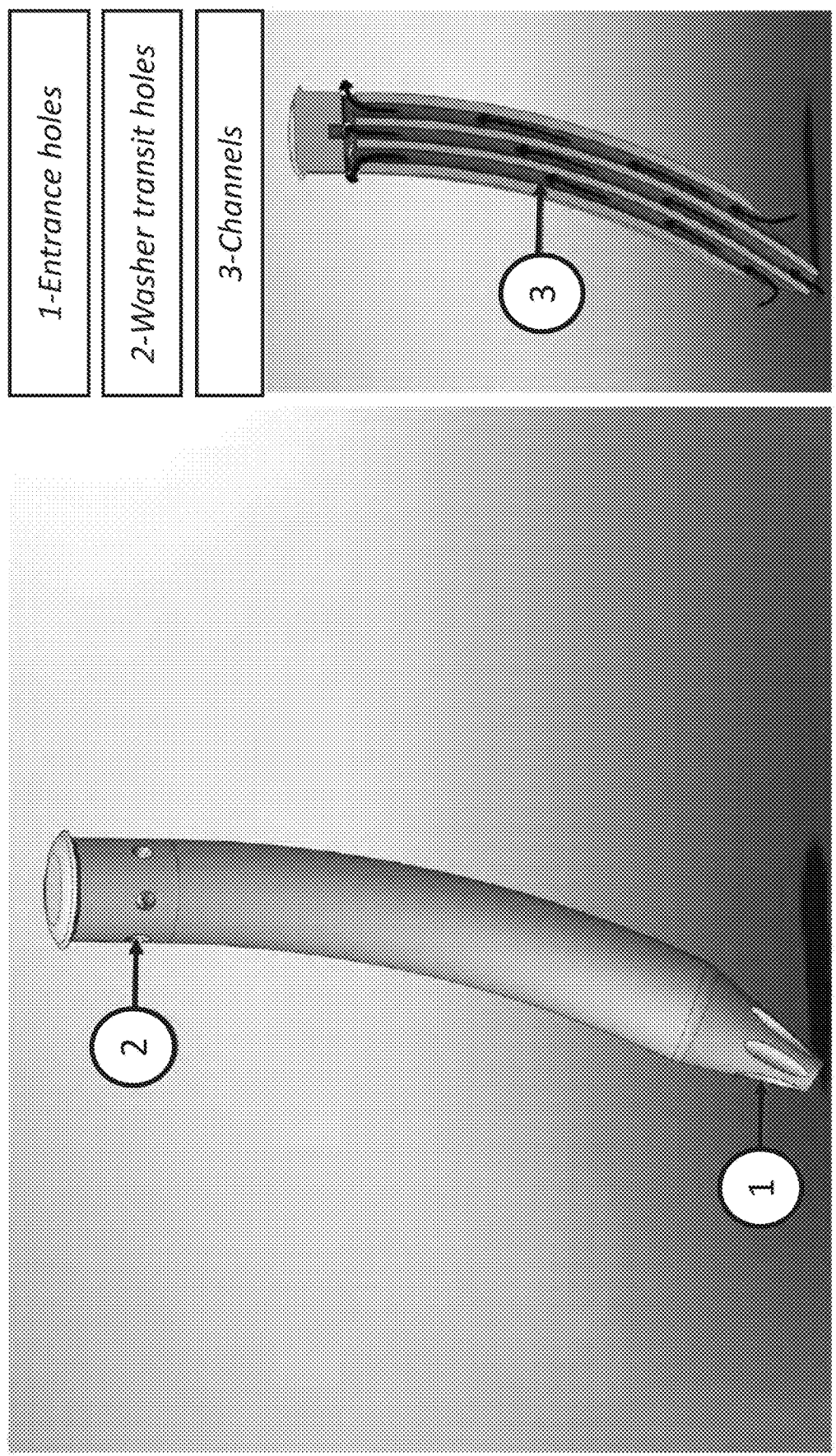
FIG. 14 illustrates an example blade, and exemplary irrigation canals within it.

FIG. 14 illustrates various components of the Blade, or central shaft of the example implant, including Entrance Holes 1, Washer Transit Holes 2 and Channels 3. The Channels 3 are interior to the shaft and shown in the right panel of FIG. 14, as well as in FIGS. 15 and 15A. It is noted that, in embodiments, Washer Transit Holes 2 may convey blood and nutrients (that come up the central shaft) outward horizontally so that they may be defused in the network of canals of the Washer, which are next illustrated. Therefore, with reference to FIG. 15, once can see the Washer locked into place over the Blade, and also see how Washer Transit Holes 2 convey the blood and nutrients horizontally to passages within the Washer. Those passages are horizontally connected to both external openings 4 as well as downward paths which proceed along various small cylindrical shafts that protrude downward from the bottom surface of the Washer, as shown in FIGS. 12 and 13. It is noted that Washer Transit Holes 2 of the shaft may either open into separate horizontal channels in the top of the Washer, or, alternatively, into a central disk like internal volume, in the nature of a fluid distribution cap or manifold, and that cap or manifold may, in turn, be connected to each of the vertical pathways provided in the Washer, as shown. Either embodiment may be implemented.

Figure 16:
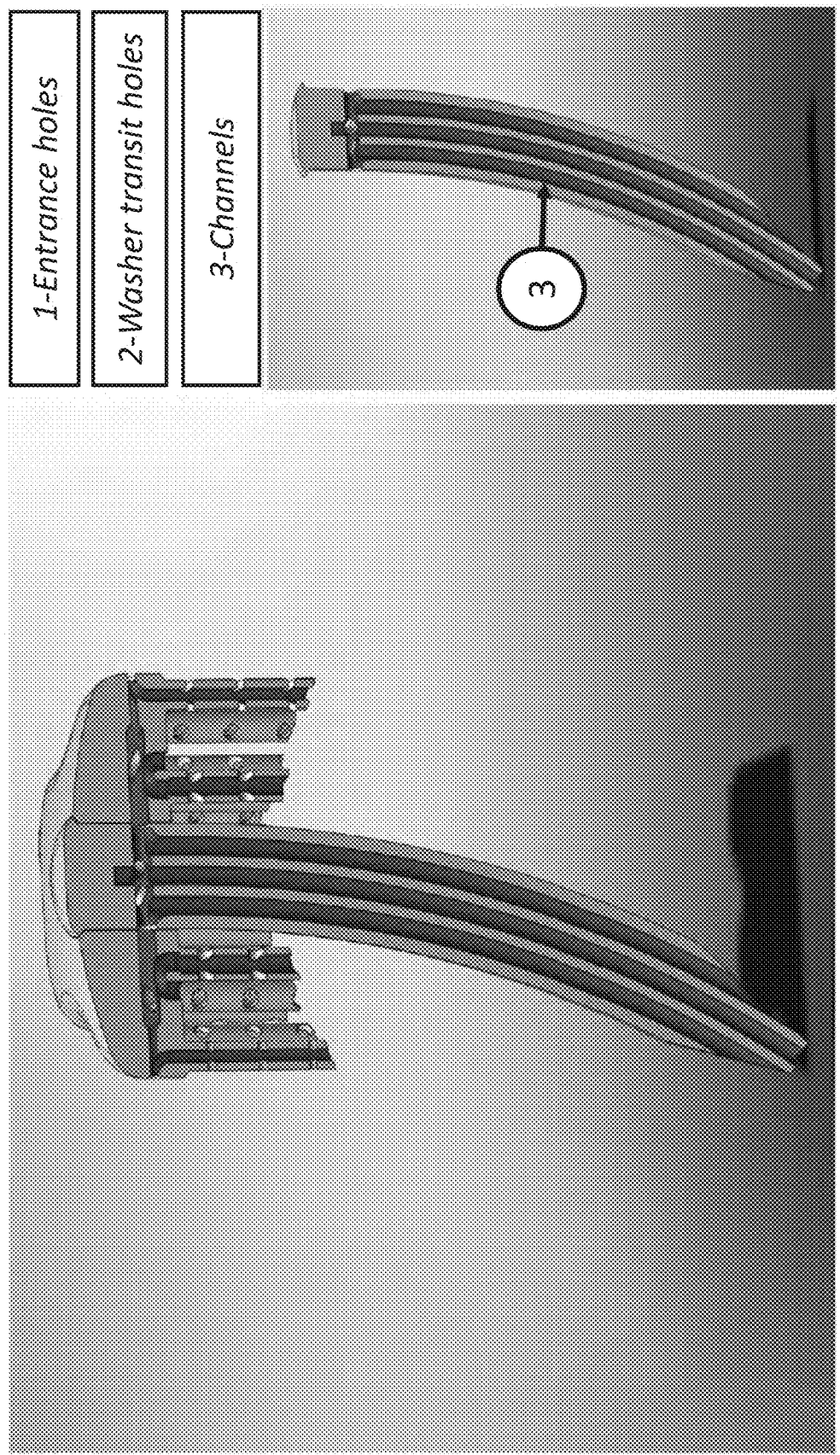
FIG. 16 is a full view of the example blade and washer structures of FIG. 15.

FIG. 16 shows the Washer and Blade combination in full view.

Figure 18:
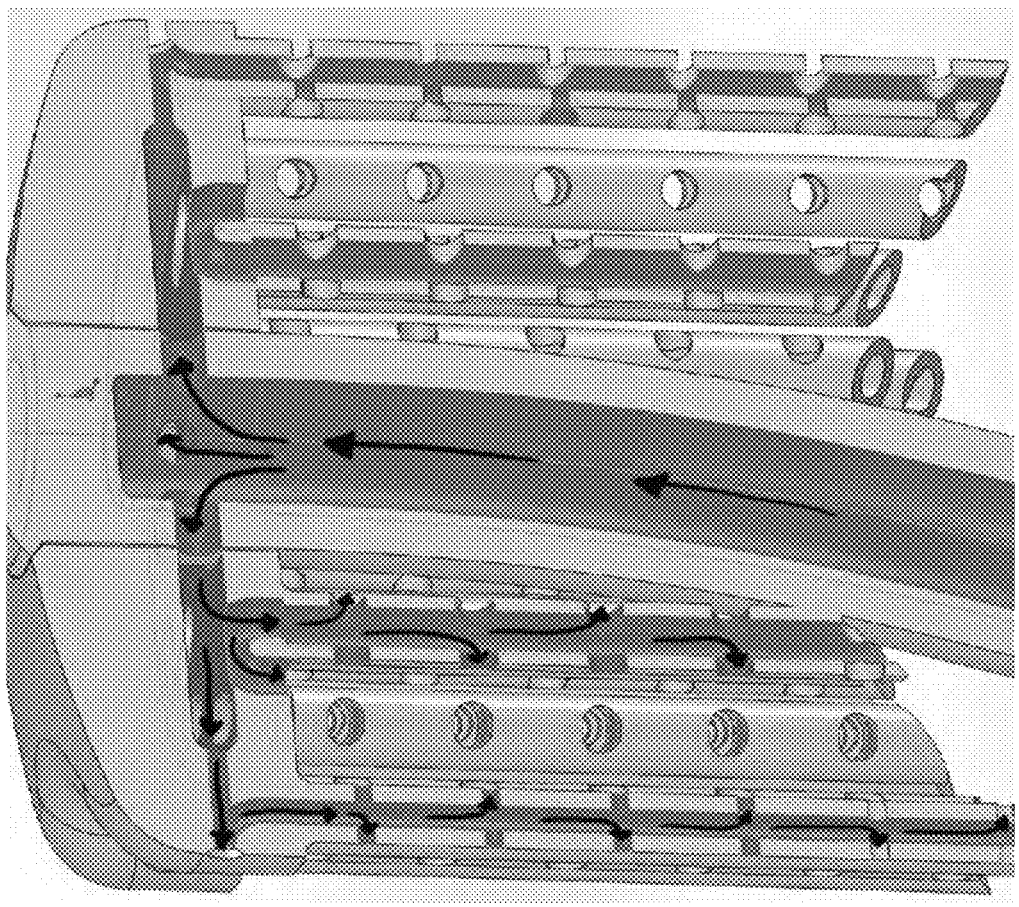
FIG. 18 illustrates a magnified view of the irrigation pathways in the blade and washer structures of FIG. 17.

FIGS. 17 and 18 illustrate details of the irrigation pathways for blood and nutrients up from, for example, cancellous bone connected to a joint (here a knee) into the central disk or manifold, or central distribution system, of the Washer. FIG. 18 is a magnified view of the Washer and an upper portion of the Blade. With reference thereto, the flow from the center of the Washer continues through the network of tubes and access ports provided in the Washer. As indicated in FIG. 18, the flow is not restricted to be unidirectional; rather, the arrows are merely drawn in FIG. 18 to illustrate the various pathways within the implant.

FIG. 19 illustrates various portions of the meniscus of the human knee. It is understood that the area to be irrigated is essentially throughout the meniscal root and extending to the vascular portion of the meniscus.

Figure 15:
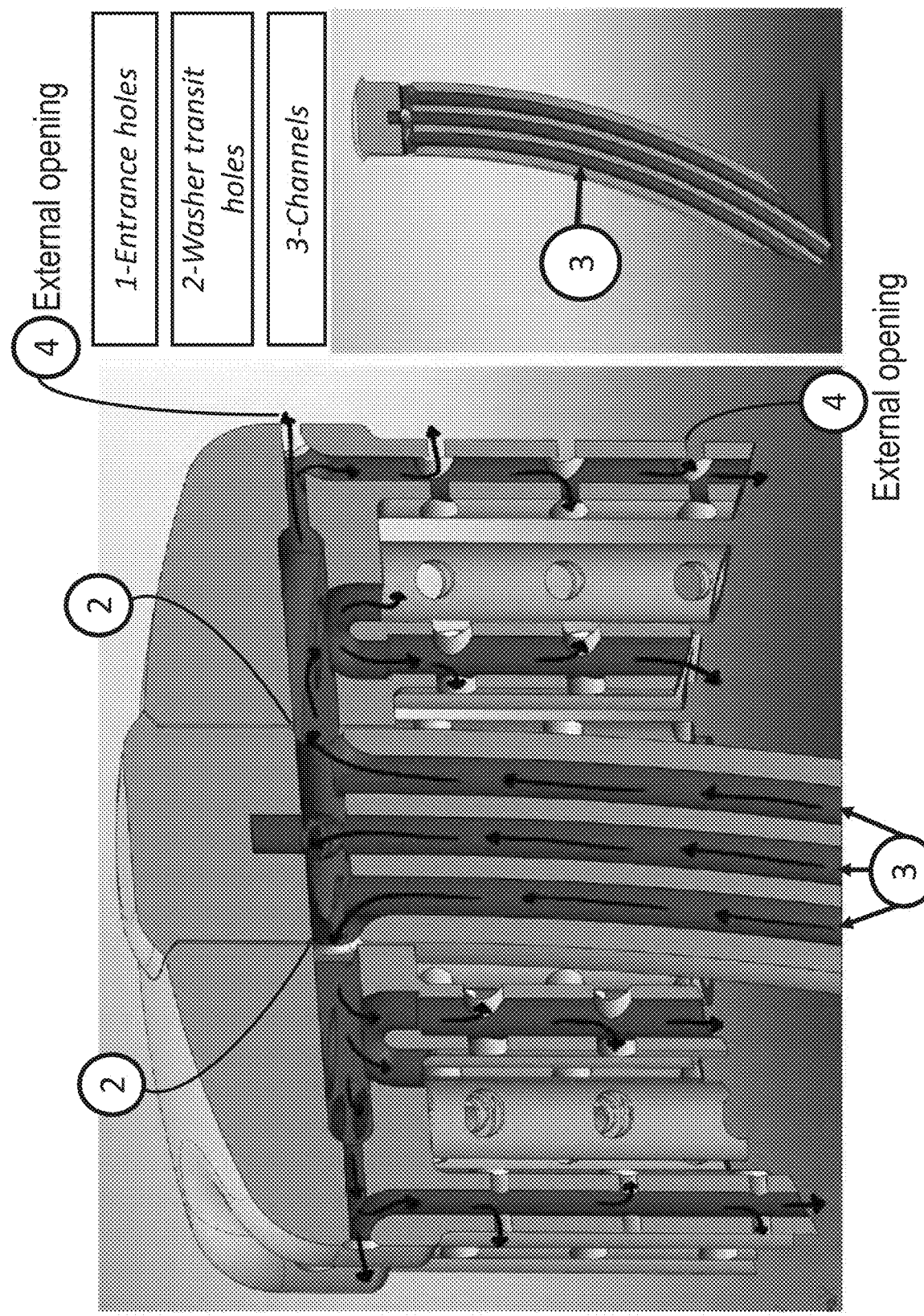
FIG. 15 illustrates exemplary irrigation canals within an example blade and washer combination.
Figure 15A:
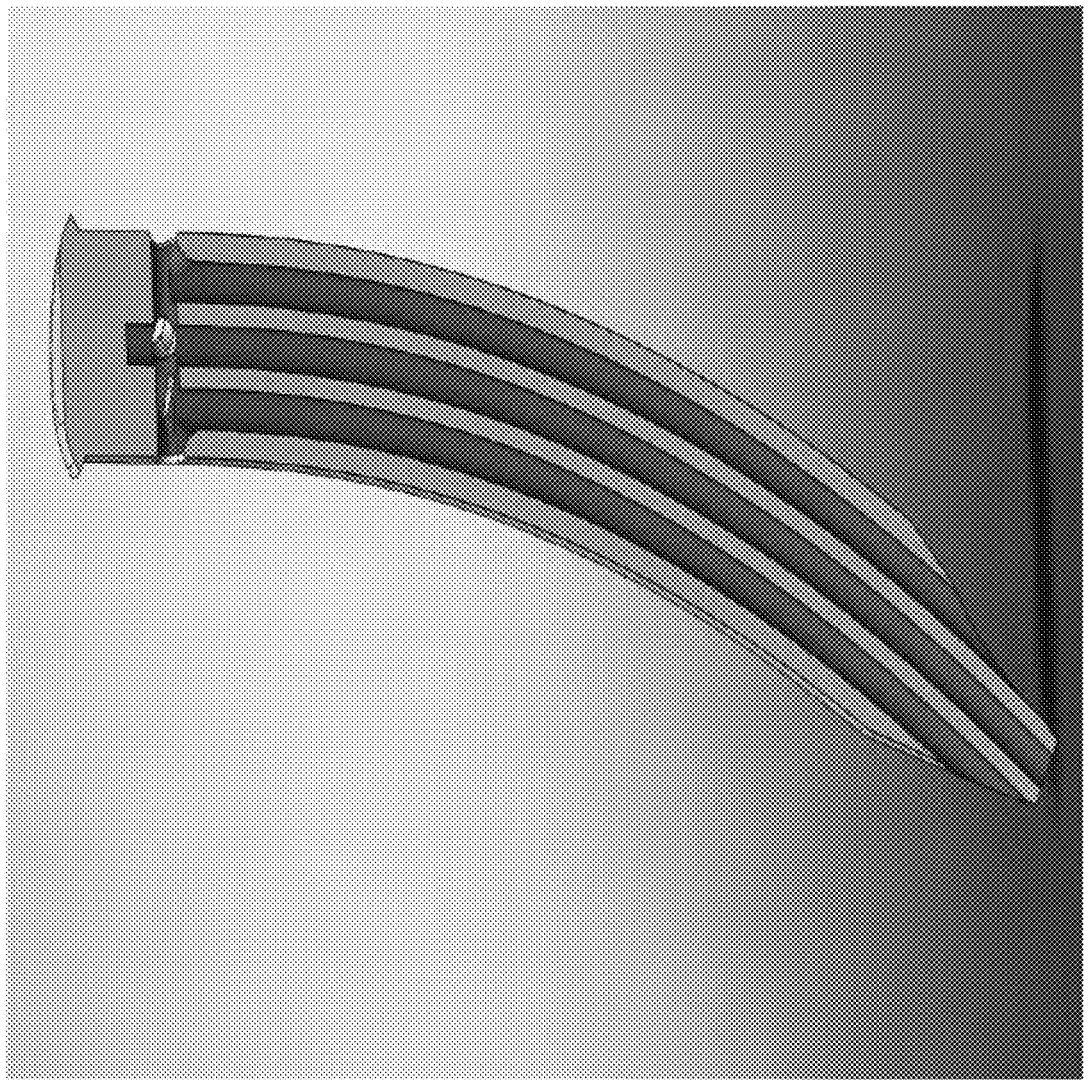
FIG. 15A is a close-up view of the blade of FIG. 15.

FIG. 20 is a duplicate of FIG. 15 with the areas of the knee joint to be irrigated drawn onto the figure. The white or upper portion is the meniscal root and the yellow or lower portion is the bone. It is here noted that in general there is no bright line demarcation between cortical bone and meniscal root. Thus, as shown by the white and yellow areas drawn into the figure, there is a somewhat fuzzy transition zone, and the two tissues may be interdigitated, as shown. Thus, it is into this transition layer (between the white portion 1, and the bone portion 2, that, in embodiments, the lowest irrigation emitters provided on the implant may outflow.

B. Integrated Tack Type Implant Device

Figure 21:
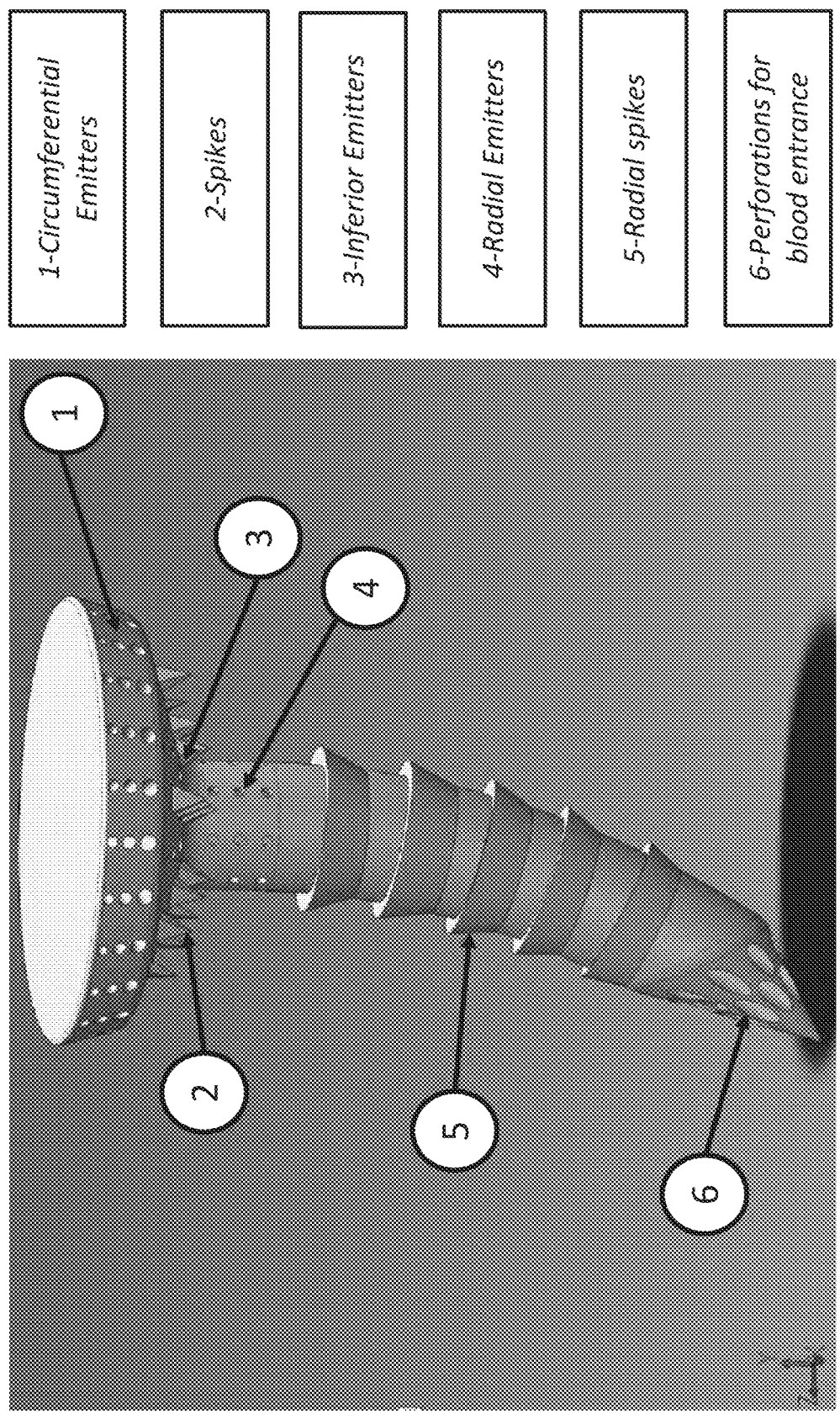
Figure 23:
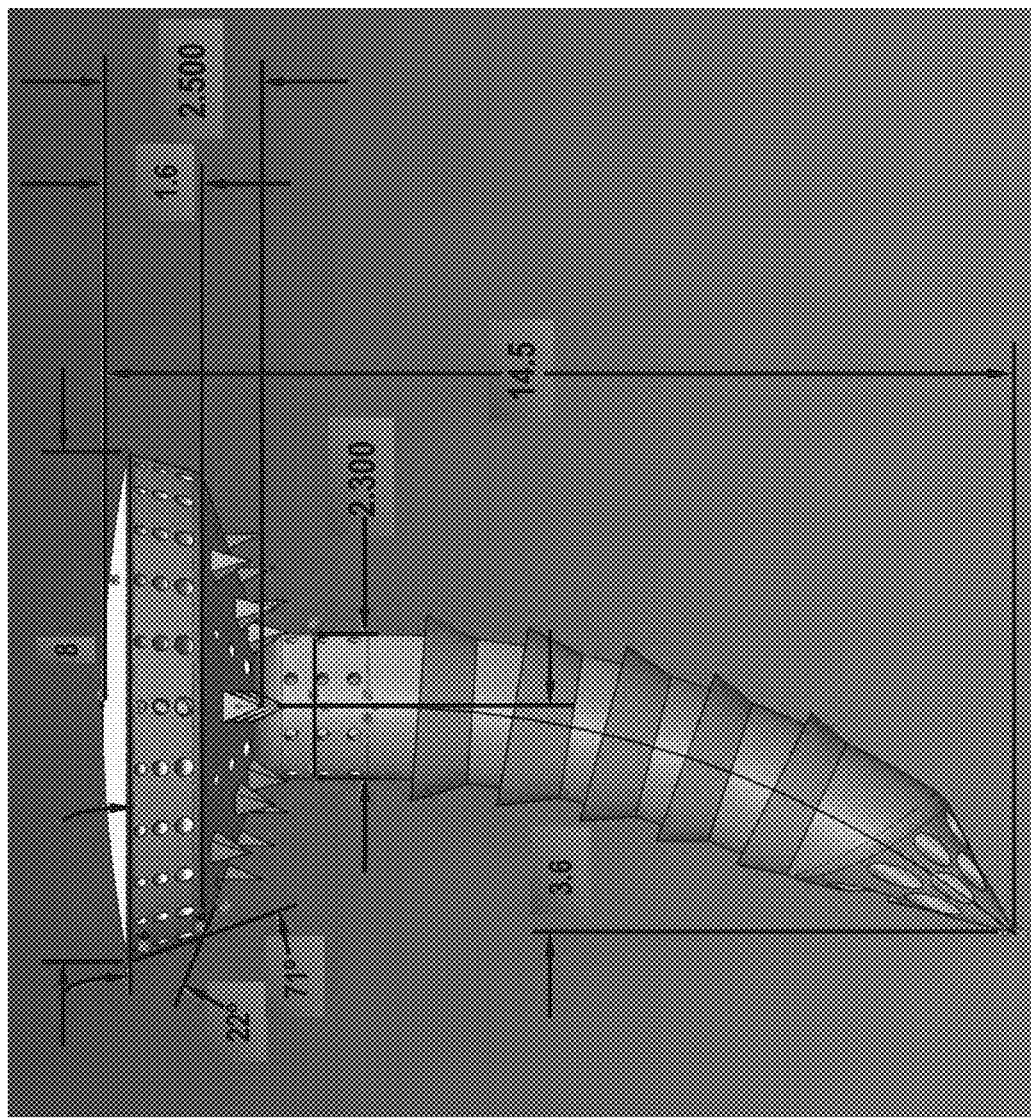

FIGS. 21-23 depict various close-up views of an exemplary tack embodiment in accordance with various embodiments. With reference thereto, referring to FIG. 21, the following elements of the exemplary tack embodiment are shown. It is first noted that the tack embodiment is somewhat different than the combined Blade and Washer embodiment of FIGS. 3-18 and 20. In the tack embodiment of FIGS. 21-23, the emitters are all provided within a relatively larger diameter (relative to the central anchor shaft) "distribution cap" provided at the top or proximal end of the device. Moreover, there are also fewer rows of emitters on the shaft, placed somewhat below the bottom portion of the distributor cap at the proximal end of the exemplary device. Thus, there can be seen in FIG. 21 Circumferential Emitters 1, which are emitters that are provided in a number of rows running up and down the sides of the cap portion of the device. There may also be seen Spikes 2, protruding from the underside of the cap, which may be used to anchor the device, at its upper portion, into the meniscus, the device thereby providing anchoring at both its distal end, by the sharp distal tip of the implant, and at the proximal end via Spikes 2. Also shown in FIG. 21 are Inferior Emitters 3, which are emitters provided on the underside of the cap structure, and Radial Emitters 4, which, as noted, are emitters provided on the proximal portion of the shaft itself. Finally, there may be seen Radial Spikes 5 which, in embodiments, may fix the exemplary tack device into the bone as it is tapped in. It is noted that because of the angle made between the radial spikes and the shaft, it is easy to push the spikes downwards, but once down, they do not allow the device to be easily pulled out. They may thus operate in a ratchet like capacity. Finally, there may be Perforations 6 for blood and nutrient entrance at the tip, or distal end, of the exemplary device.

Figure 24:
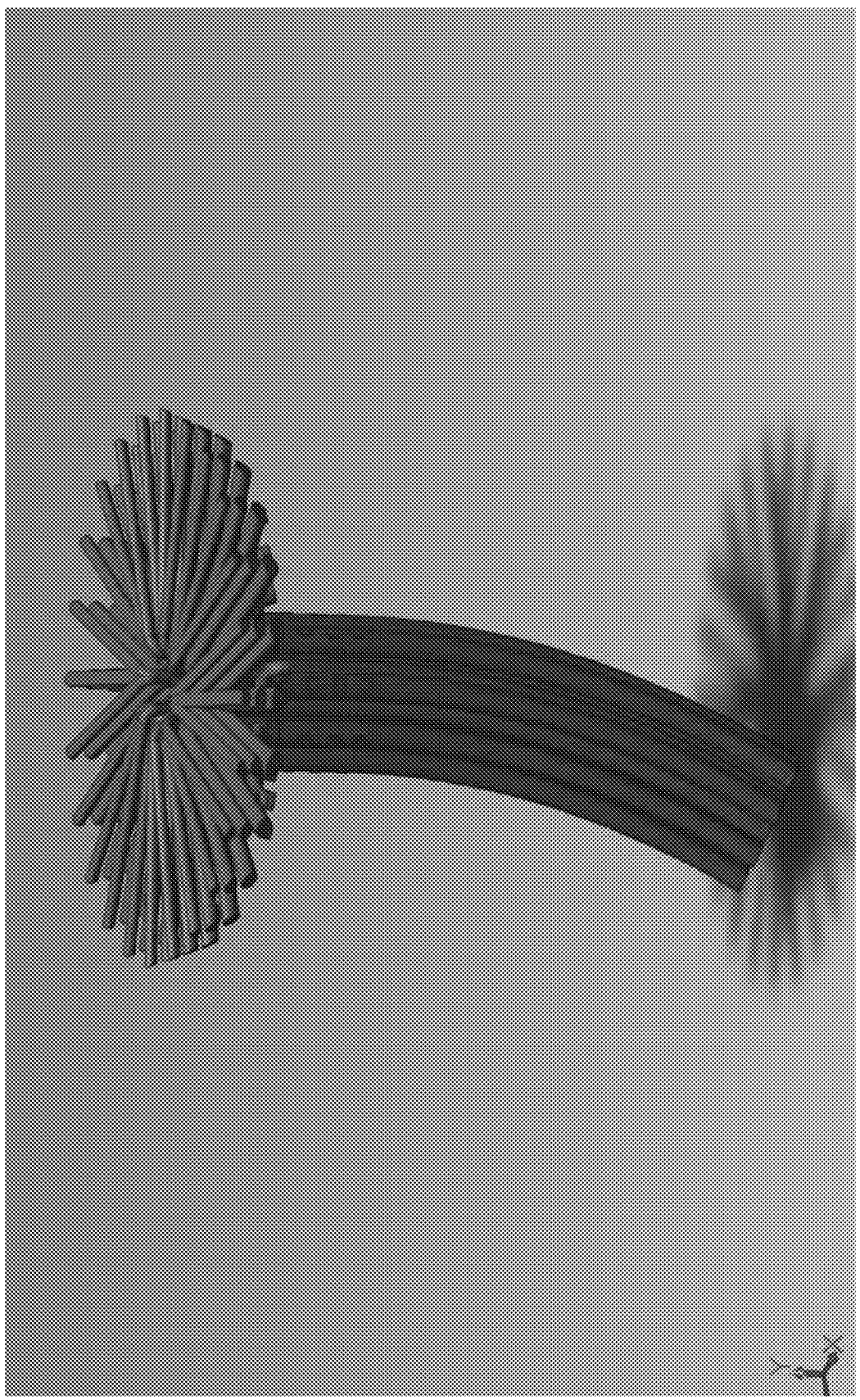
FIG. 24 depicts exemplary irrigation canal pathways of the exemplary tack embodiment of FIGS. 21-23.

FIG. 22 is a front direct view of the device shown in FIG. 21, and the elements are the same as described above with reference to FIG. 21. FIG. 23 provides exemplary dimensions of the exemplary tack device of FIGS. 21 and 22. FIG. 24 shows just the internal irrigation, or fluid flow pathways that may provided within the exemplary tack implant device of FIGS. 21-23.

Referring back to FIG. 23, the exemplary implant device may have an overall length of 14.5 mm, with an outer diameter of 2.3 mm for the central shaft, and where there are fixation ribs (radial spikes), their outer diameter may be 2.6 mm. The curvature of the shaft (or "Blade") may create a 3.6 mm lateral Blade offset, as shown, and the pyramidal spikes provided on the underside of the cap may be 0.65 mm long. The overall diameter of the cap may be 8.0 mm, and it may be 1.6 mm thick, with a dome like upper surface, and sides that are tapered, as is the underside, so as to facilitate smooth transitions as the device is pushed into soft tissue, with no straight lines or completely flat surfaces, either vertically or horizontally, as shown. It is noted here that all dimensions of any exemplary embodiment presented are only illustrative, and not at all limiting. Dimensions may be freely changed both as regards enlarging or making smaller, appropriate in a given anatomical area, for a given patient, or both. It is generally understood, however, that aspect ratios, dimensional relationships between elements, and overall shapes of the exemplary devices will be generally (but not necessarily literally) preserved.

Figure 25:
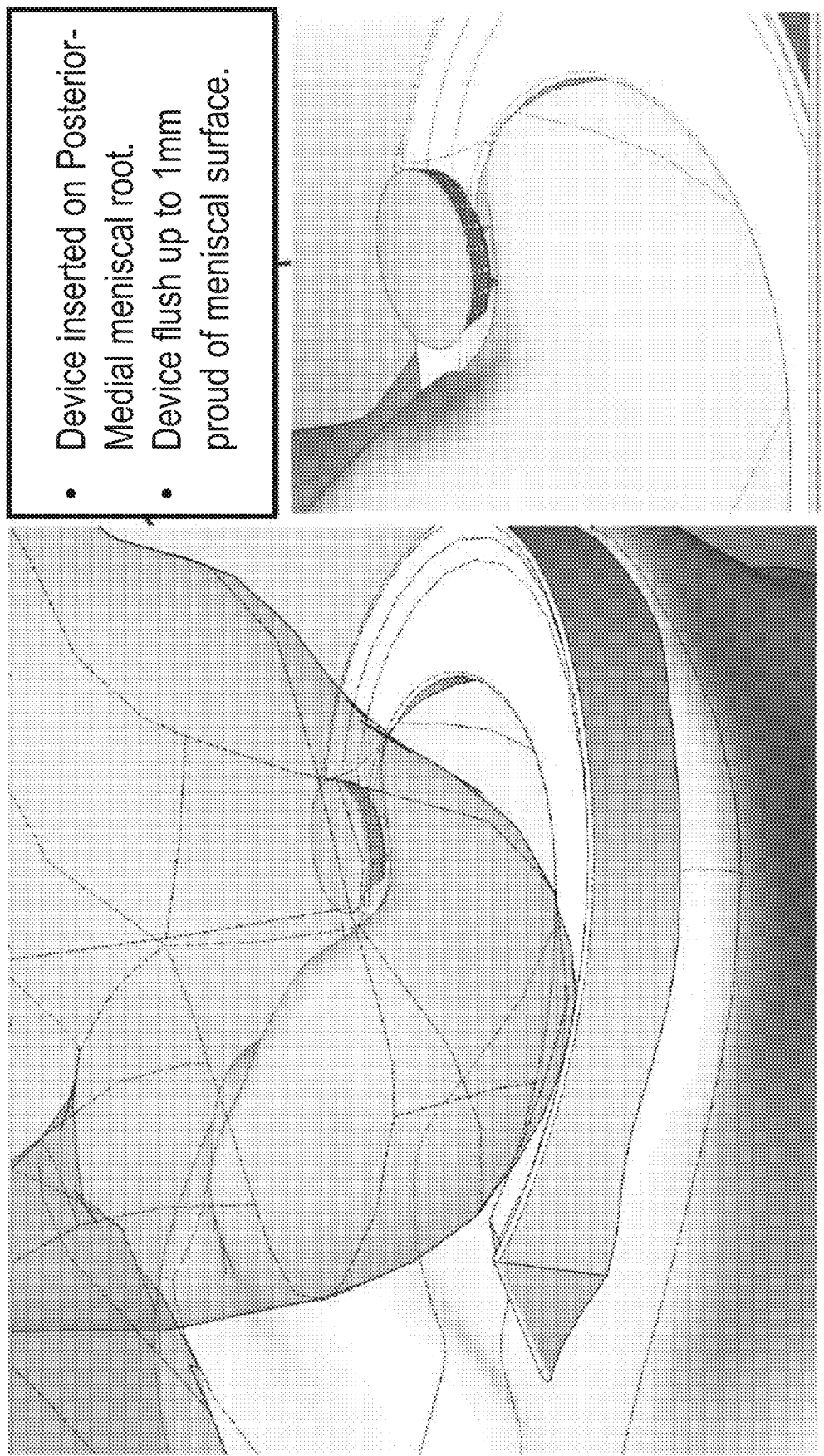
FIG. 25 depicts the exemplary device of FIGS. 21-23 as inserted on a human Posterior-Medial Meniscal root.

FIGS. 25-30 depict an exemplary delivery device pathway used to insert the exemplary tack type implant device according to various embodiments. As shown in FIG. 25, the device may be inserted in the posterior-medial meniscal root, and its final position may be, for example, be flush with the meniscal root (under the articular surface). Alternatively, it may be somewhat "sunk" below the surface of the root. Still alternatively, but less preferably, the implant device may even be up to 1 mm proud of the meniscal surface. FIGS. 25-30 thus show the last steps in inserting the exemplary device, prior to final positioning. FIGS. 26 and 27 show an angle of 60° or less that, in embodiments, may be used to insert the device into a patient from an essentially frontward approach. Thus, FIGS. 26 and 27 show the device progressing through the delivery pathway as it is inserted. FIGS. 28 and 29 are transparent renderings of the same views depicted in FIGS. 26 and 27.

FIG. 30 illustrates the device as almost fully inserted into the meniscus, where, as noted, it should preferably finally sit either flush, or slightly "sunk" relative to the meniscal surface, with the distal tip of the shaft or blade pointed interiorly, as described above in connection with the example "Blade and Washer" embodiment of FIGS. 3-20.

FIG. 31 depicts various views of the exemplary tack device embodiment of FIGS. 21-23 as positioned in a human meniscus showing both the outer contour of the device in a transparent manner and the various irrigation pathways within an example implant.

Figure 32:
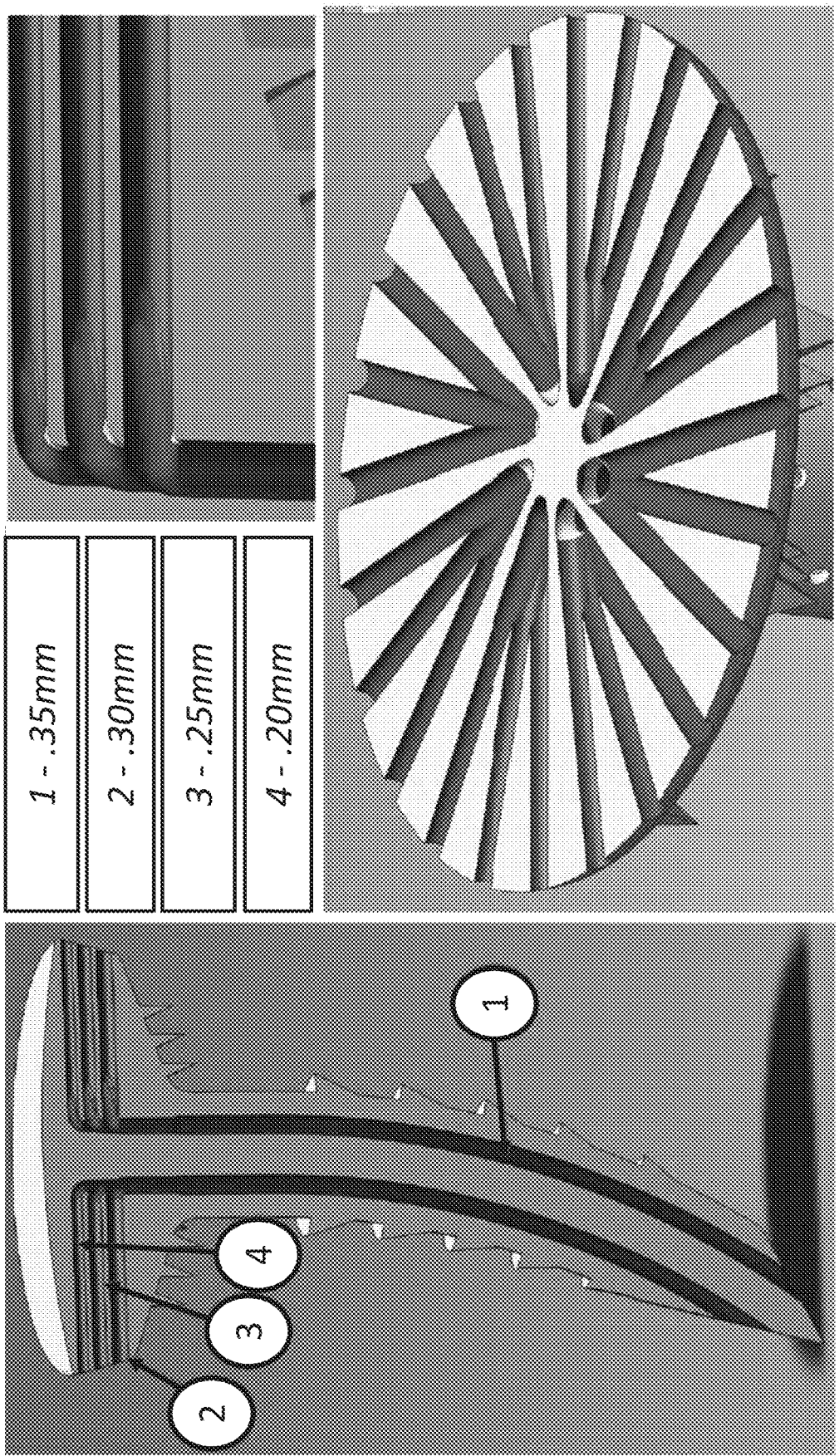
FIGS. 32 and 33 illustrate exemplary inner diameters of the various irrigation pathways of the exemplary tack embodiment of FIGS. 21-23.
Figure 33:
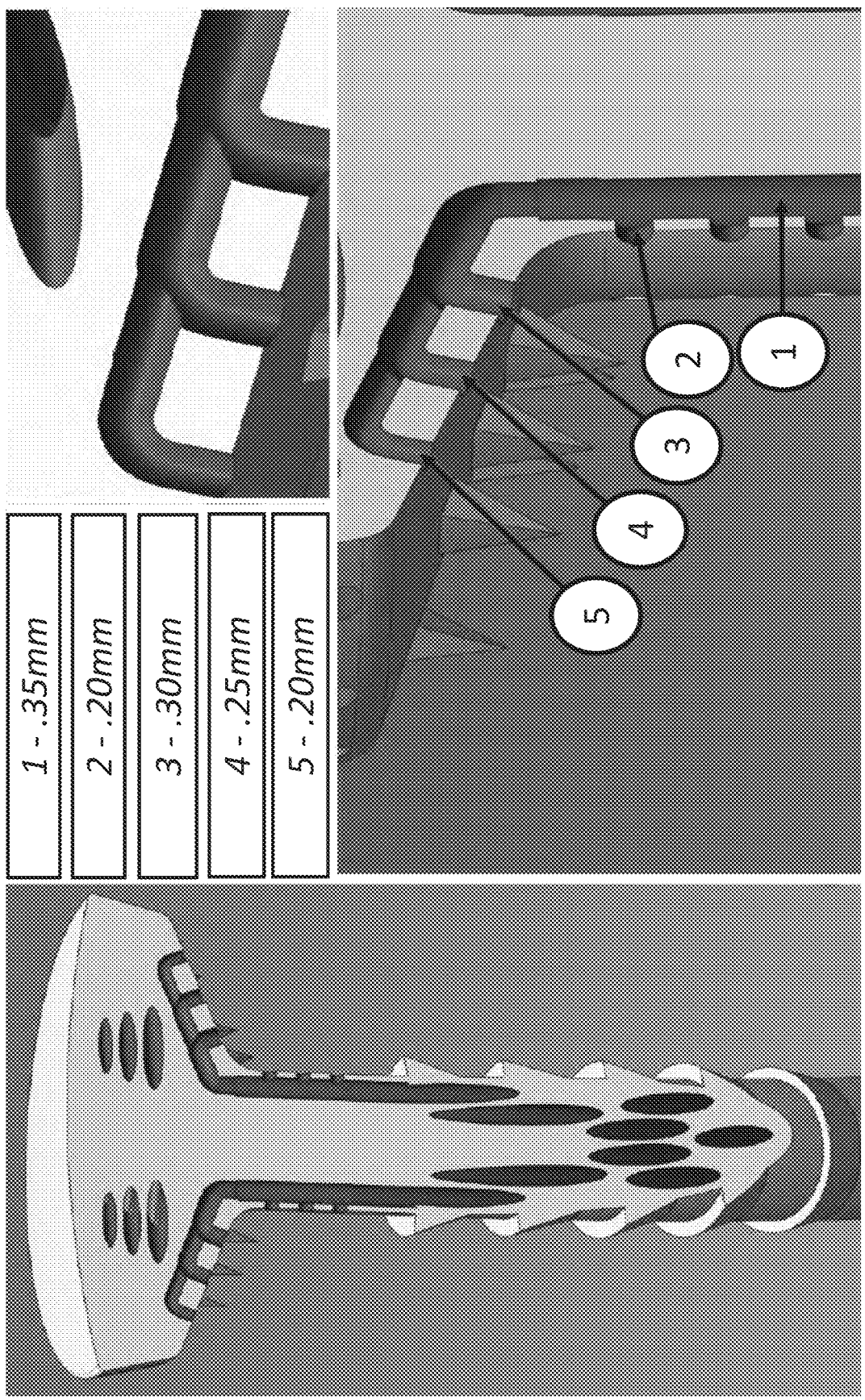

FIGS. 32 and 33 illustrate exemplary inner diameters of the irrigation pathways of the exemplary tack embodiment of FIGS. 21-23. With reference thereto, there may be seen four different diameters used, namely the irrigation pathway from the distal tip of the shaft or blade 1 which may be 0.35 mm, and the horizontally extended pathways 2, 3 and 4 that extend from the center of the shaft out through the distributor cap to the edge, thereby feeding the circumferential emitters. It is noted that the circumferential emitters in this exemplary embodiment may be provided in three different sizes, the lowest level of circumferential emitters 2 having 0.30 mm diameter, a medium layer 3 of 0.35 mm diameter, and an upper layer 4 of 0.2 mm diameter. This scheme allows for the "main vertical pipe" 1 that feeds the various horizontal "local distribution pipes" 2, 3 and 4, to have the greatest flow, and the diameter of each horizontal pipe (and thus its associated circumferential emitter) gets a bit narrower as one proceeds upwards towards the proximal end of the implant device (i.e., the top level of the "distributor cap" structure.) This keeps pressure at the farthest emitter outlets high, in the same sense that in a home plumbing system a bathroom faucet has a smaller source line diameter than that of a kitchen sink or laundry room, and all of such outlets have a smaller diameter than a vertical source line that supplies all of them.

Also seen in FIG. 32 is a horizontal cross section view through one of the layers. To each of said circumferential emitters there may be, for example, assigned one vertical shaft pathway. In this exemplary embodiment there are eight such vertical pathways, each feeding three horizontal circumferential emitters, for a total of 24 circumferential emitters evenly provided around the periphery of the distributor cap, as shown, at each of levels 2, 3 and 4.

FIG. 33 depicts the inferior emitters (identified as Index No. 3 in FIGS. 21 and 22) and also shows radial emitters (identified as Index No. 4 in FIGS. 21 and 22) and the changes in diameter of the inferior emitters as one moves up the underside of the distributor cap proximally of an exemplary implant device. With reference to the bottom right image of FIG. 33, one can see the largest diameter of 0.35 mm belonging to vertical shaft 1, radial emitters on the shaft 2 having the smaller diameter of 0.20 mm, and once the emitters are provided in the underside of the cap, namely the inferior emitters, they come in three sizes, getting smaller as one moves vertically upwards. Therefore, one can see the lowest level of inferior emitters 3 at a diameter of 0.3 mm, the middle layer 4 of inferior emitters at 0.25 mm and the upper row 5 of inferior emitters at a diameter 0.20 mm, which is the same size as the radial emitters on shaft 2.

Figure 34:
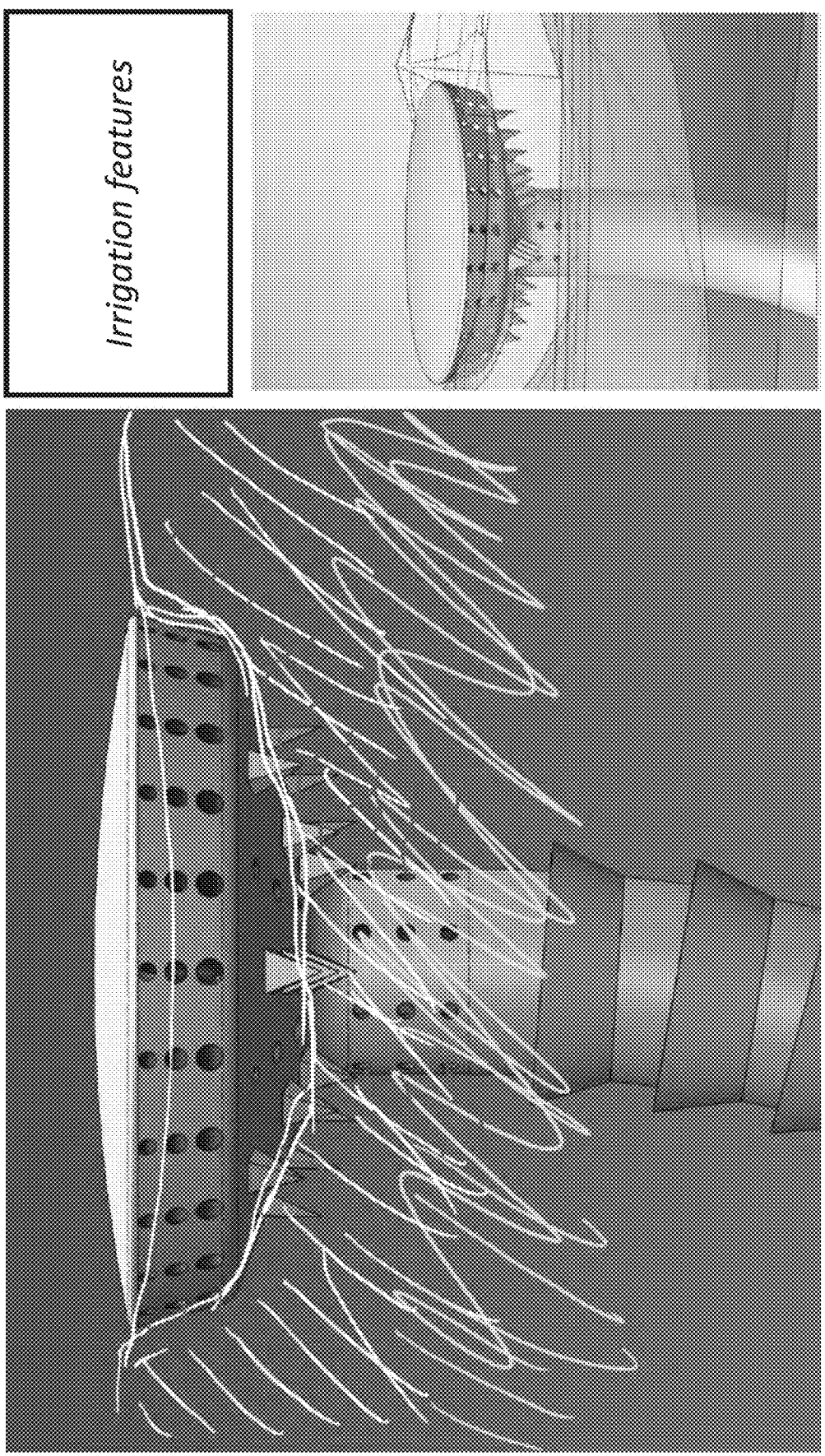
FIG. 34 illustrates the exemplary tack embodiment of FIGS. 21-23 as seated in a meniscus, showing exemplary irrigation outflow pathways.

FIG. 34 illustrates the exemplary tack embodiment of FIGS. 21-23 as seated flush with, and in a meniscus, showing exemplary irrigation pathways (shown by red lines) outside each of the radial emitters, inferior emitters and circumferential emitters, respectively. As described above in connection with FIG. 20, the white, or upper, portion is the meniscal root and the yellow, or lower, portion is the bone.

Figure 35:
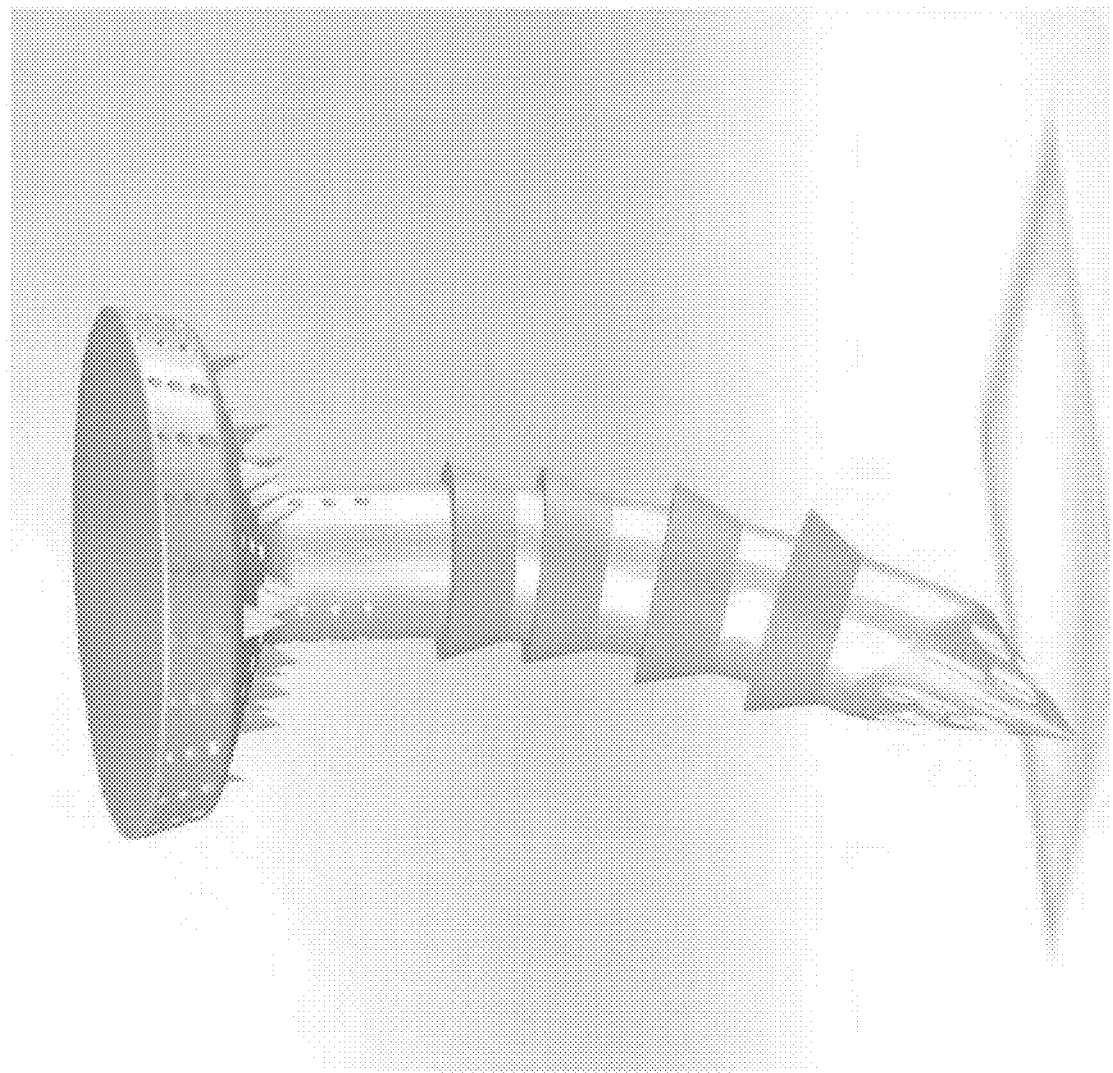
FIG. 35 depicts an outer view of the exemplary tack embodiment of FIGS. 21-23, as provided with radial spikes along the distal portion of the shaft according to an exemplary embodiment of the present invention.

FIG. 35 depicts an outer view of the exemplary tack embodiment of FIG. 21. It is essentially the same view as shown in FIG. 21 from a slightly different perspective.

Figure 36:
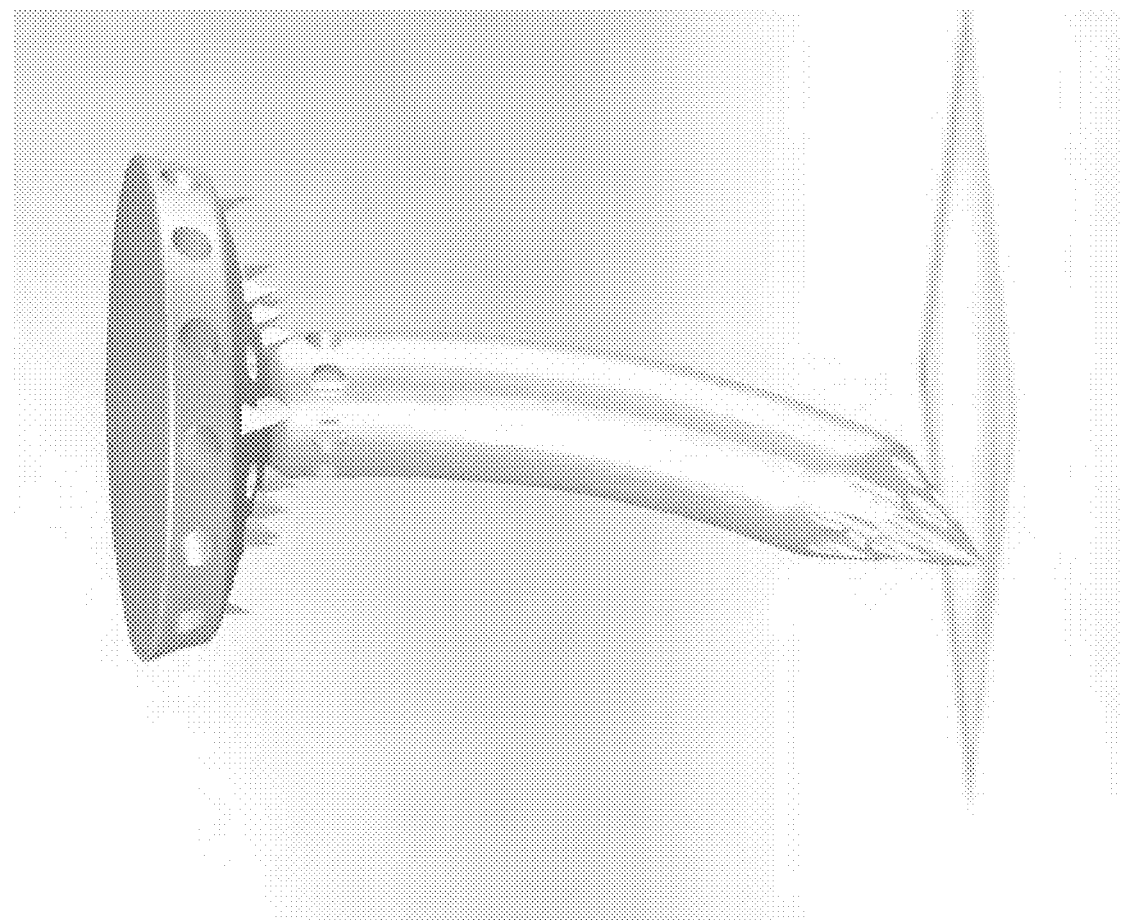
FIG. 36 depicts an outer view of the exemplary tack embodiment of FIGS. 22-26, as provided with a smooth shaft according to exemplary embodiments of the present invention.
Figure 37:
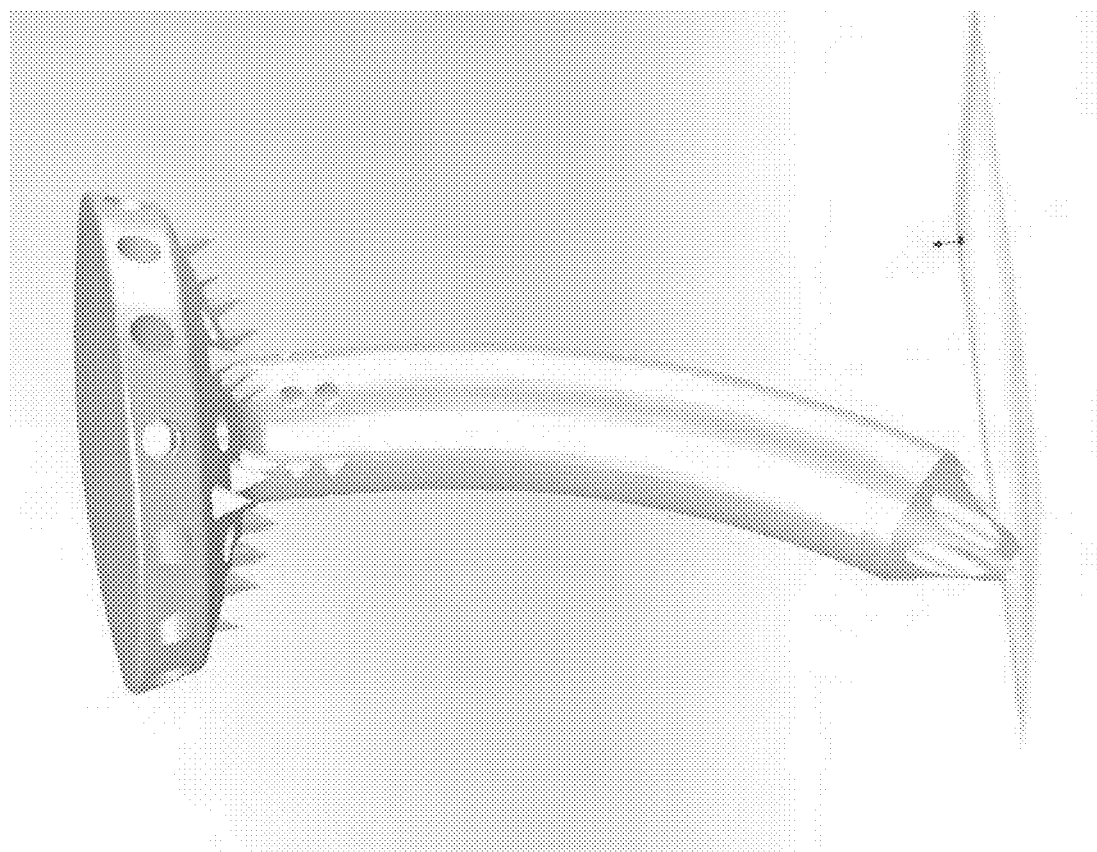
FIG. 37 depicts an alternate version of the tack of FIG. 36, with multiple rows of smaller sized emitter holes.

FIGS. 36 and 37 depict two variations of an embodiment that do not have the radial spikes of FIG. 35, and that also vary in terms of diameters of the various emitters. In FIG. 36 there is one row of radial emitters with a large diameter, and in the variation of FIG. 37 there are multiple rows of radial emitters each having a smaller diameter.

Exemplary Manufacturing Techniques

Figure 38:
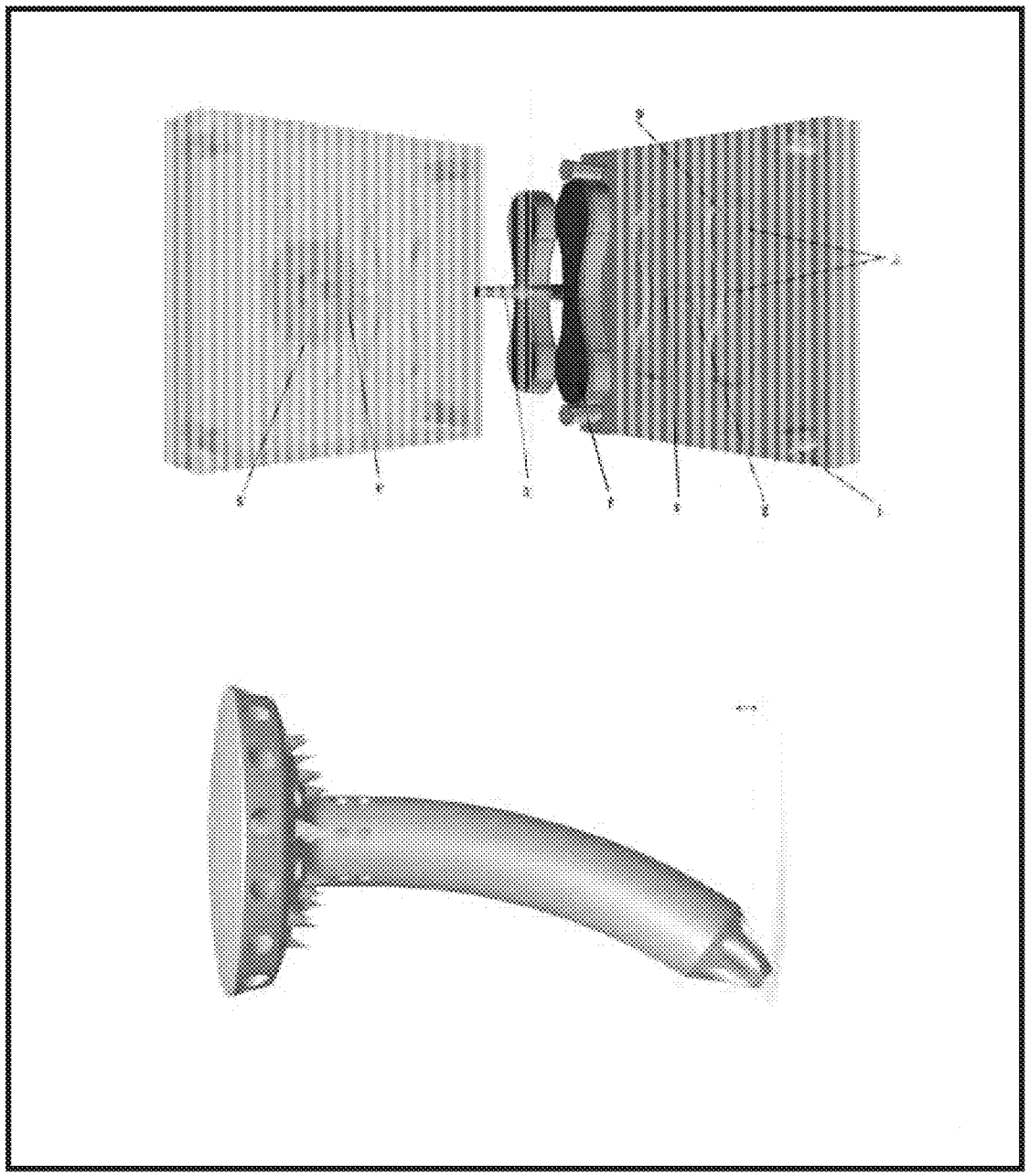
FIG. 38 illustrates exemplary materials and channel sizes using a one piece molded manufacturing process for the exemplary tack embodiment of FIGS. 22-26 made in PEEK.

FIG. 38 illustrates exemplary materials and channel sizes using a one piece molded manufacturing process for the exemplary tack embodiment of FIGS. 21-23 made in PEEK. It is here noted that the benefits of PEEK include, for example, that the process is understood and controllable. An estimated channel size (i.e., the vertical pathways running up the shaft) of 0.5 mm may be used in this embodiment. FIG. 39 illustrates exemplary channel sizes using a micrometal injection molding (micro-MIM) manufacturing process for the exemplary tack embodiment of FIGS. 21-23. It is noted that micro-MIM has the benefit of low cost when many units are made.

FIGS. 40-47, next described, present various exemplary manufacturing processes that may be used to manufacture an exemplary tack type implant device, as shown above. With reference to each of FIGS. 40-47, each manufacturing process is presented along with the estimated channel size that may be created using it, as well as with the benefits and challenges of using such a manufacturing process.

Figure 40:
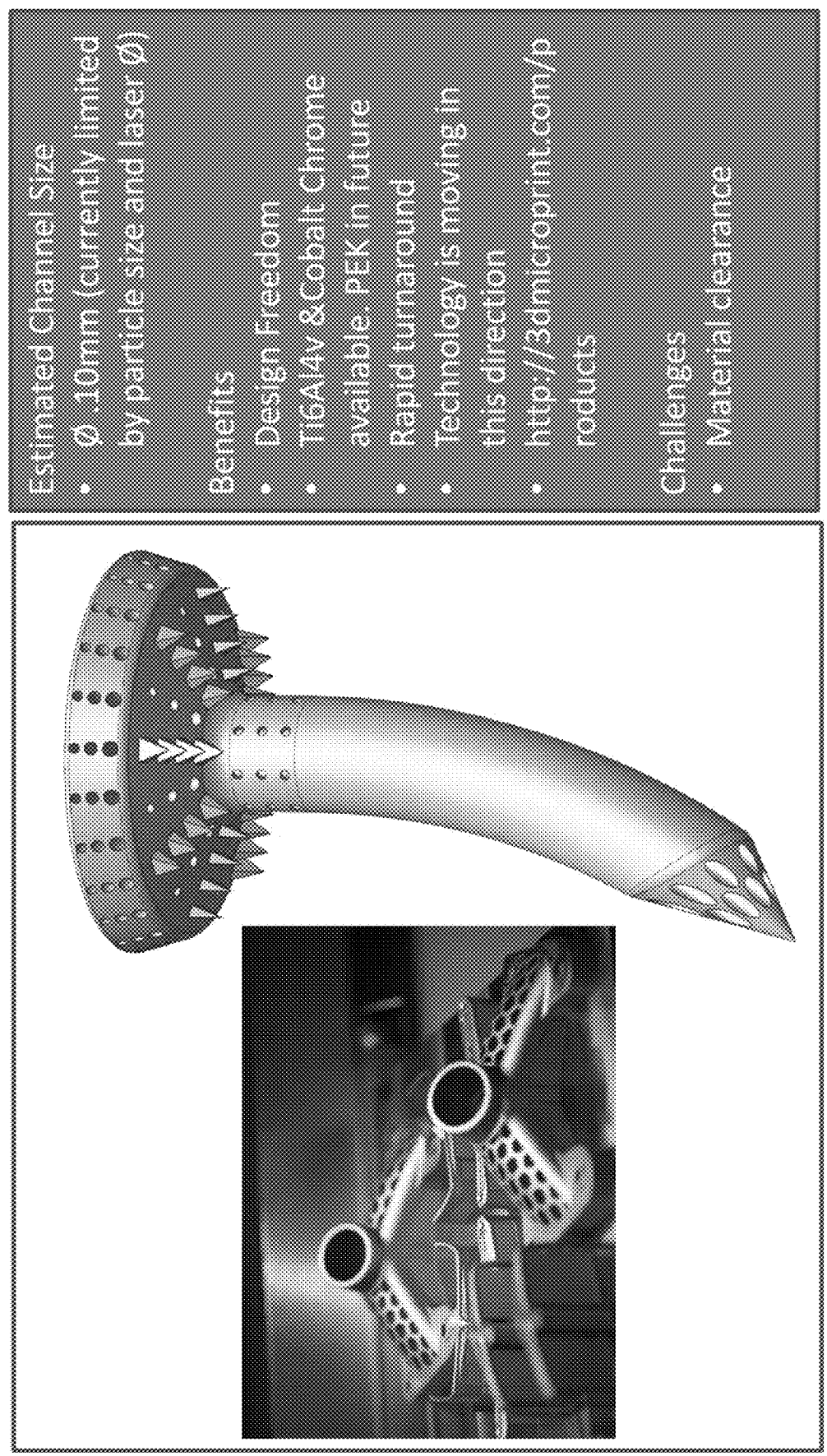
FIG. 40 illustrates exemplary materials and channel sizes using an additive manufacturing process for the exemplary tack embodiment of FIGS. 21-23.

FIG. 40 illustrates exemplary materials and channel sizes using an additive manufacturing process for the exemplary tack embodiment of FIGS. 21-23, as well as benefits and challenges of this manufacturing process.

Its estimated channel size, benefits and challenges are as provided below.

Estimated Channel Size

Ø0.10 mm (currently limited by particle size and laser Ø)

Benefits

Design Freedom

Ti6Al4v & Cobalt Chrome available. PEK in future Rapid turnaround

Technology is moving in this direction http://3dmicroprint.com/products

Challenges

Figure 41:
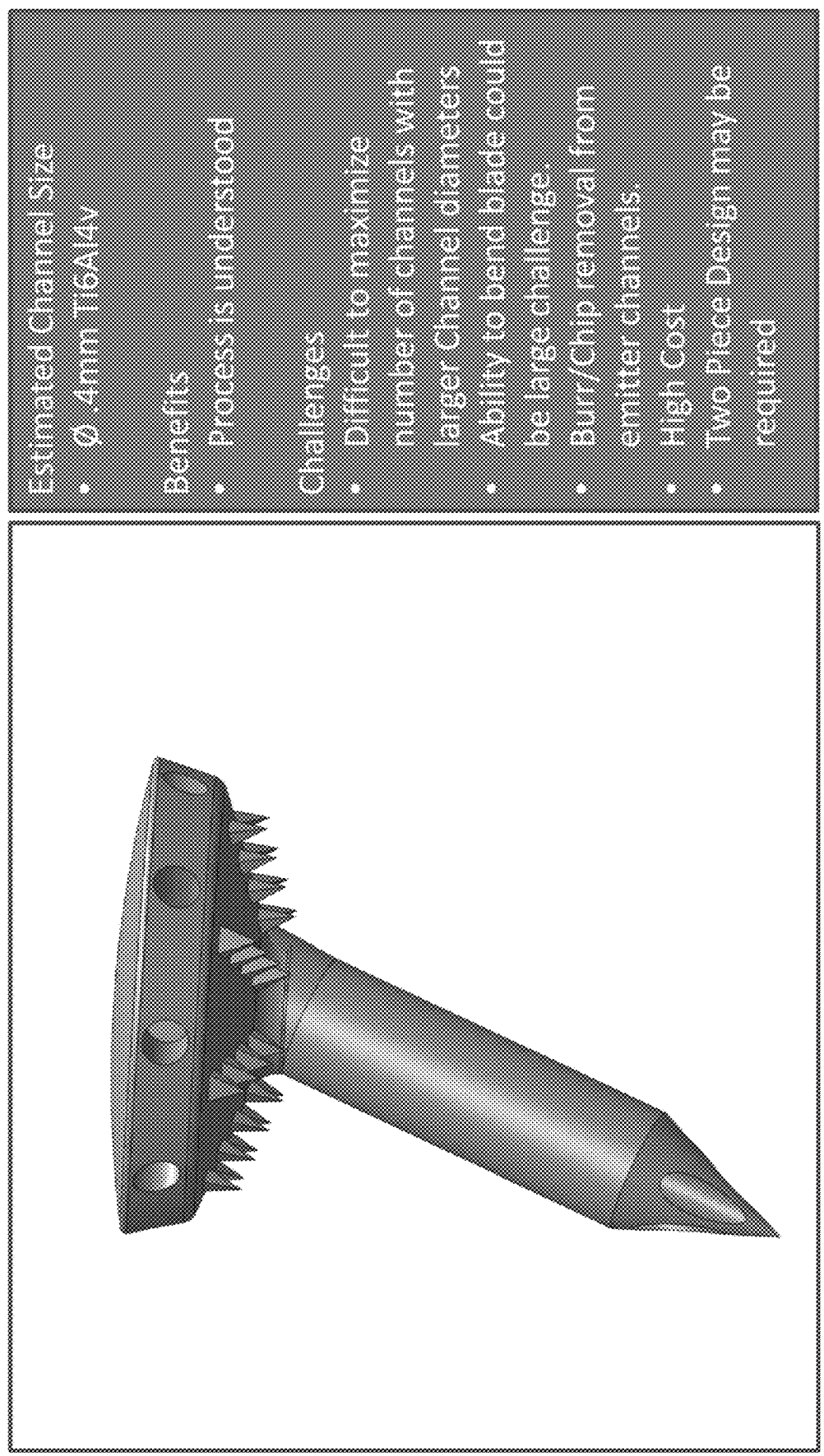
FIG. 41 illustrates exemplary materials and channel sizes using a conventional standard machining manufacturing process for the exemplary tack embodiment of FIGS. 21-23 made in titanium alloy.

Material clearance FIG. 41 illustrates exemplary materials and channel sizes using a conventional standard machining manufacturing process for the exemplary tack embodiment of FIGS. 21-23, made in a titanium alloy. Its estimated channel size, benefits and challenges are as provided below.

Estimated Channel Size

Ø 0.4 mm Ti6Al4v

Benefits

Process is understood

Challenges

Difficult to maximize number of channels with larger Channel diameters

Ability to bend blade could be large challenge.

Burr/Chip removal from emitter channels.

High Cost

Two Piece Design may be required

Figure 42:
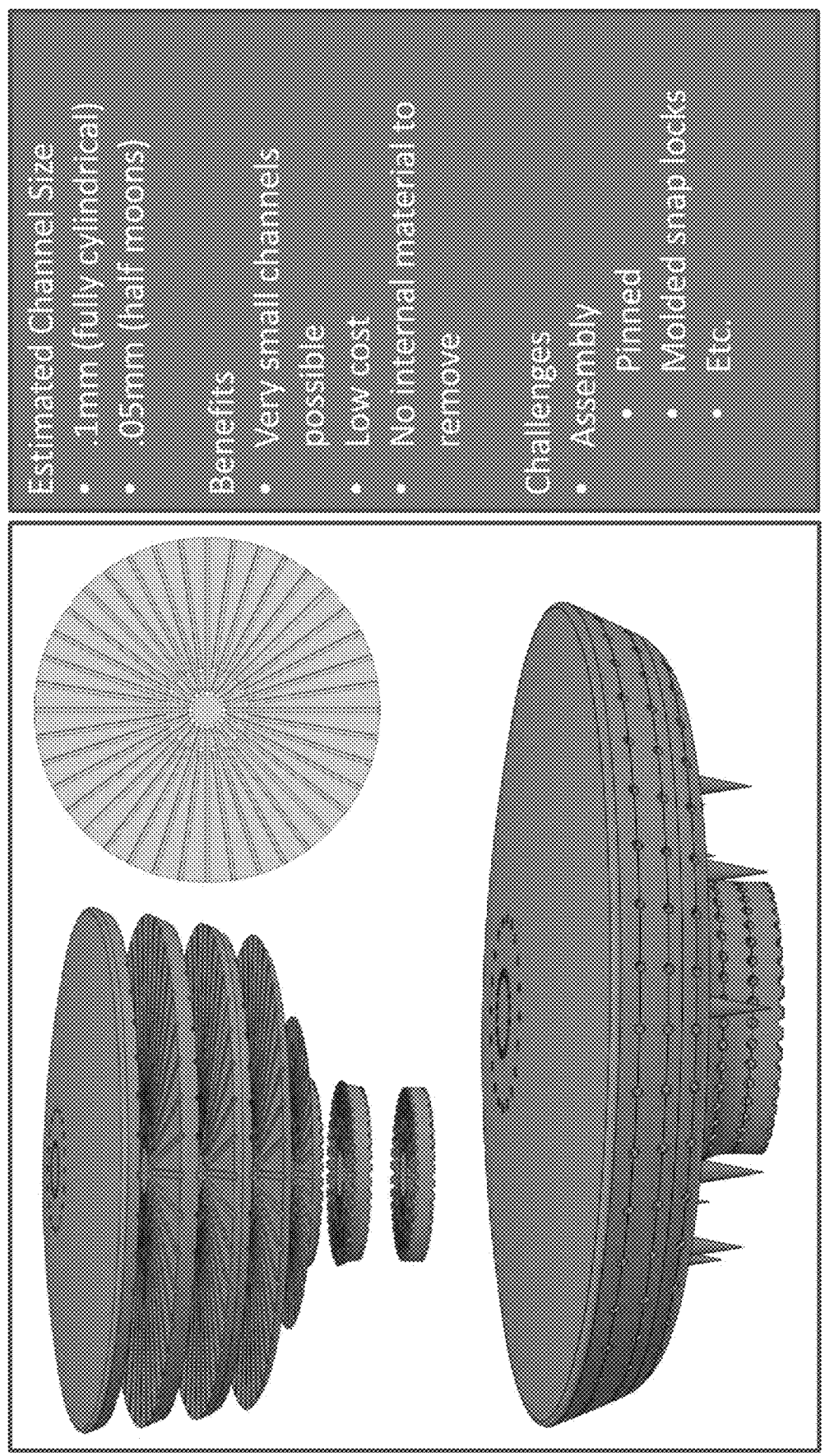
FIG. 42 illustrates exemplary materials and channel sizes using a multiple piece molded manufacturing process ("molded discs") for the exemplary tack embodiment of FIGS. 21-23.

FIG. 42 illustrates exemplary materials and channel sizes using a multiple piece molded manufacturing process ("molded discs") for the exemplary tack embodiment of FIGS. 21-23. Its estimated channel size, benefits and challenges are as provided below.

Estimated Channel Size 0.1 mm (fully cylindrical)

0.05 mm (half moons)

Benefits

Very small channels possible

Low cost

No internal material to remove

Challenges

Assembly

Pinned

Molded snap locks

Etc.

Figure 43:
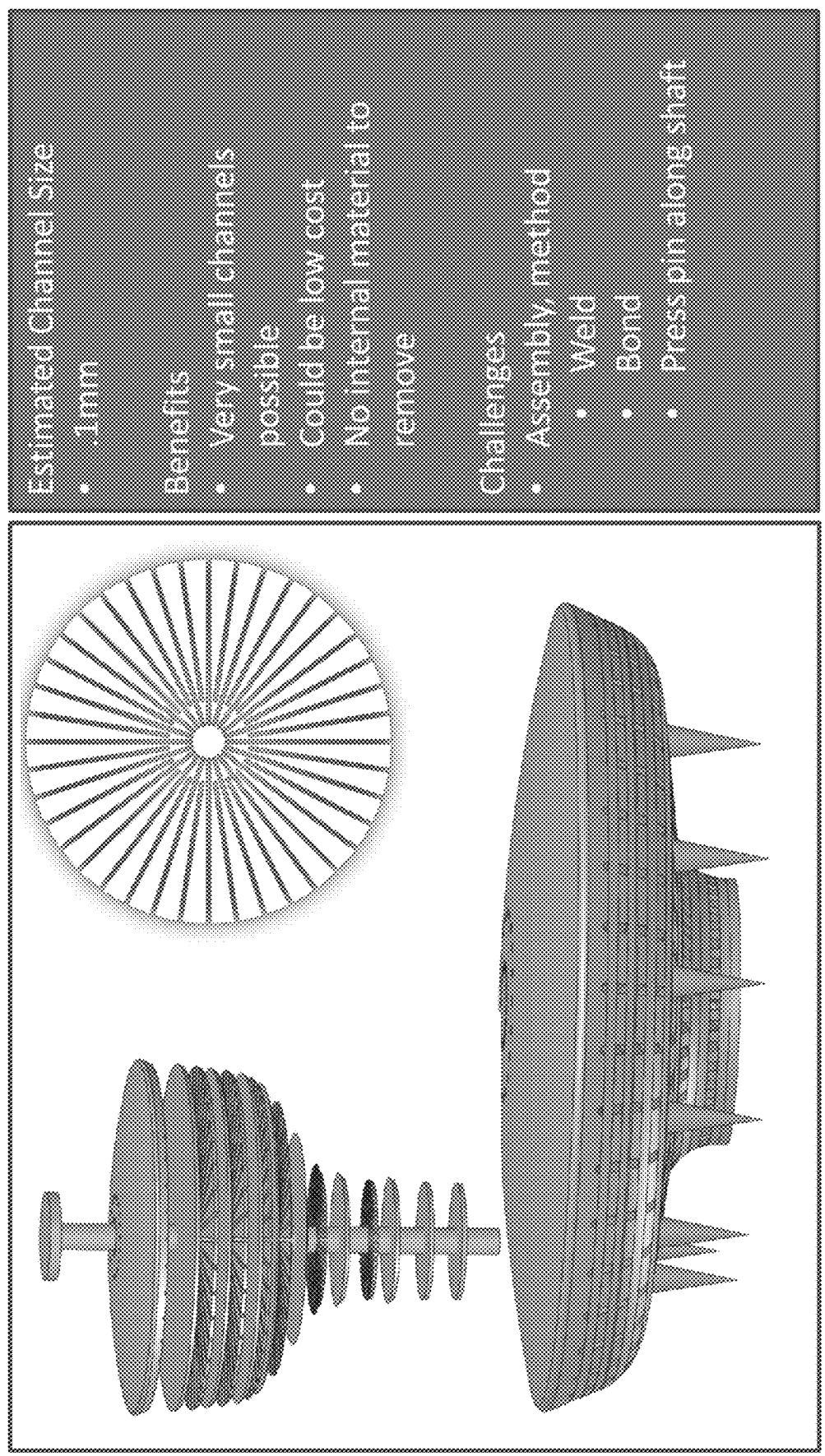
FIG. 43 illustrates exemplary materials and channel sizes using a laser cut sheet manufacturing process ("laser cut discs") for the exemplary tack embodiment of FIGS. 21-23.

FIG. 43 illustrates exemplary materials and channel sizes using a laser cut sheet manufacturing process ("laser cut discs") for the exemplary tack embodiment of FIGS. 21-23. Its estimated channel size, benefits and challenges are as provided below.

Estimated Channel Size 0.1 mm

Benefits

Figure 44:
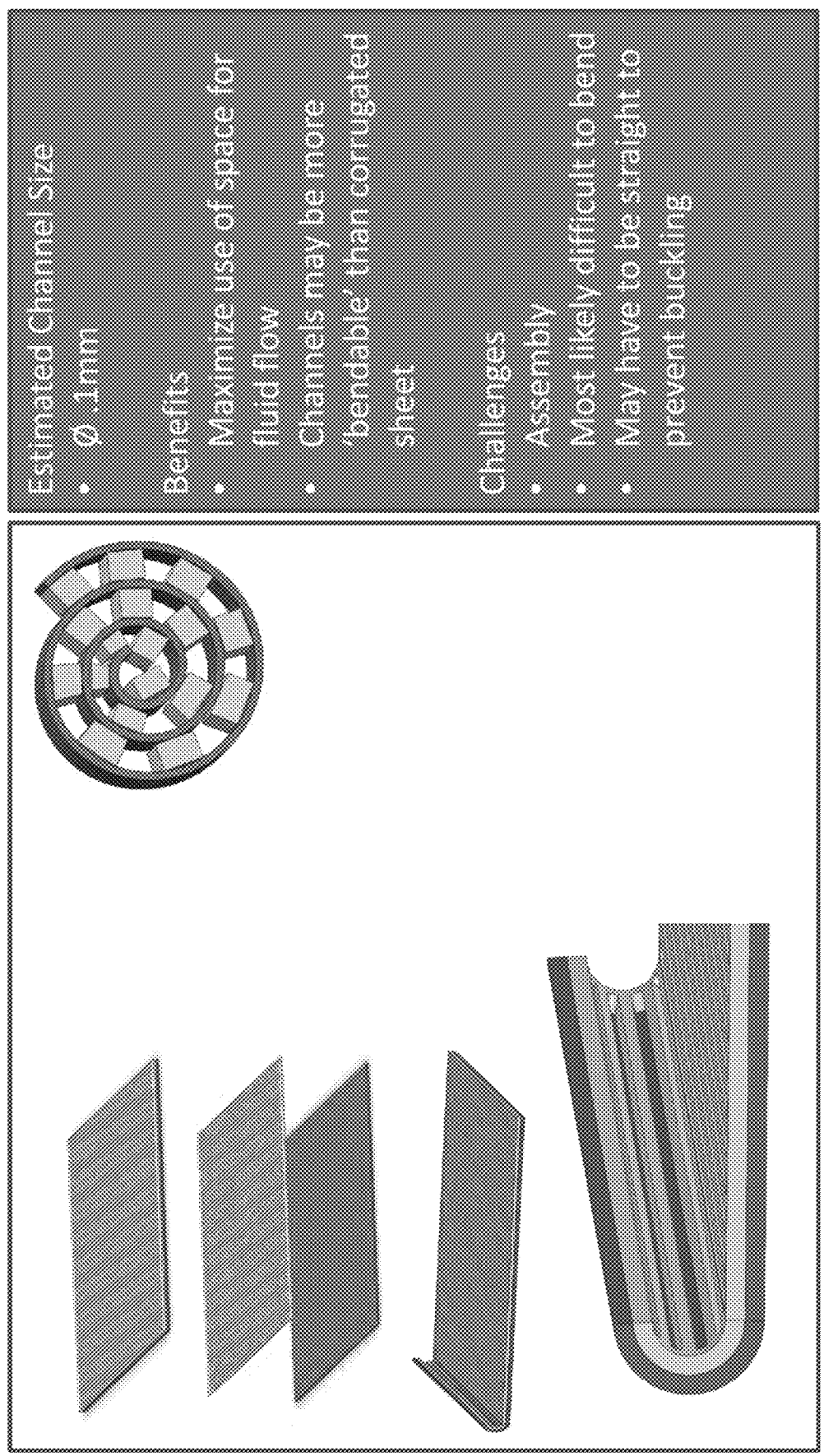
FIG. 44 illustrates exemplary materials and channel sizes using a laser cut sheet metal manufacturing process for the exemplary tack embodiment of FIGS. 21-23.
Figure 46:
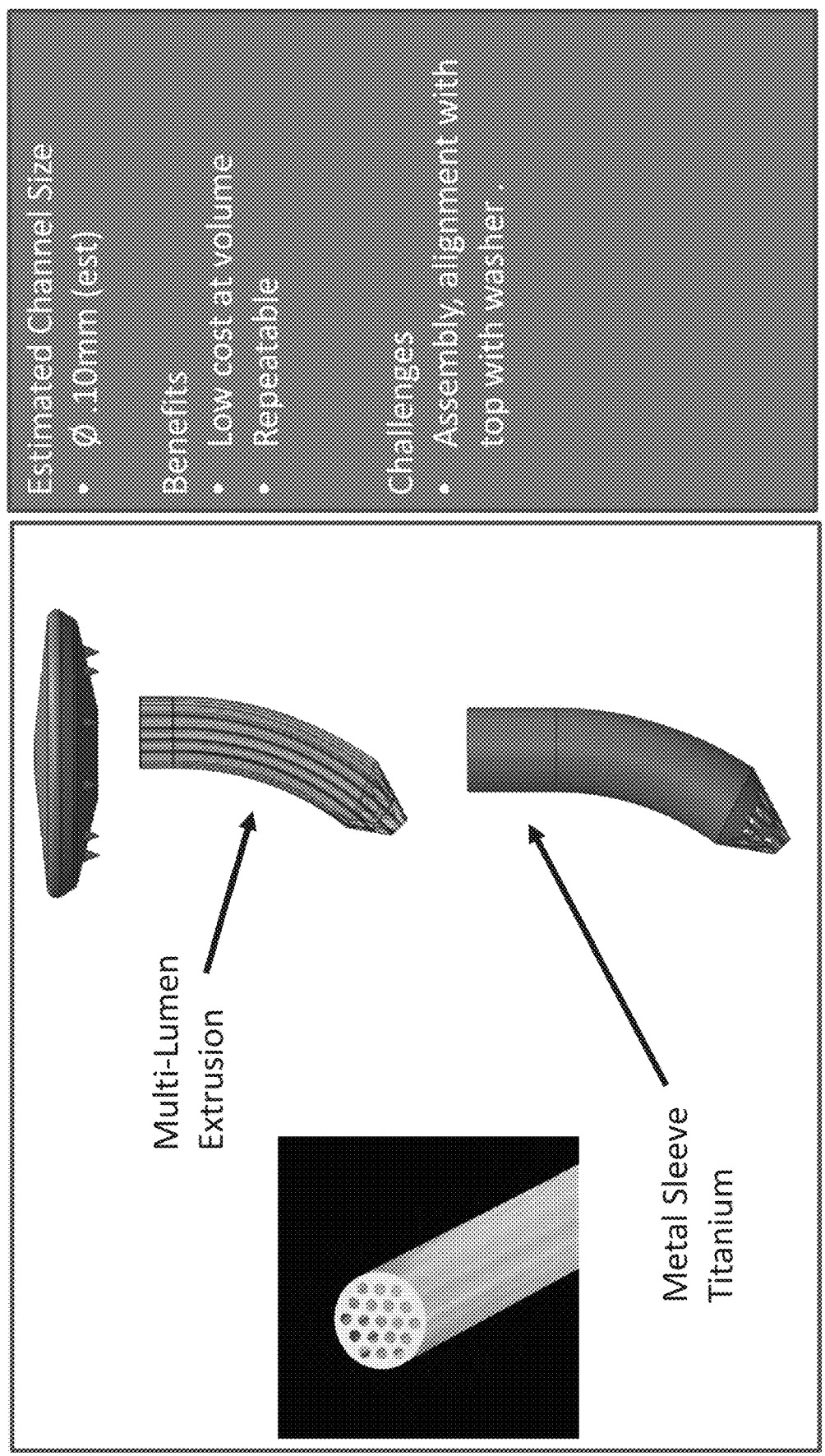
FIG. 46 illustrates exemplary materials and channel sizes using a multi-lumen extrusion manufacturing process for the exemplary tack embodiment of FIGS. 21-23.

Very small channels possible
Could be low cost
No internal material to remove
Challenges
Assembly, method
   Weld
   Bond
   Press pin along shaft FIG. 44 illustrates exemplary materials and channel sizes using a laser cut sheet metal manufacturing process for the exemplary tack embodiment of FIGS. 21-23. Its estimated channel size, benefits and challenges are as provided below.
Estimated Channel Size
0.1 mm
Benefits
Maximize use of space for fluid flow
Channels may be more 'bendable' than corrugated sheet
Challenges
Assembly
Most likely difficult to bend
May have to be straight to prevent buckling FIG. 45 illustrates exemplary materials and channel sizes using a corrugated sheet metal manufacturing process for the exemplary tack embodiment of FIGS. 21-23. Its estimated channel size, benefits and challenges are as provided below.
Estimated Channel Size
0.4 m
Benefits
Maximize use of space for fluid flow
Challenges
New manufacturing process
Multiple piece assembly
Cannot be bent, channels would start at base of shaft FIG. 46 illustrates exemplary materials and channel sizes using a multi-lumen extrusions manufacturing process for the exemplary tack embodiment of FIGS. 21-23. Its estimated channel size, benefits and challenges are as provided below.
Estimated Channel Size
0.10 mm (est)
Benefits
Low cost at volume
Repeatable
Challenges
Assembly, alignment with top with washer Finally, FIG. 47 illustrates exemplary materials and channel sizes using a single lumen extrusions manufacturing process for the exemplary tack embodiment of FIGS. 21-23. Its estimated channel size, benefits and challenges are as provided below.
Estimated Channel Size
0.10 mm (est)
Benefits
Low cost at volume
Repeatable
Challenges
Assembly, alignment with top Table A below summarizes the information presented above with reference to FIGS. 40-47, as to each of the exemplary methods that may be used to manufacture an exemplary implant device, in accordance with various embodiments.

TABLE A

| Manufacturing Process | Channel ø | Primary Benefit | Greatest Challenge |
|---|---|---|---|
| Standard Machining | 0.4 mm | Understood Process | Channel Diameter |
| 1 Piece Molded | 0.5 mm | Cost | Channel Diameter |
| Multi-Piece Molded | 0.1 mm | Cost | Assembly |
| Corrugated Sheet | 0.5 mm | High channel density | Assembly |
| Laser Cut Sheet | 0.1 mm | High channel density | Assembly |
| DMLS | 0.3 mm | Design Flexibility | Channel Diameter |
| MIS | 0.3 mm | Design Flexibility | Channel Diameter |
| 1-piece Extruded | 0.1 mm | Controllable Lumens | Multi-Piece Construction |
| Multi-piece Extruded | 0.1 mm | Controllable Lumens | Multi-Piece Construction |

C. Anchoring Details

Figure 48:
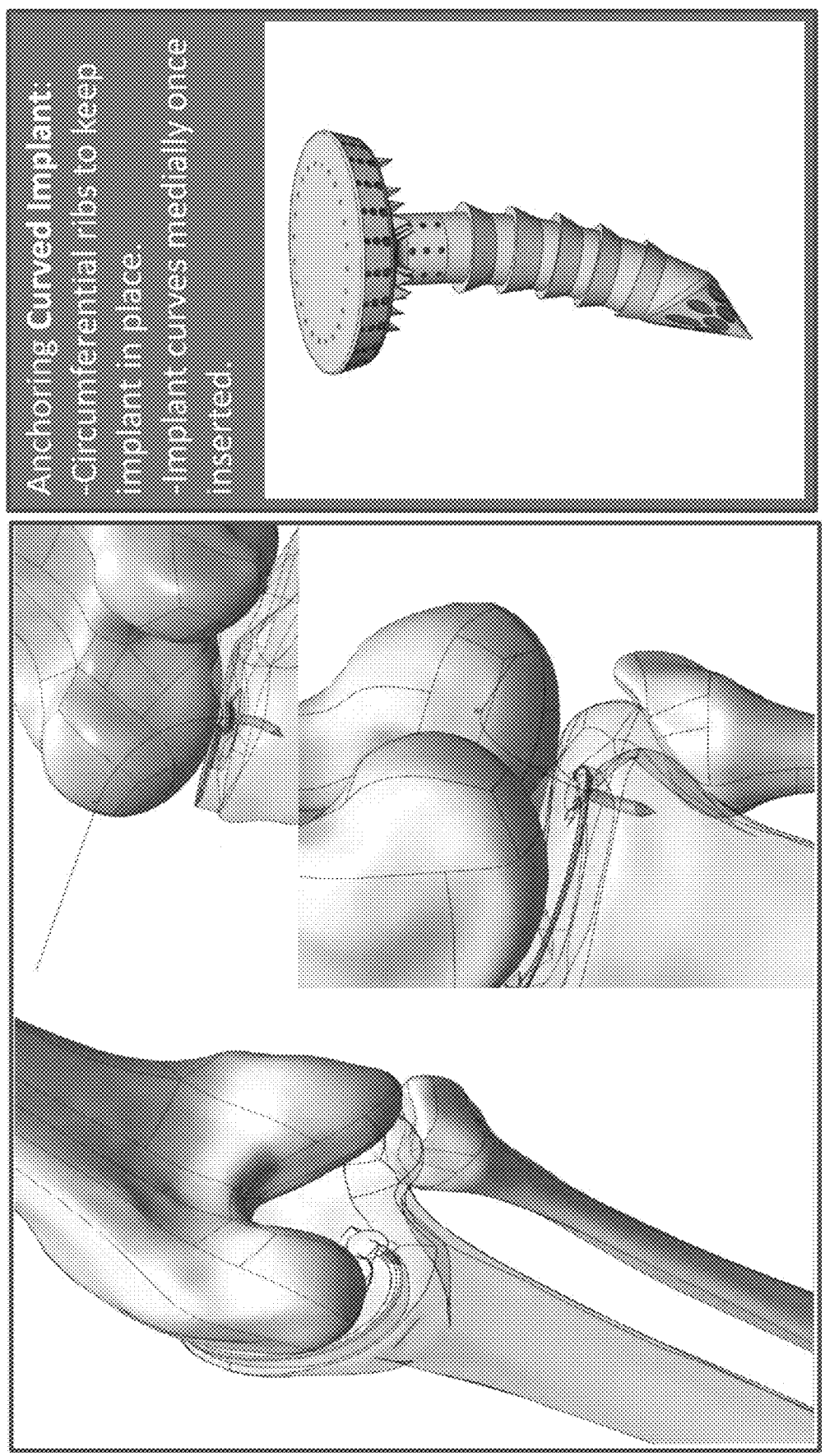
FIG. 48 illustrates anchoring of an exemplary curved tack device by insertion from a posterior medial angle according to an exemplary embodiment of the present invention.

FIGS. 48-58, next described, depict various alternatives and design considerations for anchoring exemplary implant devices in accordance with various embodiments. Thus, FIG. 48 illustrates how an example tack implant with curved shaft may be anchored in accordance with various embodiments. As described above, circumferential ribs (also referred to as "radial spikes" in, for example, FIG. 21), operating in a ratchet-like manner, may be used to fix the implant in place. It is also noted that, in embodiments, once it is inserted, the implant may curve medially.

Depending, of course, on the approach a given surgeon may use to insert an exemplary implant, the implant may curve anteriorly, or anterior-medially, as may be most appropriate in a given implementation. Possible approaches are anterior, as well as the preferred post medial, as described below. As also noted above, in general, it is not desirable for the implant to curve posteriorly.

Figure 49:
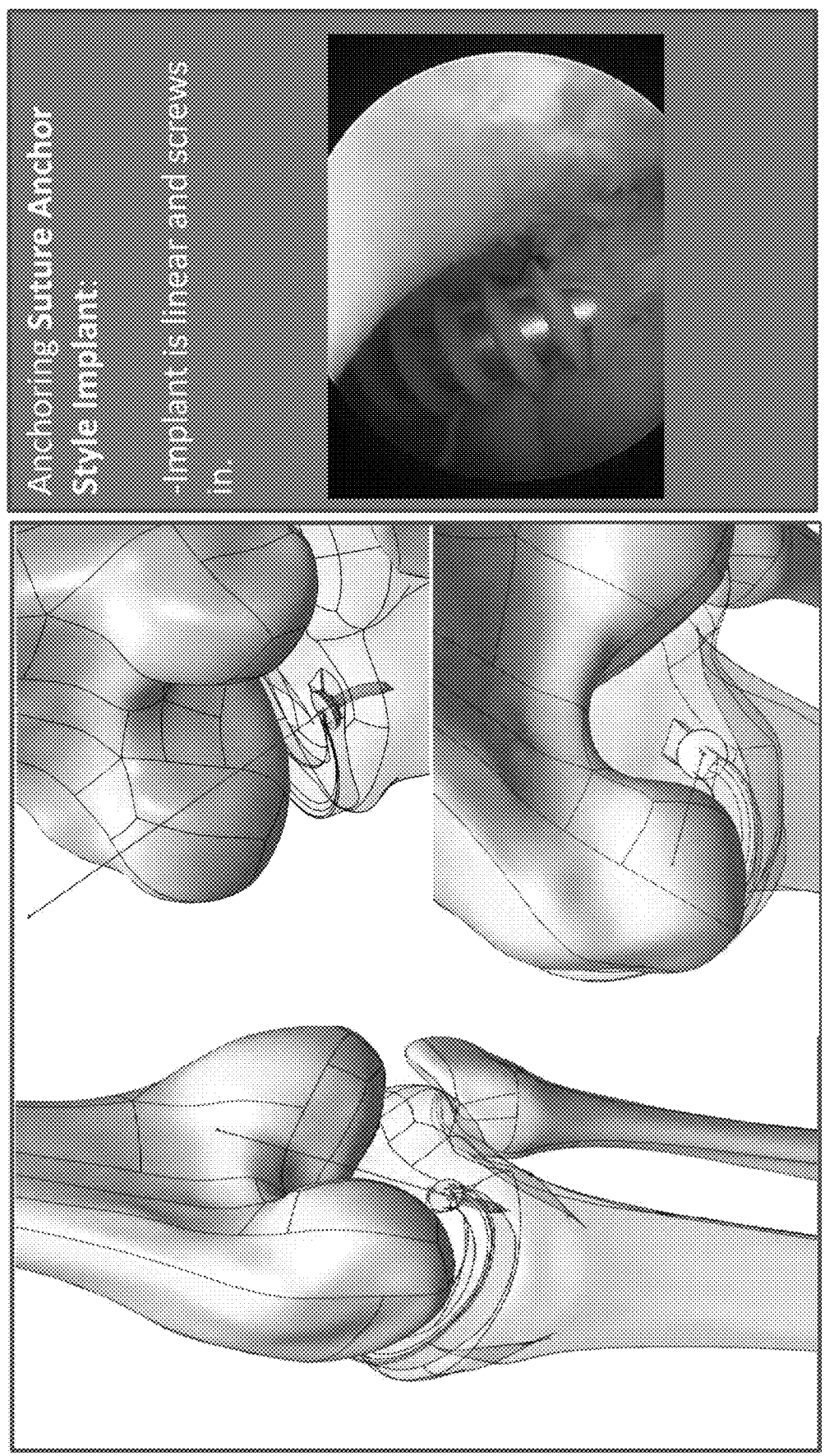
FIG. 49 illustrates anchoring of an exemplary suture anchor type implant by insertion from a posterior medial angle according to an exemplary embodiment of the present invention.

Similarly, FIG. 49 illustrates anchoring of an example suture anchor type implant. The implant may be linear, as shown in FIG. 49, and, in embodiments, may screw into the meniscus as described in greater detail below.

Figure 50:
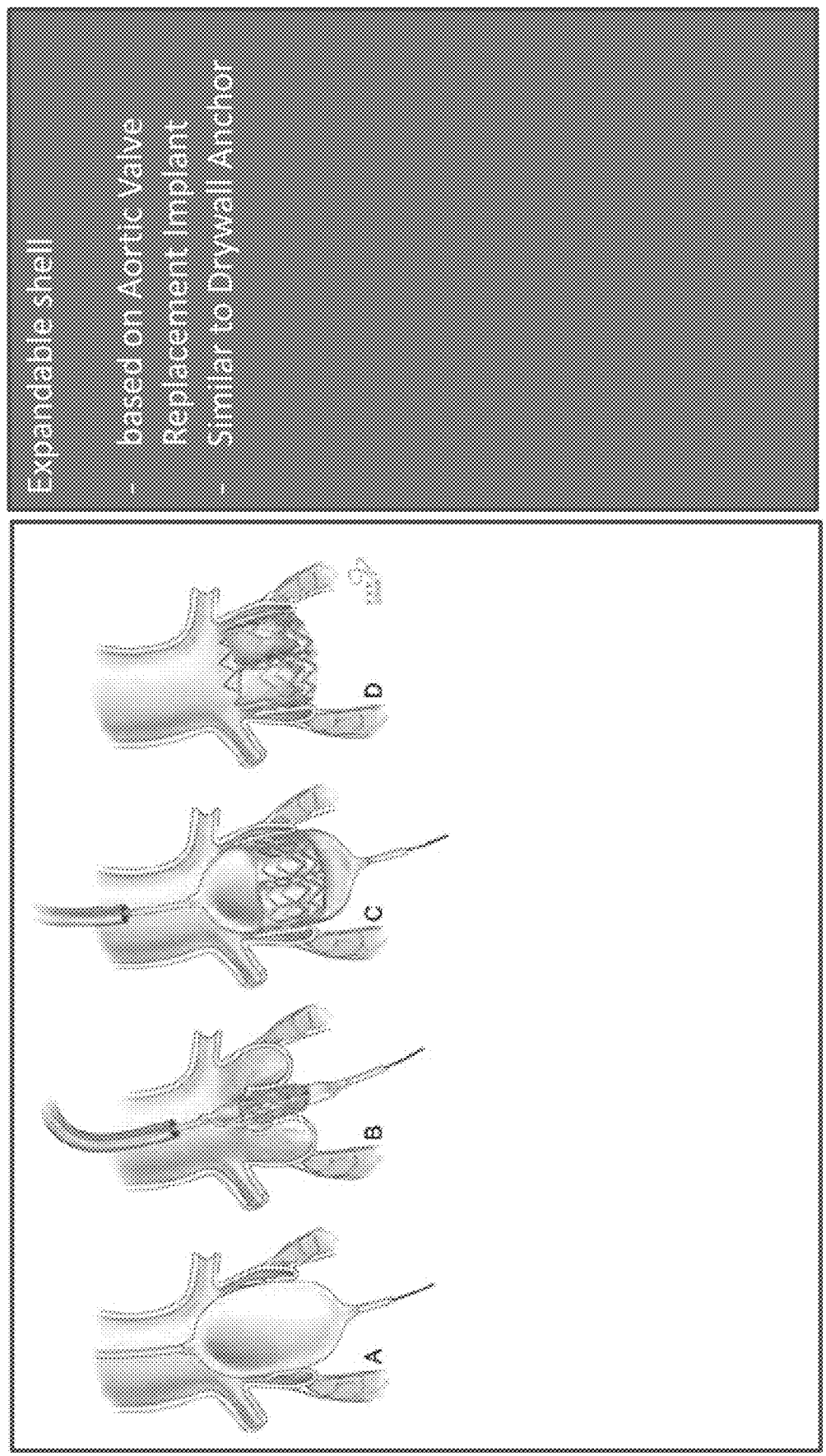
FIG. 50 illustrates anchoring of an exemplary implant using an expanded shell type anchor to lock into place, according to an exemplary embodiment of the present invention.

FIG. 50 presents an alternate anchoring mechanism—that of an expandable shell. This exemplary anchoring feature may be based on aortic valve replacement implants, and may also be similar to drywall anchors as used in the construction trades. In embodiments, it may be achieved by overlaying an exemplary implant with a metal shell, and it is this metal shell that would pull out and lock, as shown. The anchoring may be initiated by a user (e.g., a surgeon) pulling out a pull out pin. As shown, in embodiments, there may be three steps. Initially, at a first step, an implant having the example anchoring mechanism may be inserted, as described above, in a meniscus. In a second step, as shown, the pull out pin may be pulled out, thus expanding the metal shell. Finally, the pull out pin may be fully removed, thus locking the implant.

Thus, in embodiments, using this technique, an exemplary implant as shown in any of FIGS. 34-36 may be provided with such an anchoring overlay, in the nature of a metallic skin. Then, when the skin is expanded, the implant may, for example, be anchored in place.

Figure 51:
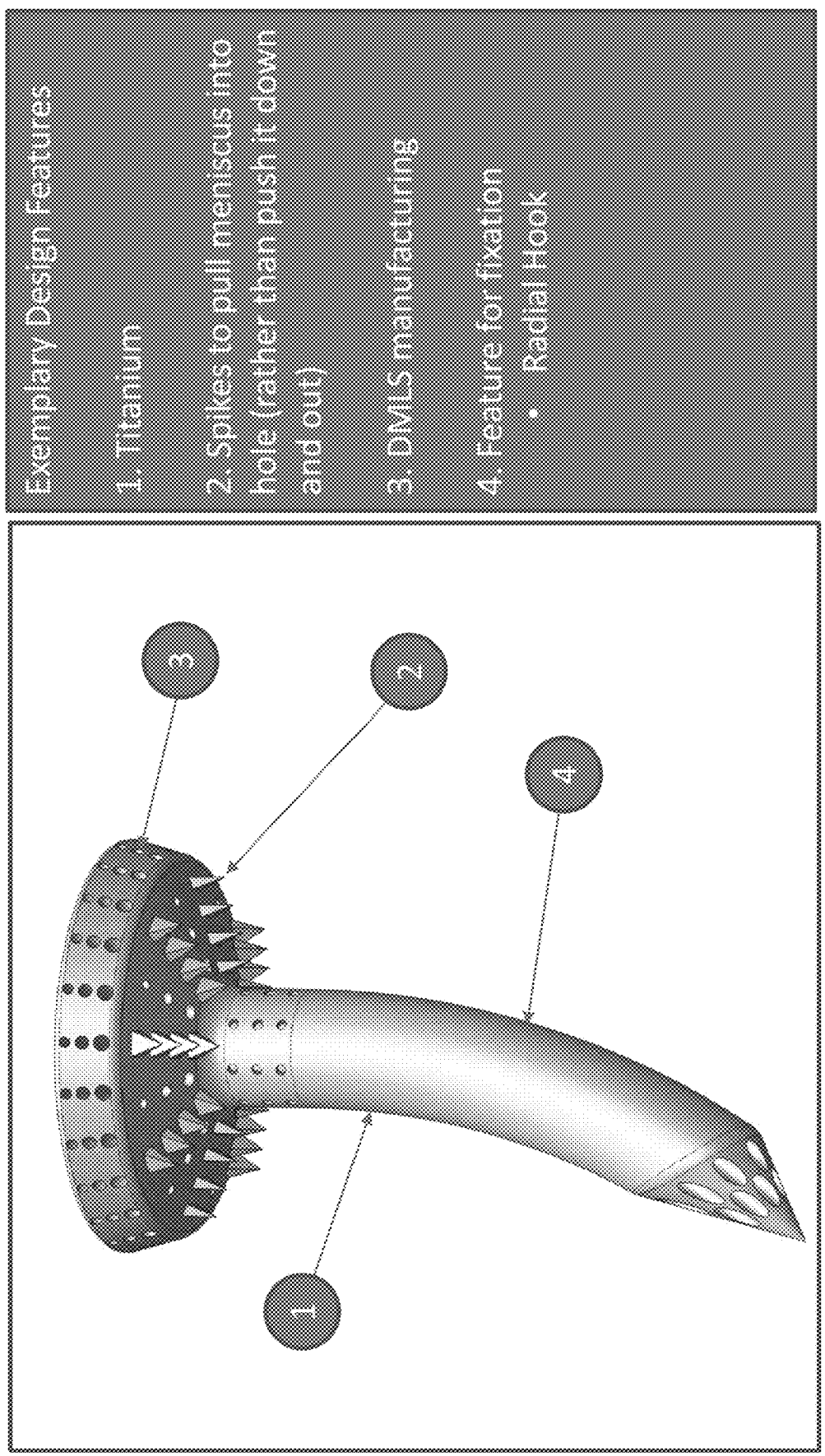
FIG. 51 depicts details of an exemplary tack type implant according to an exemplary embodiment of the present invention that may be manufactured using DMLS technology.

FIG. 51 depicts details of an exemplary tack type implant, according to various embodiments, that may be manufactured using Direct Metal Laser Sintering (DMLS) technology. It is noted that DMLS is an additive manufacturing technique that uses a Yb (Ytterbium) fiber laser fired into a bed of powdered metal, aims the laser automatically at points in space defined by a 3D model, and melts, or rather, welds, the material together to create a solid structure.

DMLS was developed by the EOS firm of Munich, Germany. With reference to FIG. 51, the exemplary implant may, for example, be made of titanium 1, and may include Spikes 2 provided on an underside of its upper portion. In embodiments, Spikes 2 may pull a portion of an example meniscus into the sides of the hole formed by the shaft of the tack as the tack is inserted into the meniscus. By this functionality, the portion of the meniscus thus pulled into the hole may sit vertically against the sides of the tack implant, and may thus contact both the implant's superior and inferior emitters, as described above, thus insuring good blood and nutrient flow to the meniscus. As noted, the example tack implant may be manufactured using DMLS 3, and its primary fixation technique may be radial hooks (also known as "radial spikes") 4, as described in connection with various example implants provided above.

Figure 52:
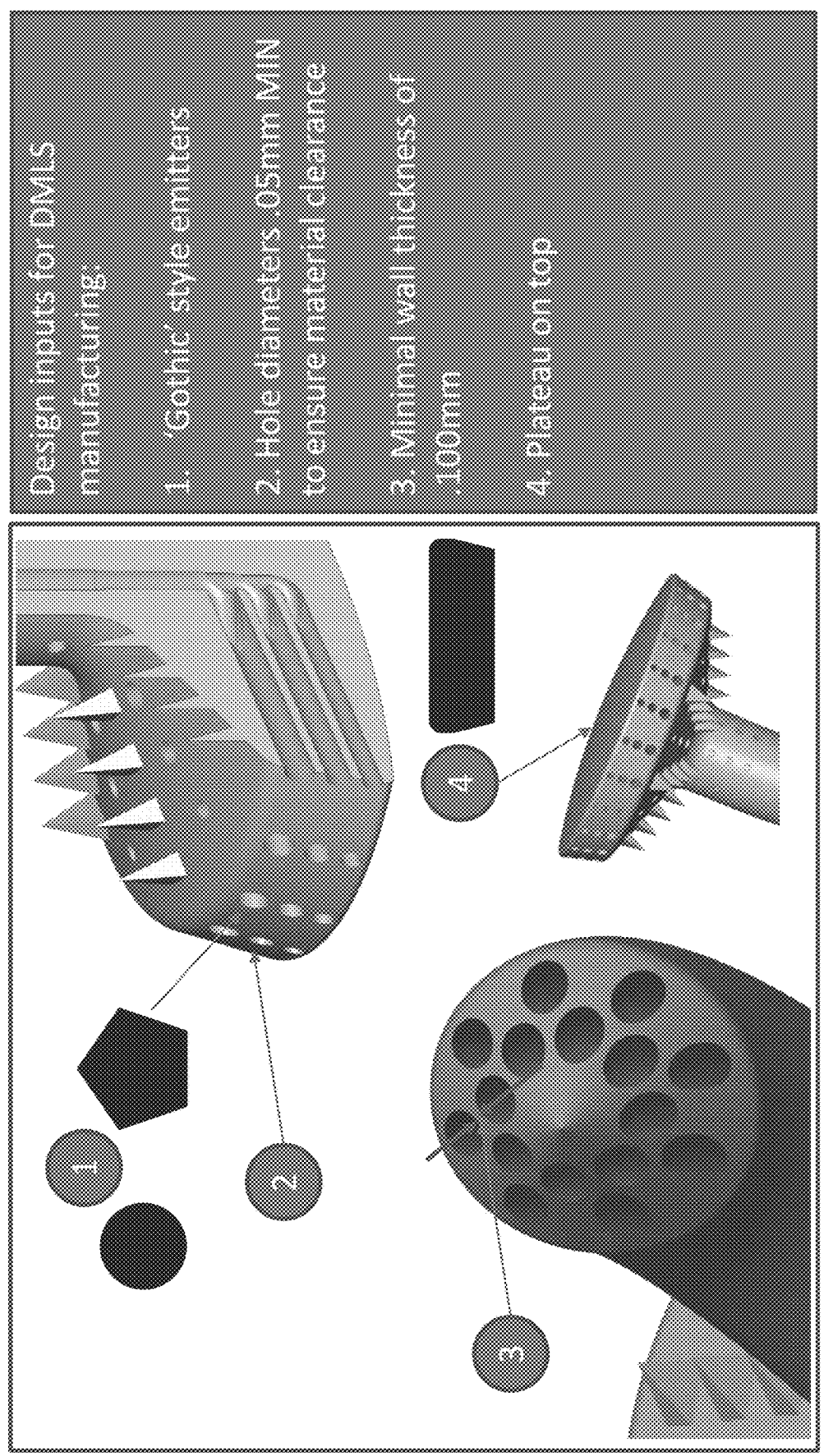
FIG. 52 depicts exemplary design inputs for DMLS manufacturing of the exemplary device of FIG. 51 according to an exemplary embodiment of the present invention.

FIG. 52 depicts exemplary design inputs for DMLS manufacturing of the exemplary device of FIG. 51 in accordance with various embodiments. With reference thereto, the design inputs may include "Gothic" style emitters 1; hole diameters 2 having a 0.05 mm minimum diameter to ensure material clearance; a minimal wall thickness 3 of 0.100 mm (for structural support), and a plateau shaped top 4. It is noted that by "Gothic" style emitters, a polygonal approximation to a circular opening is intended. The polygon may be a pentagon, as shown, or, for example, a hexagon or other multiple sided polygon. The reason why Gothic style emitters are required when utilizing DMLS manufacturing is that DMLS is unable to make perfect circles, inasmuch as it adds layers of material in subsequent series of passes. Each new layer must rest on some feature provided in a lower layer. Thus, the upper layers have to rest on something so that they can cantilever outwards or inwards. Thus, an absolute circle for a horizontal tube or pipe may not be used, because there would be nothing to rest on for vast portions of the circle. For similar reasons, the top cannot be absolutely straight (i.e., flat) because the center would not be resting on anything inasmuch as there is nothing underneath in many cases. By making it a plateau shape, one may effectively cantilever the central portions on top of the more peripheral portions, much in the way a dome is built using several horizontal layers, each additional layer cantilevering inwards until the space of the dome is closed. Thus, in DMLS, curves are created by a series of planes sitting on top of each other, and cantilevered inward or outward relative to a lower (generally the immediately lower) layer.

Figure 53:
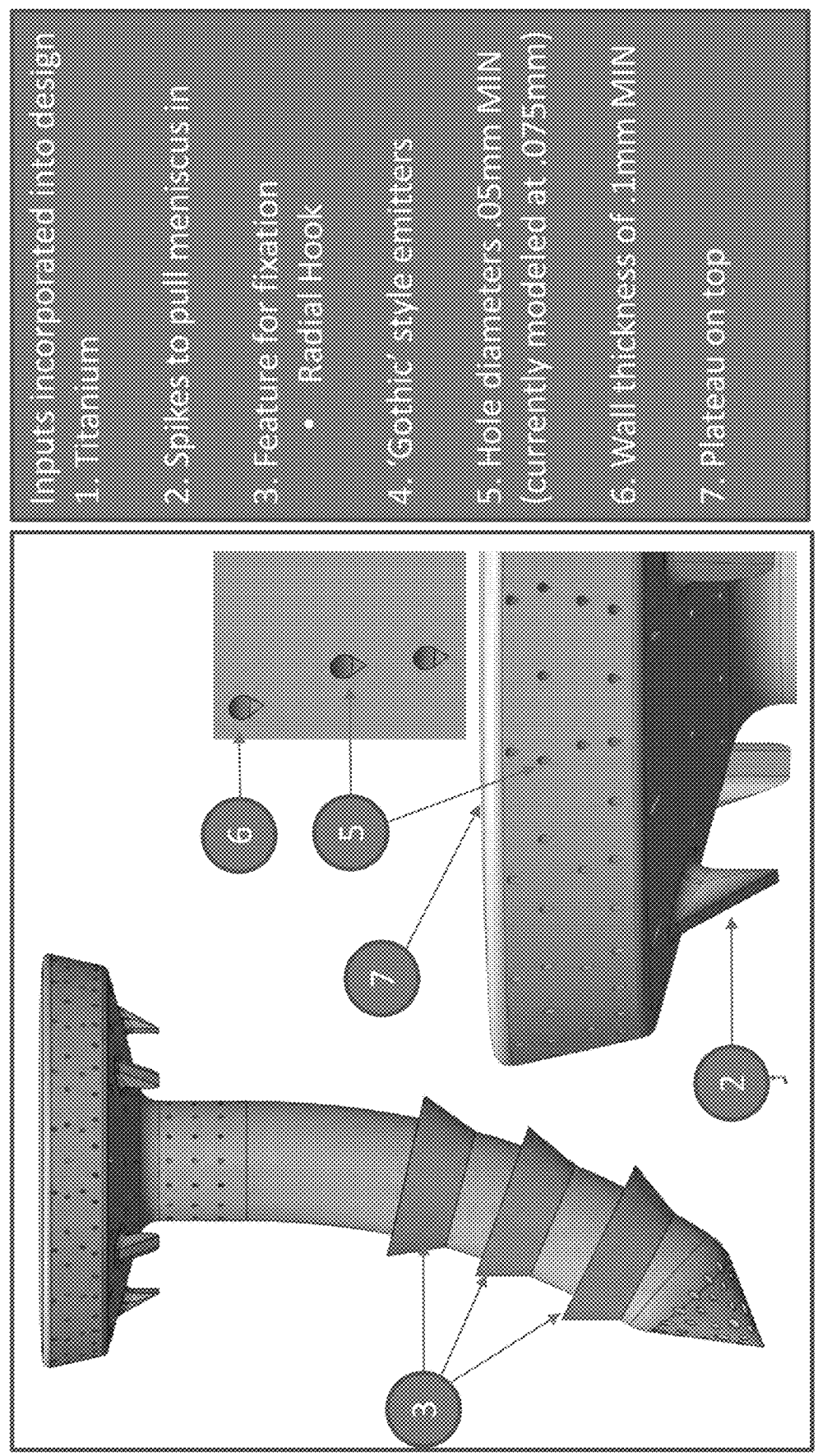
FIG. 53 depicts a variant of the tack type implant device of FIG. 51.

FIG. 53 illustrates incorporating various ones of the design considerations discussed above in connection with FIGS. 51 and 52 into an exemplary titanium embodiment of a tack type implant, such as was described above, with reference to FIG. 21-34. With reference to FIG. 53, and also with reference to FIGS. 51-52, the design may, for example, be implemented in titanium. The design may also be provided with Spikes 2 to pull the meniscus down and into the hole, as described above. The fixation feature may include Radial Hooks 3, and the emitters—both radial emitters and inferior circumferential emitters—as shown, may be made using "Gothic" polygonal approximations for a circle, as described above. Additionally, the hole diameters 5 may be a minimum of 0.5 mm, and there may be a minimum wall thickness 6 of 0.1 mm, for example. Finally, the top may be fashioned in a plateau shape 7 (as opposed to a flat upper surface). It is noted that, by using/implementing these features, an exemplary inventive implant may be manufactured using DMLS technology.

Figure 54:
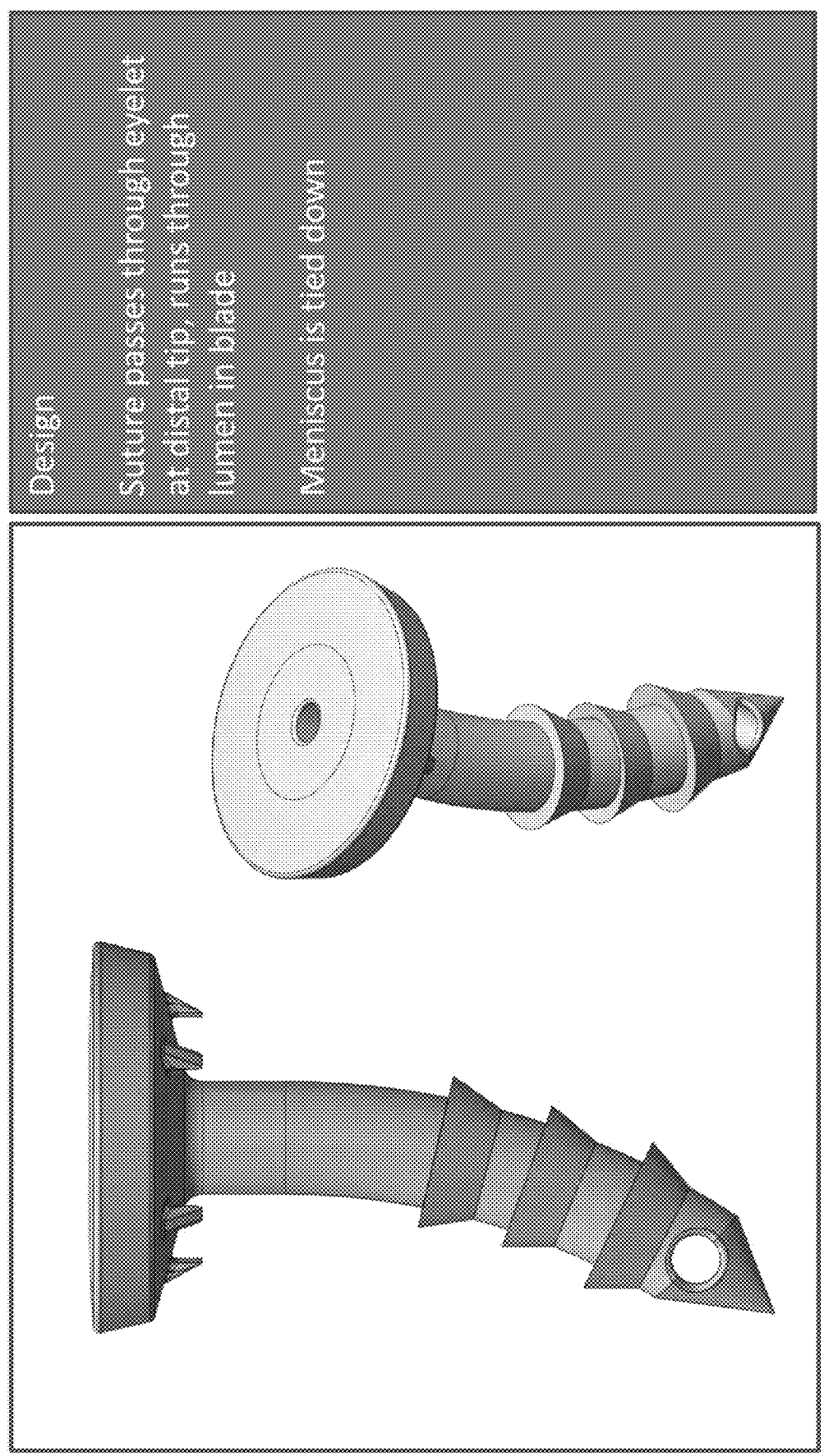
FIG. 54 depicts a further variant of the tack type implant device of FIG. 51, which includes a suture anchor at its distal end.
Figure 55:
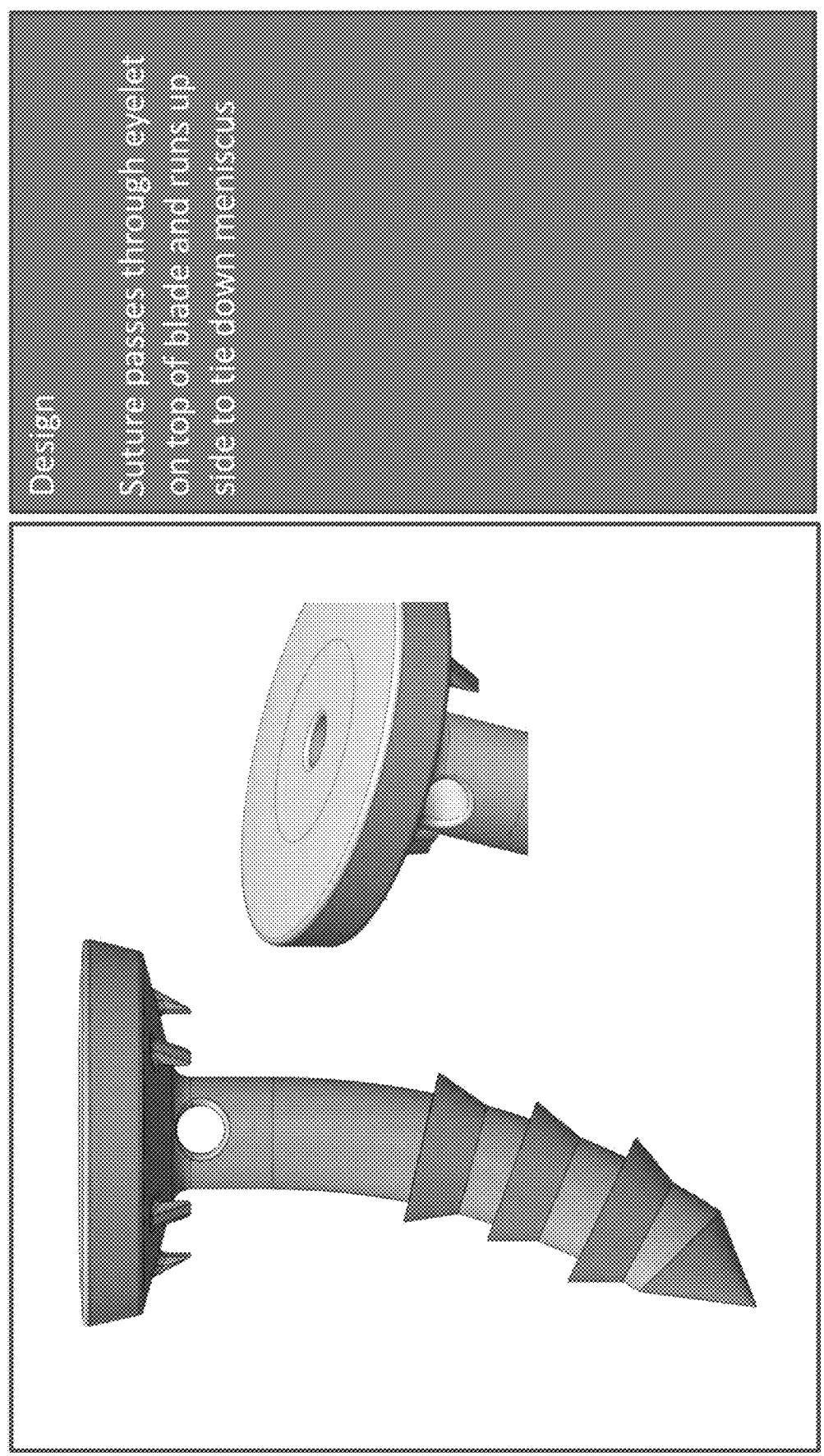
FIG. 55 depicts a variant of the tack with suture anchor implant of FIG. 54, where the eyelet is positioned proximally on the implant, at the top of the shaft.
Figure 56:
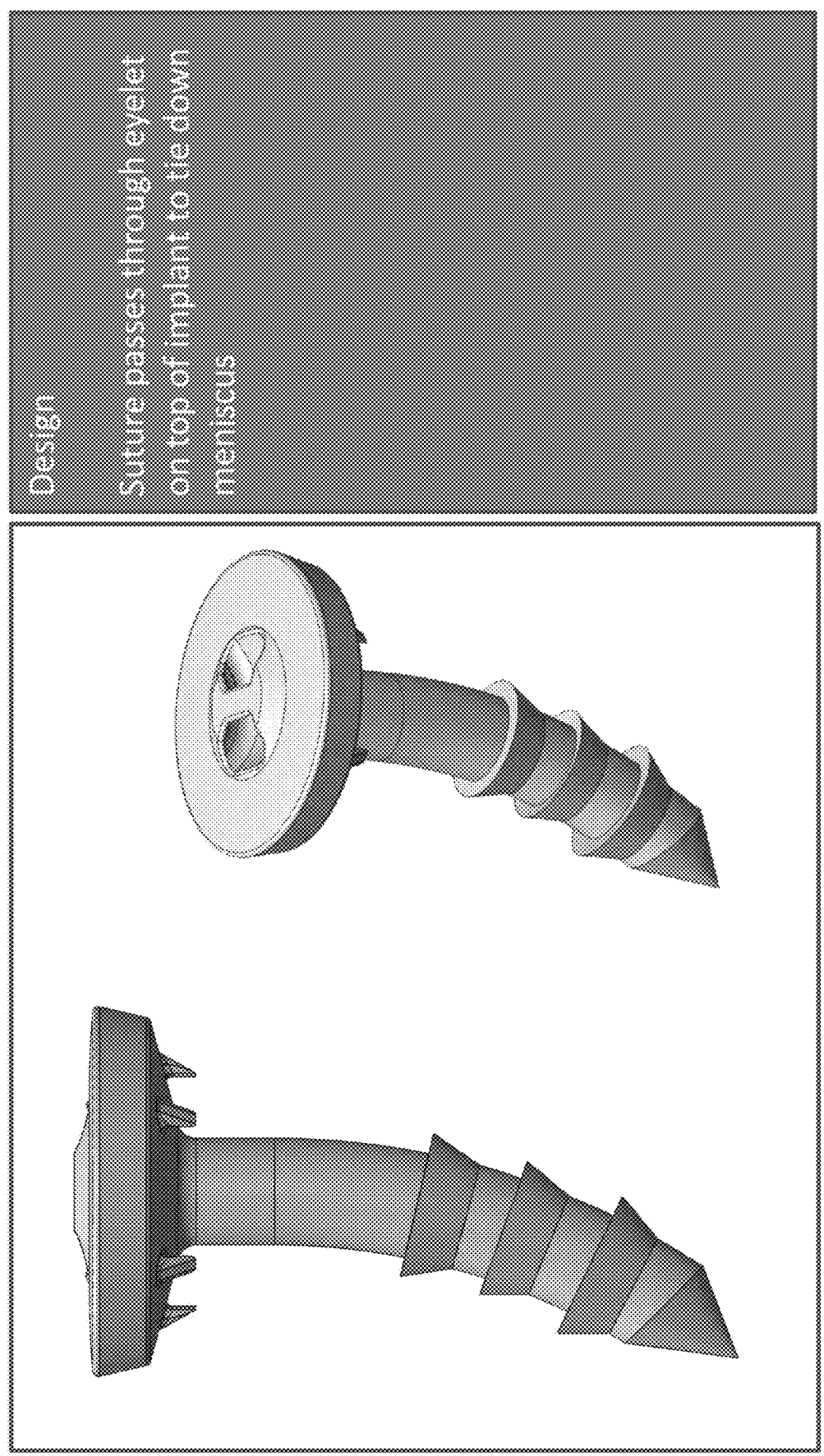
FIG. 56 depicts a further variant of the tack with suture anchor implant of FIGS. 54 and 55, where the eyelet is provided on the top of the cap.

FIGS. 54-56 illustrate adding the additional feature of a suture anchor to the exemplary tack embodiment shown in FIG. 53. In embodiments, the eyelet, through which the suture may be passed by a surgeon, may be provided at various locations on the implant, either distal or proximal. FIGS. 54, 55 and 56 each show one possible location for the eyelet. Thus, FIG. 54 shows the suture eyelet through which the suture is threaded to be located at the distal tip of the implant, for example. In this embodiment, it may run through a lumen within the blade and then be knotted off in the meniscus, as shown to the left and right of the top of the implant in FIG. 54, the grey hashed areas representing the meniscus, and the blue line with knots on each end representing a suture. Therefore, as shown in FIG. 54, the suture passes through the eyelet at the distal tip and runs up through lumen in the blade to tie down the meniscus. Similarly, FIG. 55 locates the eyelet for the suture at the top of the blade or central shaft and the suture runs up the sides of the cap or upper portion of the tack implant, to be knotted off so as to tie down the meniscus, as shown in the left image of FIG. 55. As in the case of FIG. 54, the grey hashed areas represent the meniscus, and the blue line with knots on each end represents a suture.

A third alternative, shown in FIG. 56, is, for example, to provide an eyelet on top of the cap of the implant to tie down the meniscus. In this embodiment, the suture may, for example, simply pass through that eyelet. It is noted, however, that in this case the suture thus only exerts its tying down functionality at the very top of the exemplary implant. The placement of FIG. 54 is thus preferred, as it provides the maximum affixation. Even more preferable would be a suture anchor that requires no knots. Exemplary embodiments implementing this feature are presented in connection with FIGS. 64 through 86, described below. The design concept underlying such embodiments is described in connection with FIG. 57, next described.

D. Suture Anchor with Irrigation

FIG. 57 presents an alternate suture anchor type of implant device, in accordance with various embodiments. With reference thereto, a suture anchor type implant is shown that has fixation features provided in its distal portion, with an irrigation network or system of canals or emitters provided in its proximal portion. In embodiments, the anchor may have a "tap-in" option, providing an upper surface that a user may apply a tapping force to, to push the anchor down into tissue, and a set of radial hooks along the distal portion of the shaft, as shown, for example, in the left image of FIG. 57. Or, for example, the implant may have a threaded screw-in option as shown in the right image of FIG. 57. It is noted that the suture anchor implants of FIG. 57, lacking a "distributor cap" at their proximal end, as in the various embodiments described above, may often be more versatile for other applications, such as, for example, rotator cuff and other joint repair, or prophylactic intervention. Thus, such an suture anchor implant without a "distributor cap", with additional fixation provided by a knotless suture, may be used for any repair of soft tissue to bone where healing is dependent upon blood flow from the bone to the soft tissue. For example, any tendon, such as, for example, rotator cuff, patella, Achilles, quadriceps, or triceps, or, for example, cartilage, such as labrum in the shoulder and hip, meniscus, etc.

Further, the irrigation provided by such an implant (which is also provided by the other embodiments discussed above, via their irrigation systems), may be of great benefit to micro fracture procedures where, instead of poking holes, an implant with an irrigation system according to various embodiments may be punched into an area of bare bone that has lost articular cartilage, such as, for example, femoral condyle, talus, or femoral head. Thus, irrigation through implants according to various embodiments may be stimulated by the impact of implantation and proceed continuously.

E. Optimization of Channel Size and Channel Quantity.

FIGS. 58 through 63, next described, illustrate exemplary modelling of the channels, and optimizing channel diameter versus overall cumulative channel diameter.

Figure 58:
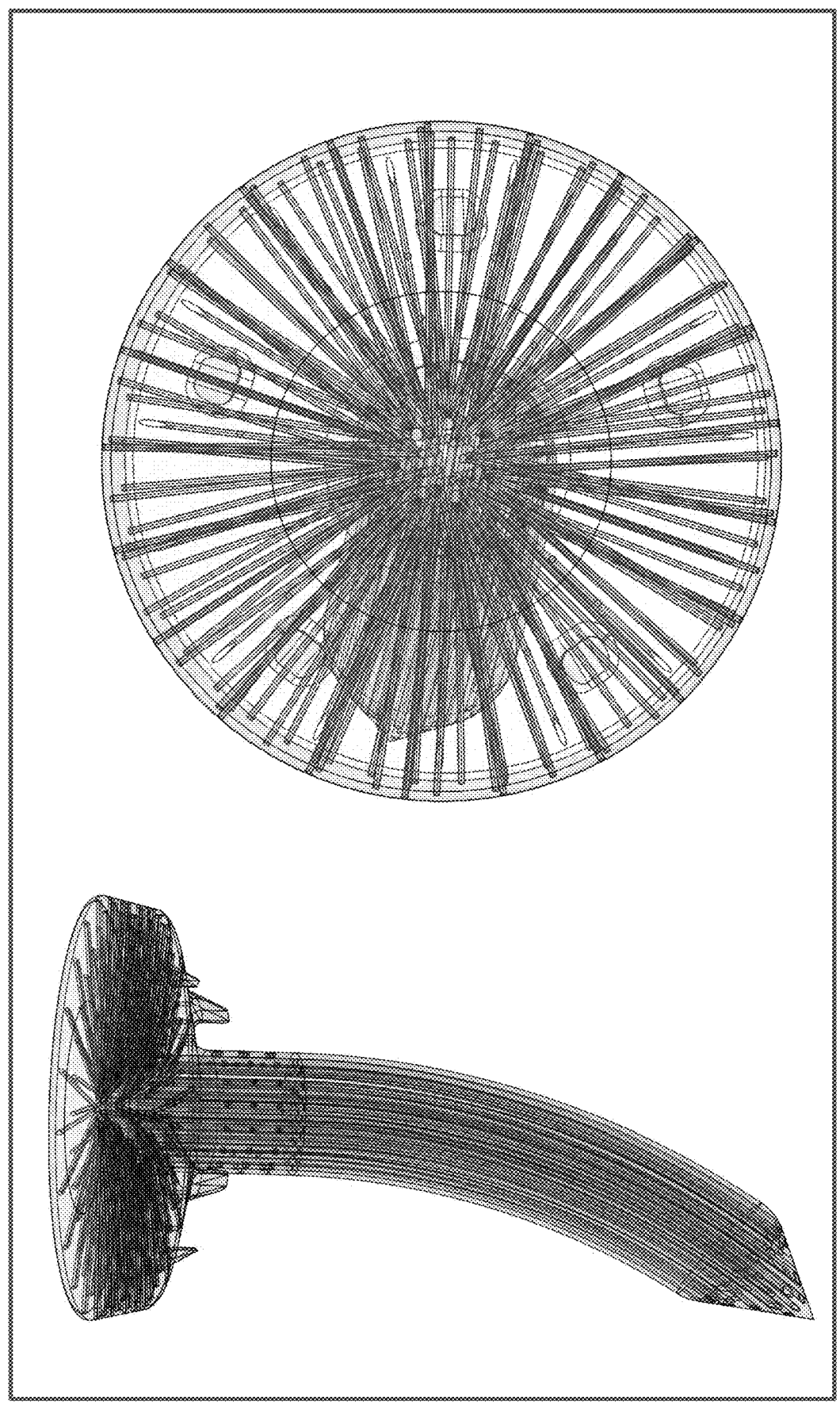
FIGS. 58 and 59 depict transparent views of the channels in the exemplary tack type device of FIGS. 51 and 53.
Figure 59:
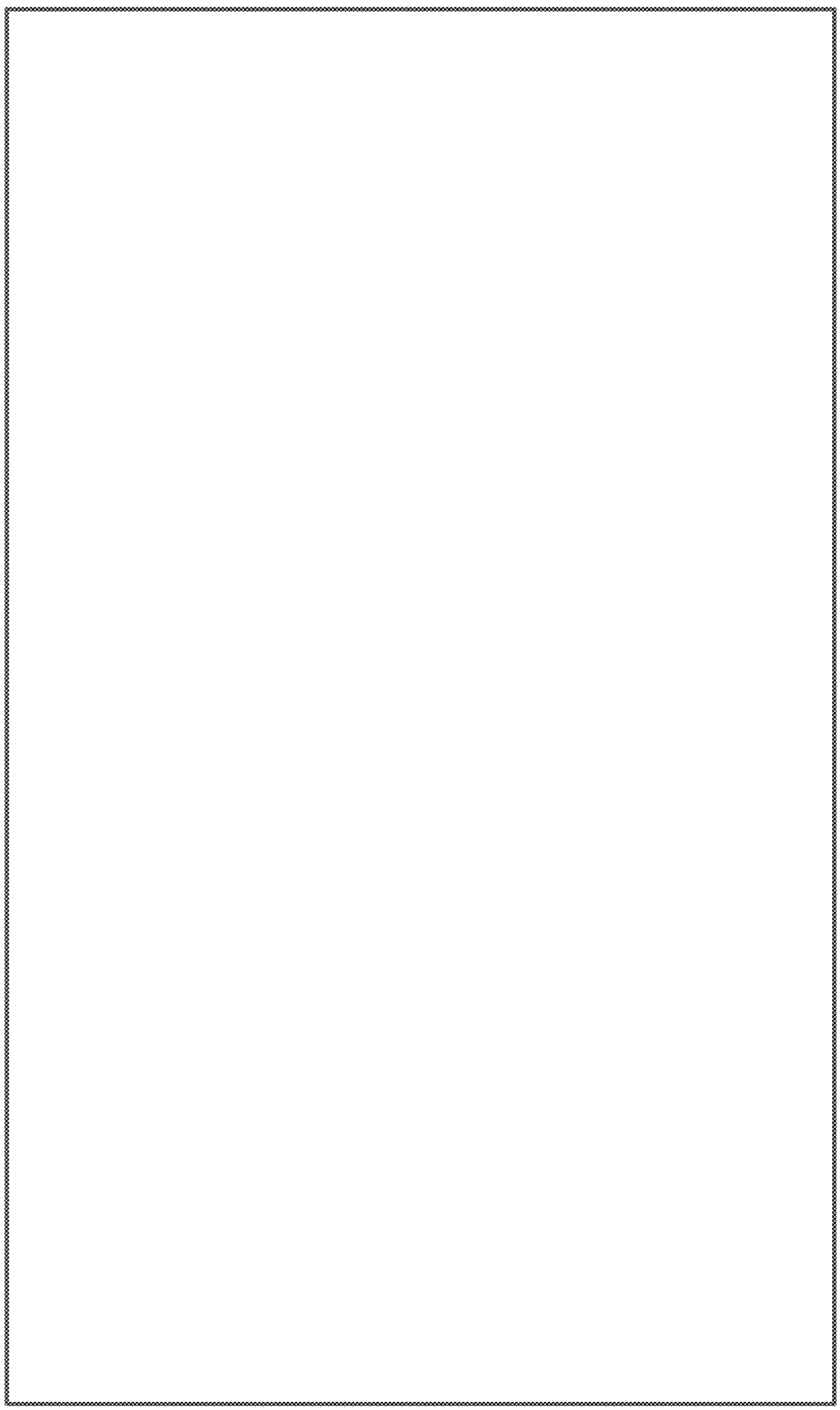

For easy reference, FIGS. 58 and 59 illustrate once again the exemplary tack device of FIG. 53. However, the focus in FIGS. 58 and 59 is on the network of vertical canals, horizontal canals and emitters. It also shows the spikes provided on the underside of the cap to pull in the meniscus, as described above.

Figure 60:
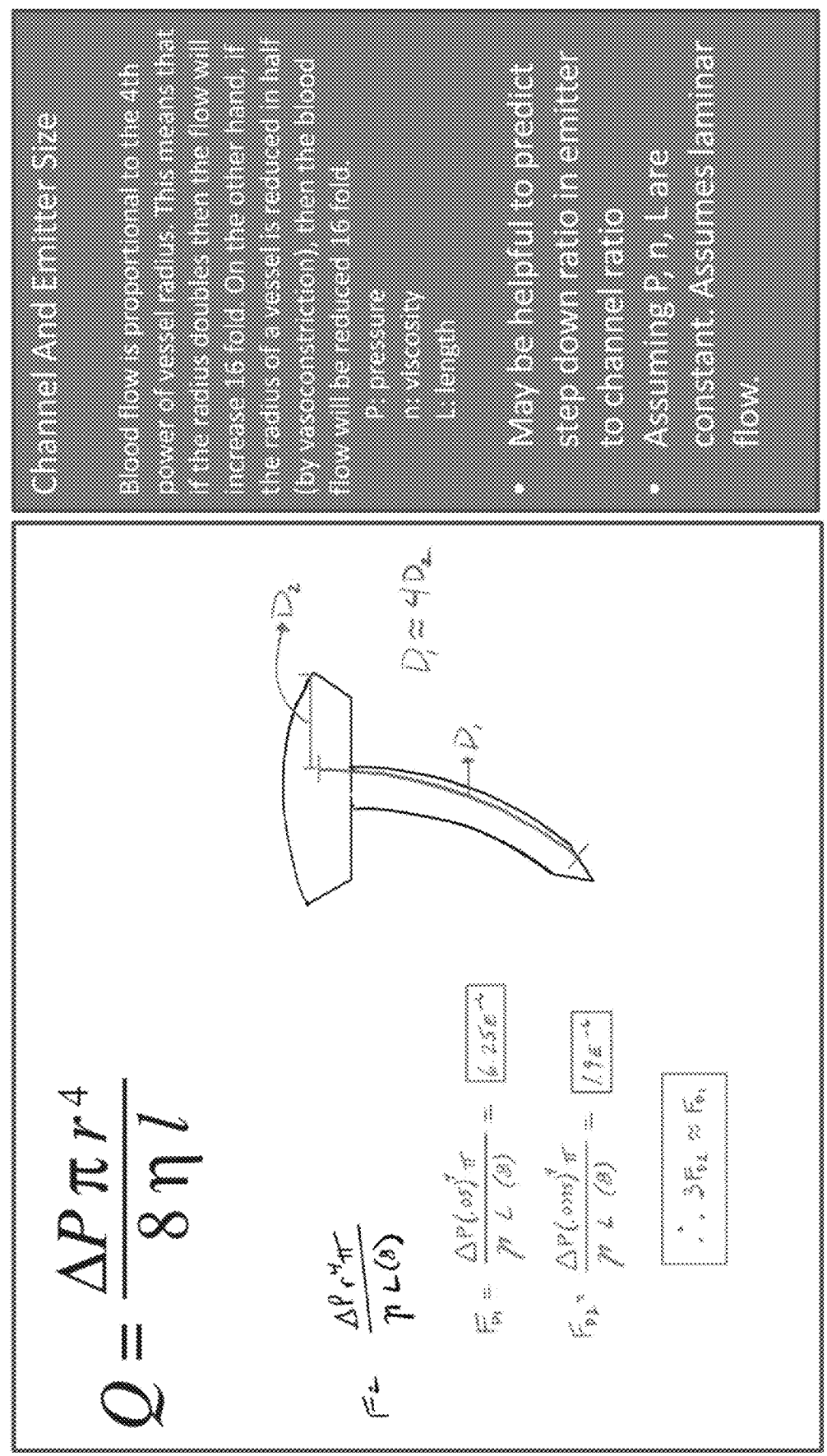
FIGS. 60-62 present exemplary modelling of channel and emitter sizes for optimization purposes.
Figure 61:
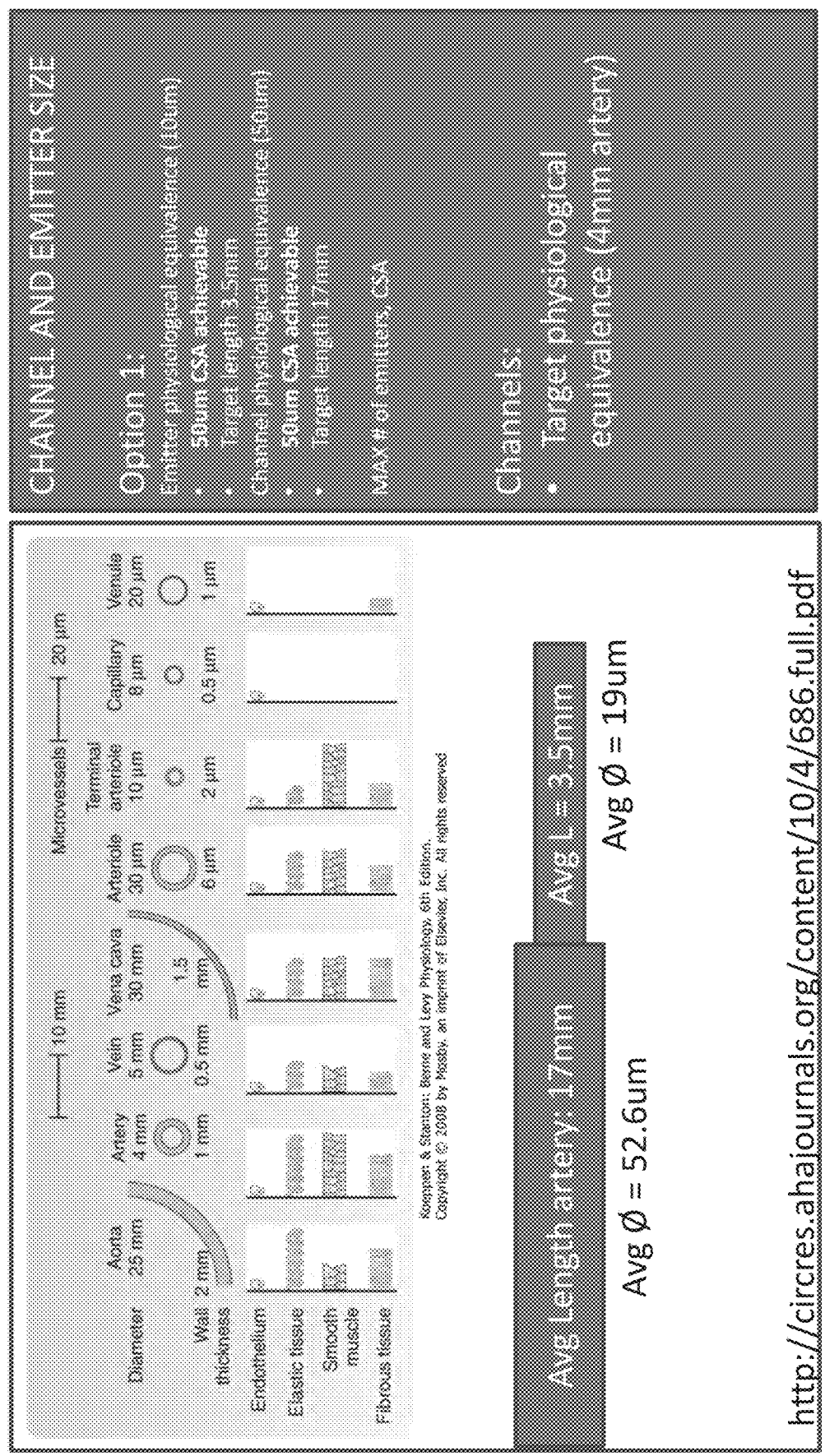

FIGS. 60 and 61 illustrate how to optimize channel and emitter size. FIG. 60 illustrates a model, that may be used, in embodiments, to calculate flow in where the diameter of emitters in the cap are one quarter that of vertical channels coming up in the central shaft or blade. As can be seen in FIG. 61, assuming those dimensionalities, flow through the vertical central channel, with diameter D1, is approximately three (3) times that of flow through a horizontal emitter having one quarter the diameter, or D2, where D1=4*D2. Thus, as shown, 3FD2≈FD1, where FD1=flow through a diameter D1 and FD2=flow through a diameter D2. As shown, blood flow is proportional to the $4^{th}$ power of vessel radius, and the assumption is made that Pressure (P), Viscosity ($\eta$) and Length (l) are constant. Flow is thus calculated by the following equation: $F$ (or $Q$)=$\Delta P r^4 \pi / \eta L$(8).

Figure 62:
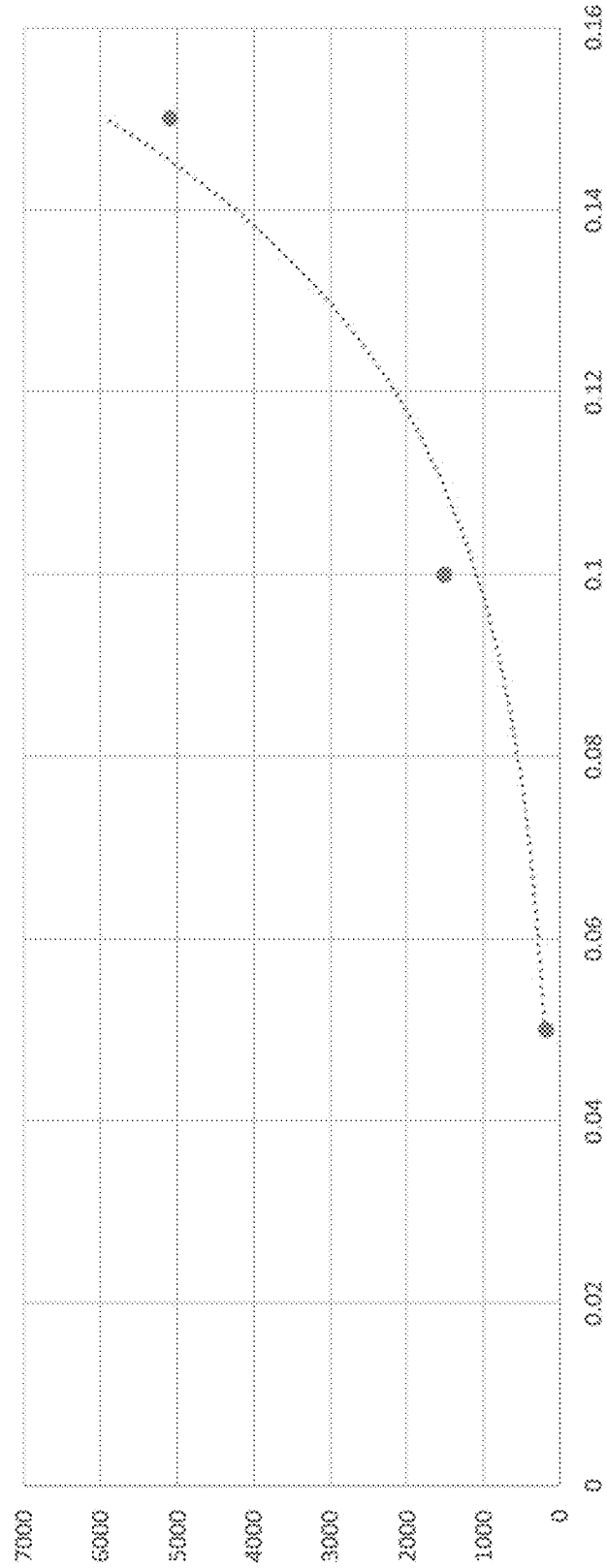

Taking this information, FIGS. 61 and 62 illustrate the relationship of flow rate to channel size (diameters of the channels in millimeters). As can be seen with reference to FIG. 62, flow rate is directly related (but not linearly) to channel size, and total emitter flow may be maximized by having a smaller number of relatively large diameter channels as shown in the bottom row of the chart presented in FIG. 62. FIG. 62 illustrates the relative diameters of vascular structures in humans, and it is here noted that capillaries, where actual diffusion occurs in mammals, are about 8 microns in diameter. Therefore, if one desires to imitate this natural process, in order to diffuse blood and nutrients to surrounding meniscal root and vascularized meniscal tissue, a "capillary bed" would be optimal. This is illustrated, for example, in FIG. 63, next described.

Figure 63:
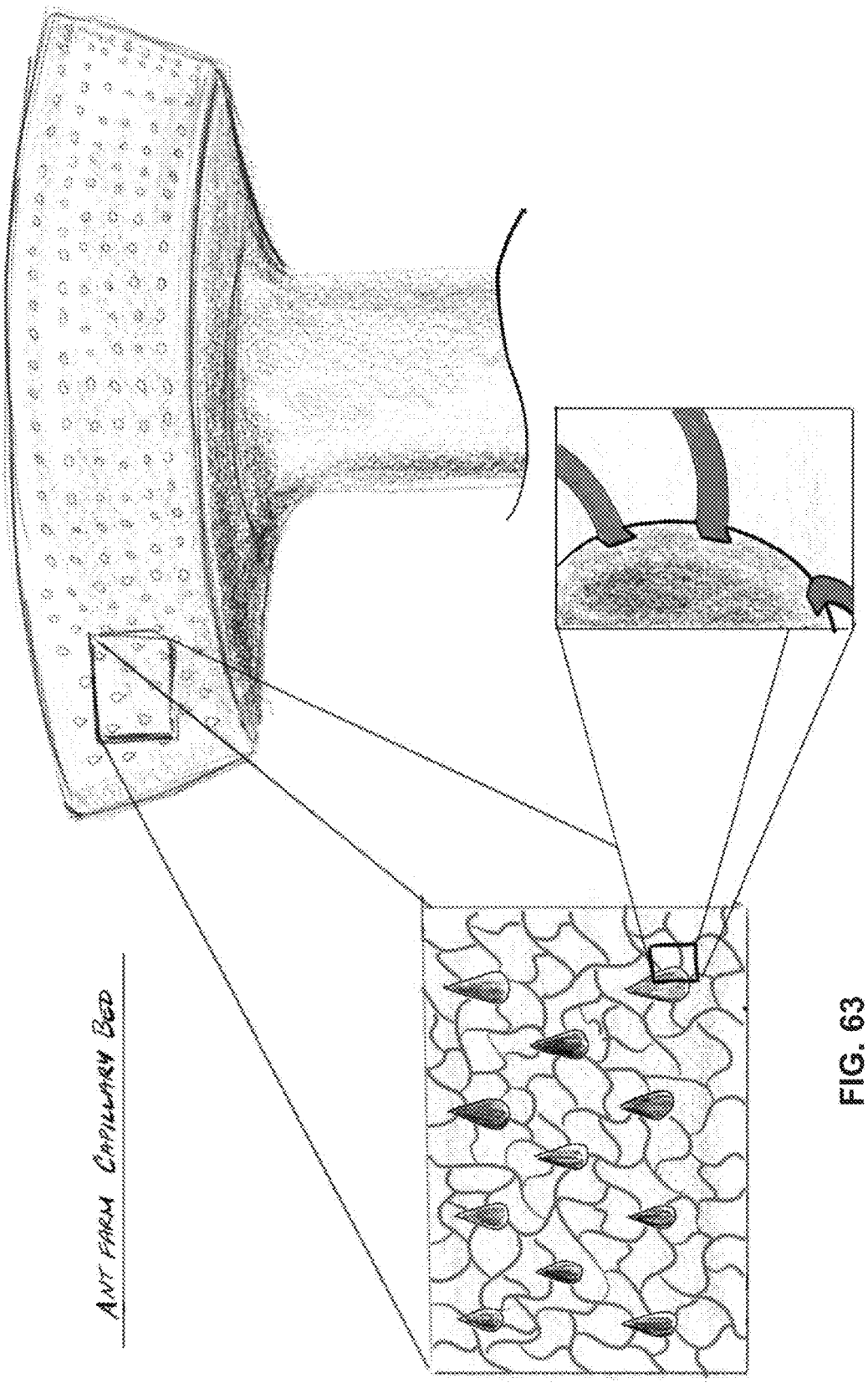
FIG. 63 depicts an exemplary "ant farm" type capillary bed for the cap or "washer" of an exemplary tack device according to an exemplary embodiment of the present invention.

FIG. 63 illustrates an "Ant Farm" surface texture, which involves cutting grooves in the outer surface of a tack type implant's cap connecting the circumferential emitters provided in the cap. It is noted that in addition to simulating a capillary bed, as shown in the figure, the rough texture promotes bone growth and inter-digitation for better fixation. In an exemplary embodiment of this "Ant Farm" surface texture, grooves connecting emitter holes may be 30 microns deep, and 50 microns long. Other sizes are, of course, possible, as appropriate, these being merely exemplary. In this example embodiments, the emitters themselves are of a "tear drop" shape, but it is understood that any shape of the emitters may be used, as described above.

F. Details of Exemplary Suture Anchor Type Implant

As noted above in connection with FIG. 57, in accordance with various embodiments, an implant may be fixed in a joint in the manner of a suture anchor, while additionally providing all of the irrigation functionalities described above in connection with the "blade and washer" and "tack" type implant devices. In embodiments, such an implant would thus provide double fixation, from both the suture and the sharp tip of the implant protruding into the bone below the meniscus, for example. FIGS. 64-86, next described, illustrate such embodiments, with their numerous possible variations.

Figure 64:
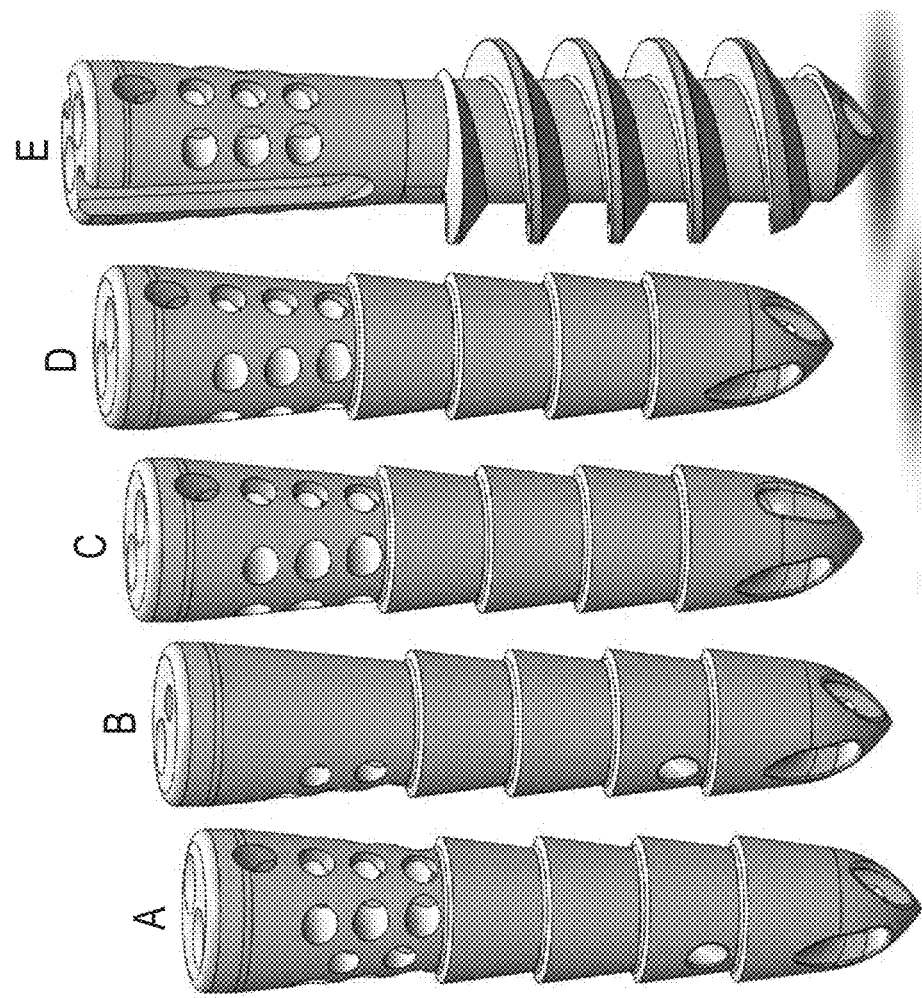
FIGS. 64 and 65 each depict five exemplary embodiments of a suture anchor type implant according to various exemplary embodiments of the present invention, for ease of illustration, these configurations are referred to as A through E, where A appears on the far right of the figures, and configuration E appears on the far left.
Figure 65:
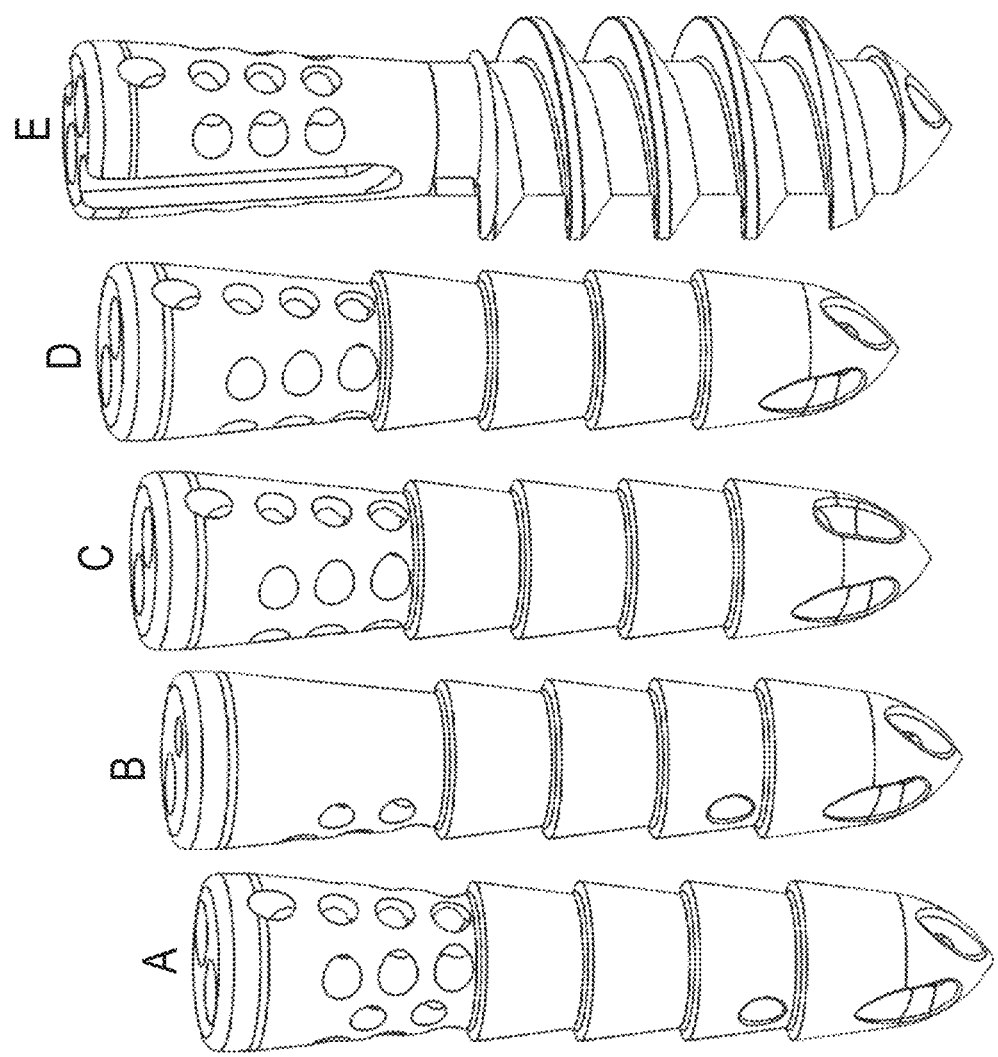

FIGS. 64 and 65 depict five variations of a suture anchor type implant in accordance with various embodiments. FIG. 64 is a solid rendering and FIG. 65 an outer contour rendering of the five exemplary embodiments.

FIG. 66 is a chart presenting the various features of each of the exemplary configurations A-E depicted in FIGS. 64-65. For reference, it is noted that in FIGS. 64 and 65, Configuration A appears at the far left and Configuration E appears at the far right in each figure. As can be seen with reference to FIG. 66, configuration A does not have proximal emitters, i.e., emitters on its top portion. This is because, with reference to FIG. 64, and each of configurations B, C, D and E, the insert device, or inserter interface, as shown in FIG. 70 below, protrudes (much in the nature of a cylindrical fluorescent bulb), via two prongs, into two corresponding receiving holes in the top of each of Configurations A-E of FIGS. 64 and 65.

Figure 70:
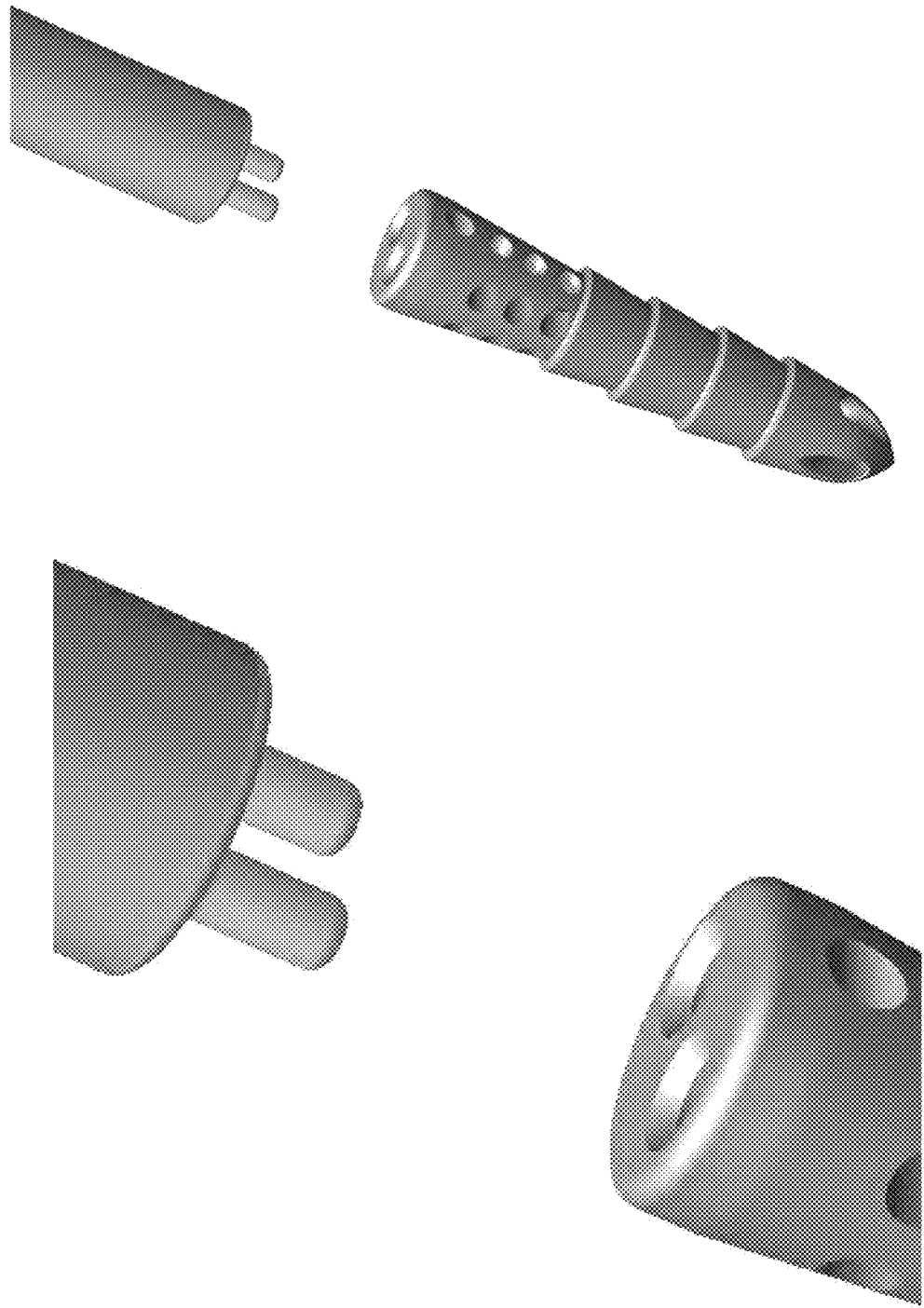
FIG. 70 illustrates an interface to fit into the top of each configuration of FIG. 65 for insertion of the implant device in a human joint according to an exemplary embodiment of the present invention.

However, in configuration A, the receiving holes for the two protruding prongs of the inserter interface of FIG. 70 are not connected to anything. On the other hand, in the remaining configurations of FIGS. 64 and 65, configurations B through E, the receiving holes for the prongs of in the inserter interface are themselves connected to the internal irrigation channels in the implant device, which descend all the way to the distal tip of the exemplary implant. Thus, in Configurations B through E the receiving holes for insertion also serve as emitters on the top of the device, whereas, in the case of Configuration A, the receiving holes simply end and there are no emitters out of the top of the implant device. It is also noted with reference to FIGS. 64 and 65, as well as FIGS. 68 and 69, that Configuration E, being the sole threaded device, is therefore designed to be screwed into place in a joint, such as, for example, the meniscus of the knee. Thus, Configuration E additionally has recessed portions to receive a suture thread, which are oriented at a 90° rotation from the receiving holes of the inserter interface prongs. These recesses allow for the suture, once threaded through the eyelet at the proximal portion of (i.e., just above) the threads, to be recessed relative to the outer diameter of the implant shaft. It is noted that in this Configuration E, unlike Configurations A-D, because Configuration E is threaded and is designed to be inserted in a screwing manner into a patient, the eyelet for the suture anchor cannot be placed at the distal tip of the implant as in the other configurations which are tapped into place. The reason being that a suture threaded around the outside portion of the threads, through the eyelet, and out and up again over the outer portion of the threads on the other side of the device would most likely not remain in place and would get twisted all around the implant—thereby losing its tension and defeating its affixation purpose.

Figure 67:
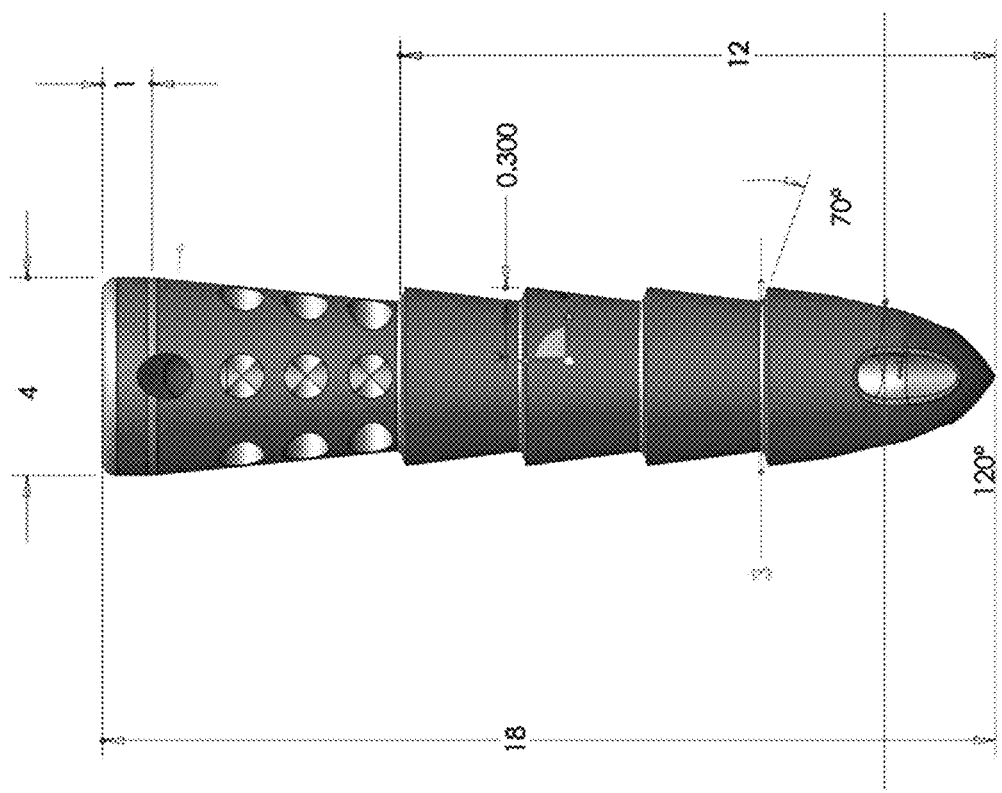
FIG. 67 depicts overall dimensions of the outer profiles of Configurations A through D of FIG. 65.
Figure 68:
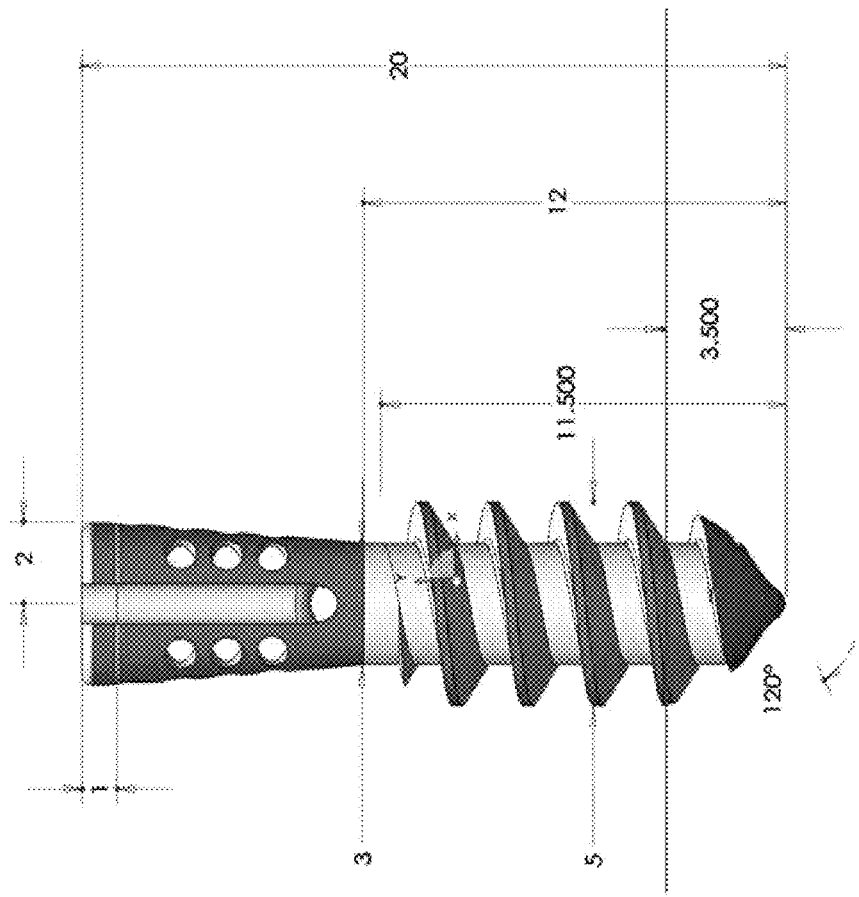
FIG. 68 depicts overall dimensions of the outer profiles of Configuration E of FIG. 65.

FIGS. 67 and 68 respectively show exemplary (not limiting) overall dimensions of the outer profile of the two types of exemplary implants being, on the one hand, in FIG. 67, Configurations A, B, C and D, and on the other hand, in FIG. 68, Configuration E. With reference to the example of Configurations A-D in FIG. 67, the overall length may be 18 mm, and the outer diameter of the proximal top may be 4 mm. The ribs may push out 0.3 mm from the smallest diameter of the shaft, which is 3 mm, as shown. The top surface of the ribs need not be flat, but may be angled downwards, at an angle of 70 degrees off of the vertical, as shown (30 degrees off of the horizontal). The bottom portion of the implant, where there are no emitters, may be 12 mm, i.e., the distal ⅔ of the overall implant shaft.

Similarly, FIG. 68 depicts an example of Configuration E, which, as noted, has the threaded shaft for screwing into tissue, as opposed to being pushed or tapped in. Its dimensions are similar as those of the example of FIG. 67, but it is slightly longer, at 20 mm overall. Its central shaft may have an outer diameter of 3.0 mm, and at the outer edge of a thread, the diameter may be 5. mm. As in the previous example, the tip or distal portion where no emitters are, may be 12 mm. However the extra 2 mm added to the proximal portion allows for the suture eyelet, which can no longer be placed at the distal tip, so as not to be fouled or twisted by the threads as the implant is rotated into the tissue. As shown in FIG. 68, it may be the bottom (distal) 3.5 mm tip portion which begins to narrow, to allow for easy insertion into a patient's tissue.

FIG. 69 presents a number of magnified views of a Configuration E exemplary implant. With reference thereto, in the left image, one can clearly see the two receptacles for the prongs of the inserter interface and, at a 90° angle to those prongs (or more precisely to the line along which those two receptacles lie), one may see the recessed grooves for the suture. These suture receiving grooves may extend from the cap, or proximal end, of the implant downwards distally to just above the first thread, as shown in both images of FIG. 69. A comparison of FIG. 64 with FIG. 69 indicates that the design of Configuration E has a longer proximal portion in order to accommodate the eyelet relative to that of Configurations A, B, C, and D, where the ribs (or radial spikes) begin closer to the top of the device than the analogous threads begin in Configuration E.

The right image of FIG. 69 presents a view of the entire implant, and in the middle a top view of the implant is presented.

As referenced in passing above, FIG. 70 presents details of an exemplary inserter interface, or handle, which, in embodiments, may be used with each of Configurations A-E shown in FIGS. 64 and 65. At the top of each of the two views of FIG. 70 is a cylindrical device which a physician or other healthcare professional may hold or grab. Two prongs protrude out of the bottom surface of this cylindrical device. The two prongs are designed to fit into the two receiving holes provided at each of the tops of Configurations A-E, as described above. Once the prongs of the cylindrical handle are inserted into the receiving holes on the top of an example implant device, a user can either push, tap or screw, as the appropriate case may be, the implant device into the patient's joint. The protruding prongs from the handle may, for example, have an outer diameter equal to the inner diameter of their receiving holes on the exemplary implant, and this diameter may be, for example, 0.9 mm. Additionally, the two prongs of the handle/inserter may be spaced farther apart than the spacing between the two receiving holes, for example, so that the two prongs need to be bent in slightly, to fit into the receiving holes, thus creating a friction based fit. As was noted above, Configuration A is the only configuration that does not have these insertion receiving holes performing a "double duty." In Configurations B-E these receiving holes are connected to the irrigation network running longitudinally and horizontally into the implant device and serve, therefore, as additional emitters on the top of the device to bring blood and nutrients to the meniscus that surrounds the implant. It is noted that the precise position of an exemplary implant within the exemplary human knee meniscus is the subject of, and described in connection with, FIGS. 78-86 below.

Figure 71:
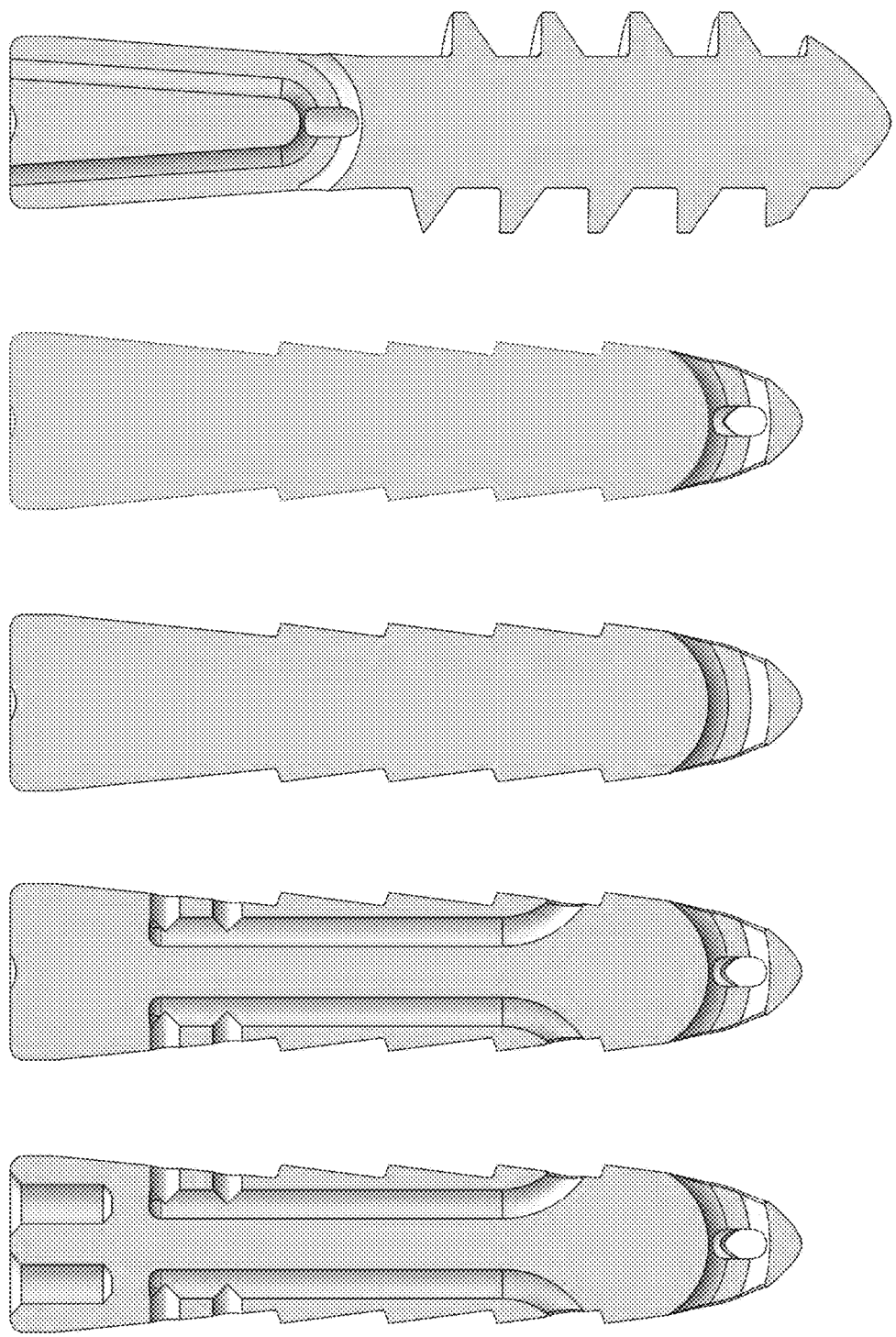
FIGS. 71 and 72 each depict longitudinal cross-sections of each of Configurations A through E of FIG. 65.
Figure 72:
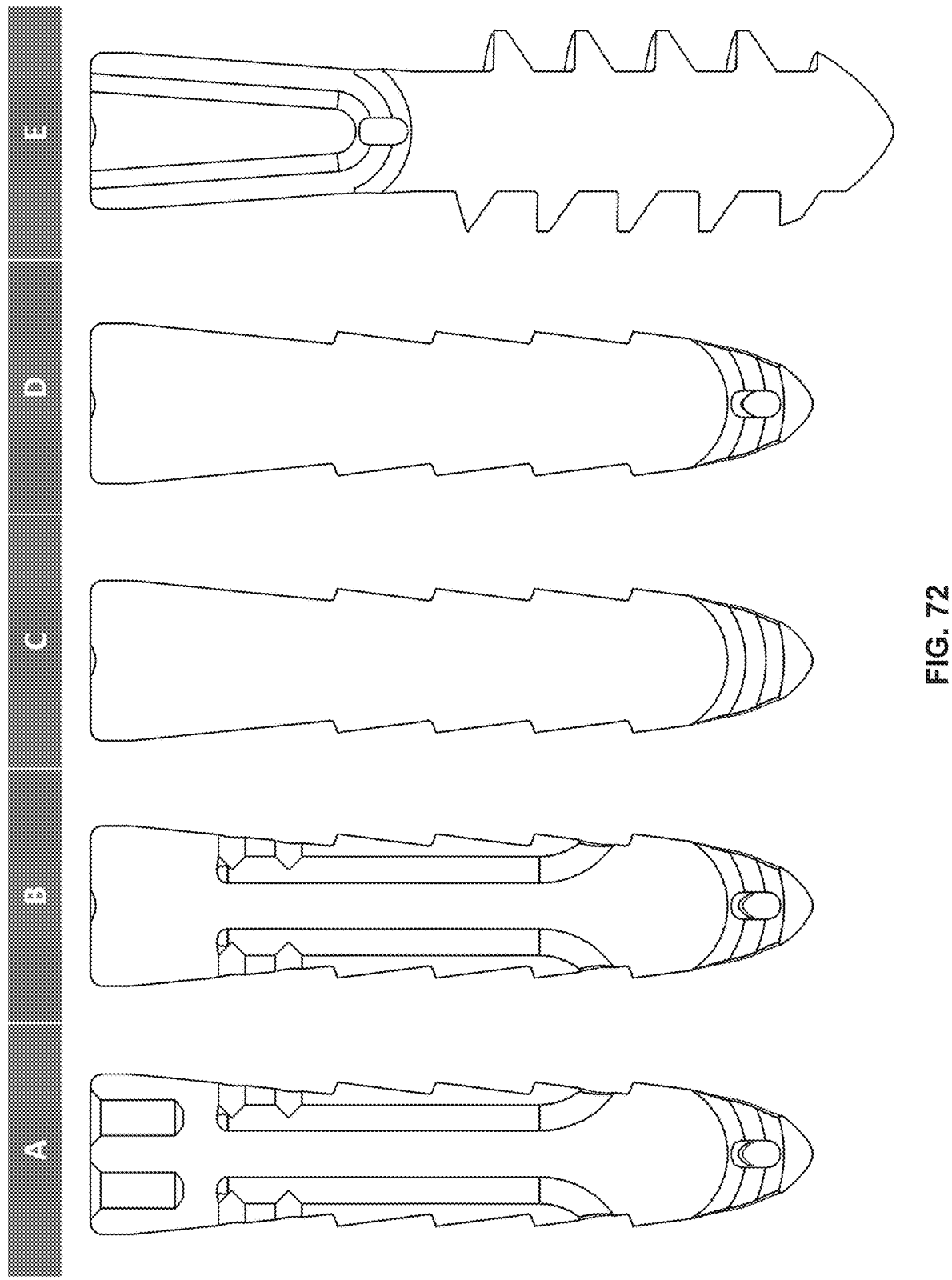

FIGS. 71 and 72 depict longitudinal (i.e., vertical) cross-sections through each of configurations A-E of FIGS. 64 and 65.

Figure 73:
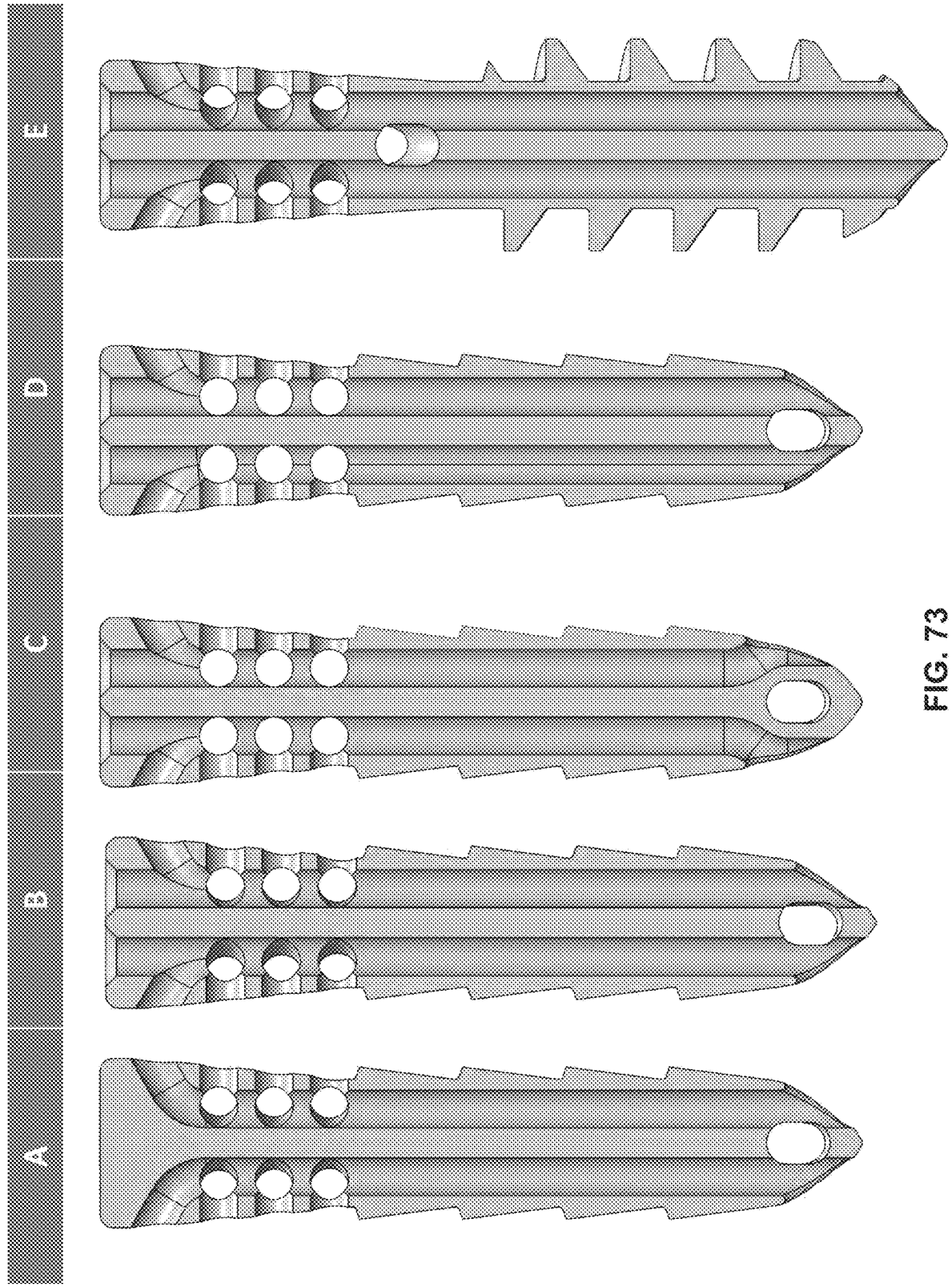
FIGS. 73 and 74 each depict longitudinal cross-sections of each of Configurations A through E of FIG. 65 taken along a vertical plane rotated from the vertical plane used for the cross-sections of FIGS. 71 and 72 by 90 degrees.
Figure 74:
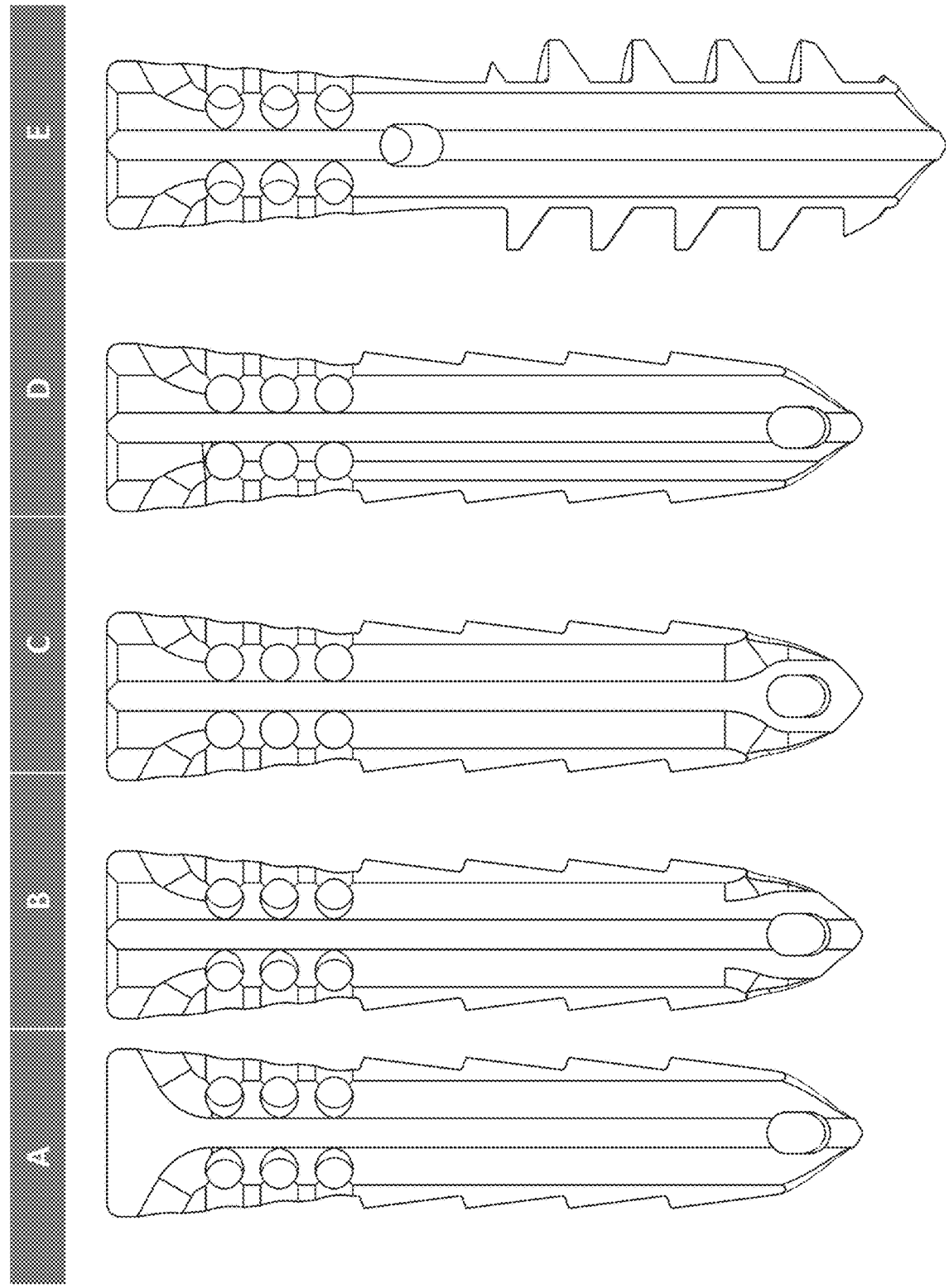

FIGS. 73 and 74 depict the same five Configurations A through E of the example implant with suture anchor using a different set of longitudinal cross sections. In the case of FIG. 73, the plane used for the longitudinal cross sections is rotated relative to the vertical plane used for the longitudinal cross sections shown in FIGS. 71 and 72, by 90°.

Figure 76:
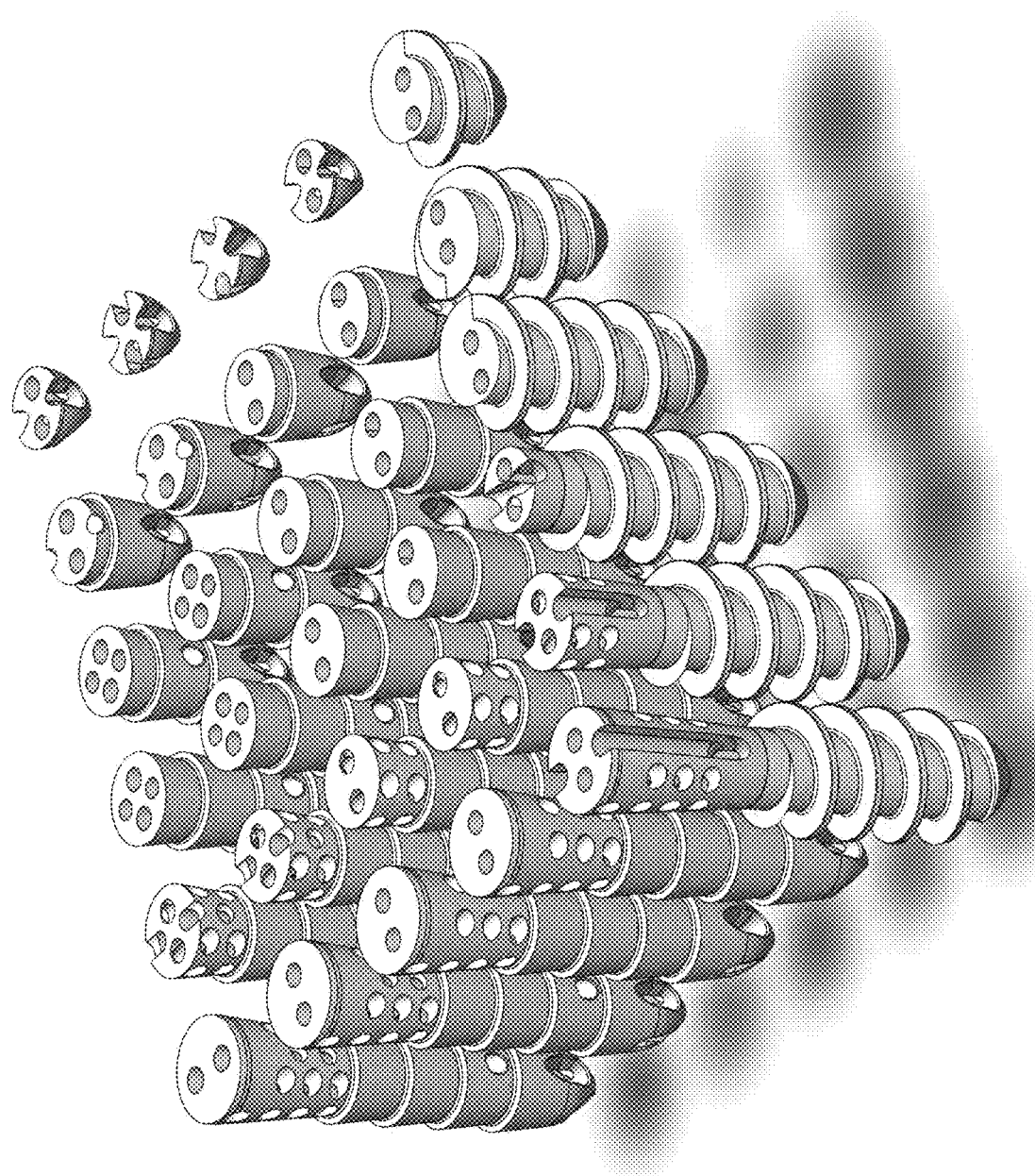
FIG. 76 depicts the same cross sections of FIG. 75 in perspective view with the remainder of the portion of the shaft distal to each cross section for ease of orientation as to where along the shaft the cross section was taken.
Figure 77:
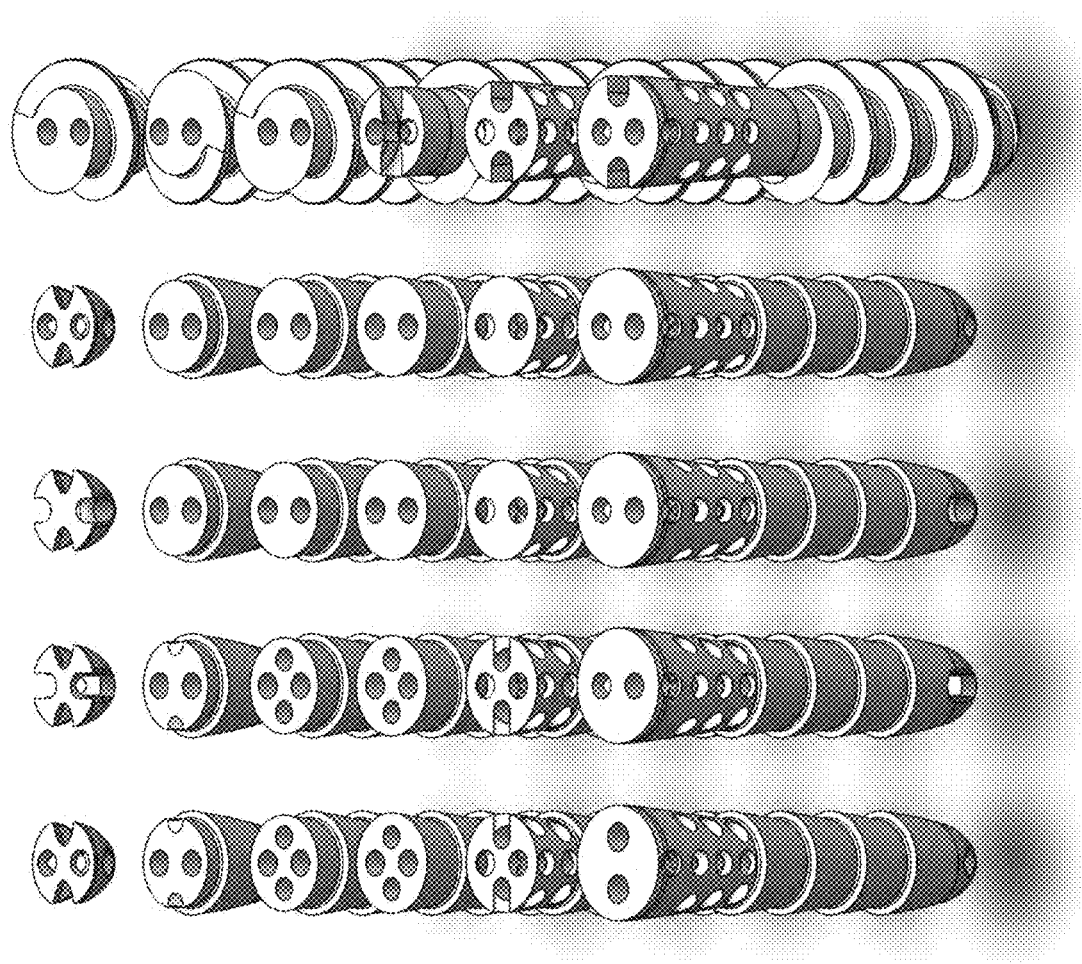
FIG. 77 depicts the cross sections of FIG. 76 in a frontal view.

FIG. 75 depicts various horizontal cross sections taken at various points along the respective shafts of Configurations A-E, respectively. FIG. 76 depicts the same cross-sections in perspective view with the remainder of the portion of the shaft that is distal (i.e., below) each cross sectional plane for ease of orientation as to where, or how far down, along the shaft the cross-section was taken. Similarly, FIG. 77 depicts the very same 3D cross sections shown in FIG. 76 in a frontal view.

Figure 78:
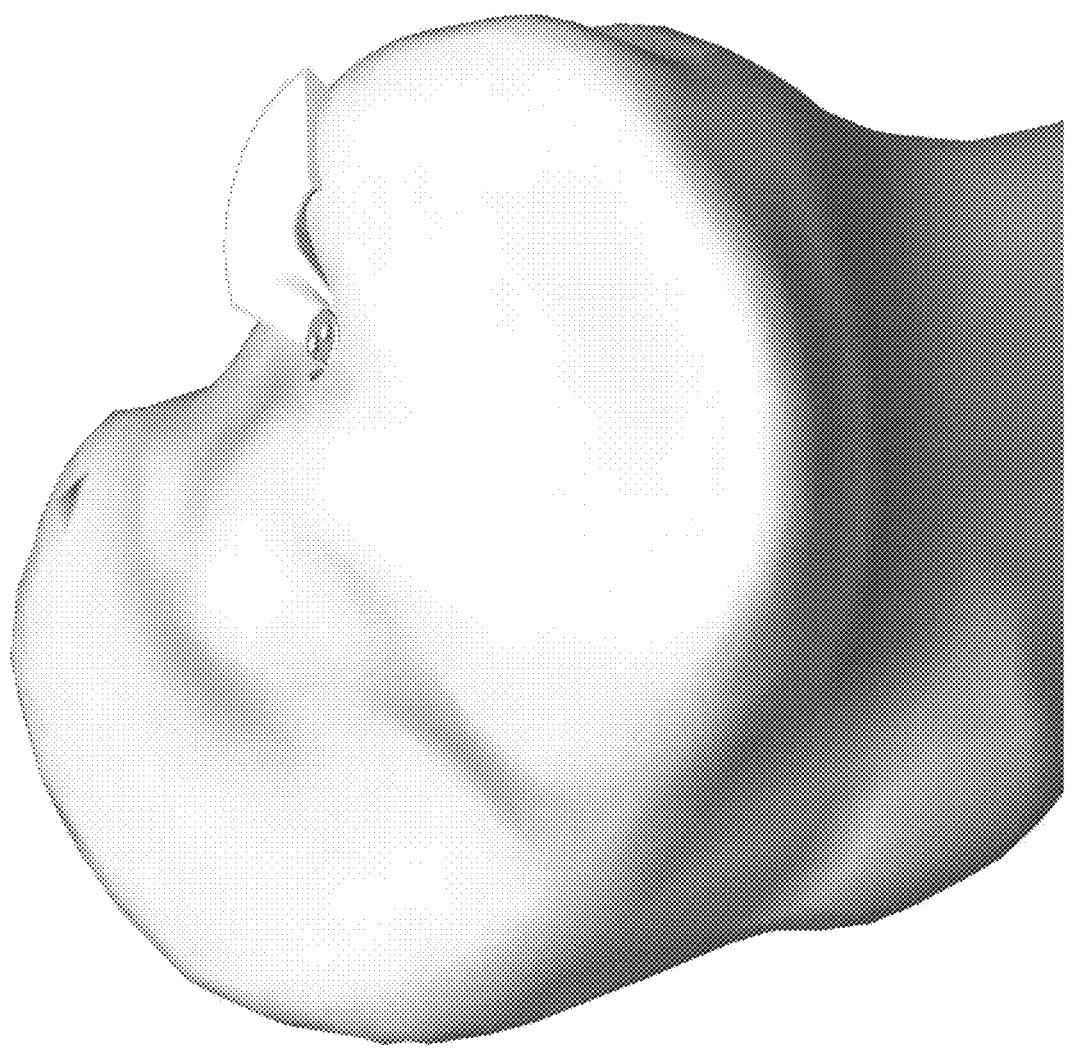
FIG. 78 depicts an exemplary suture anchor type implant as inserted in the posterior medial meniscal root of an exemplary knee according to an exemplary embodiment of the present invention.
Figure 79:
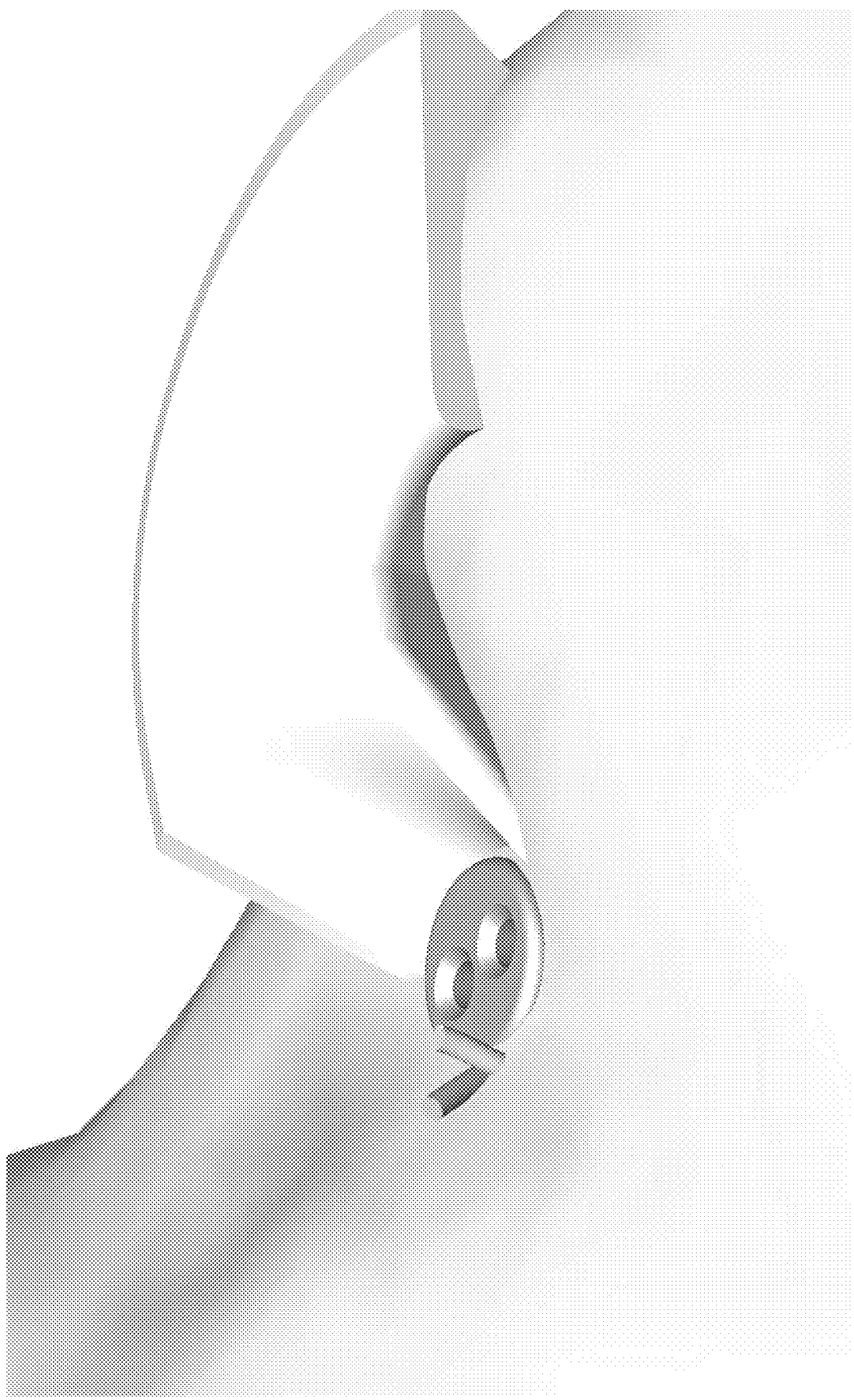
FIG. 79 depicts the exemplary suture anchor type implant of FIG. 78 in a magnified view.
Figure 80:
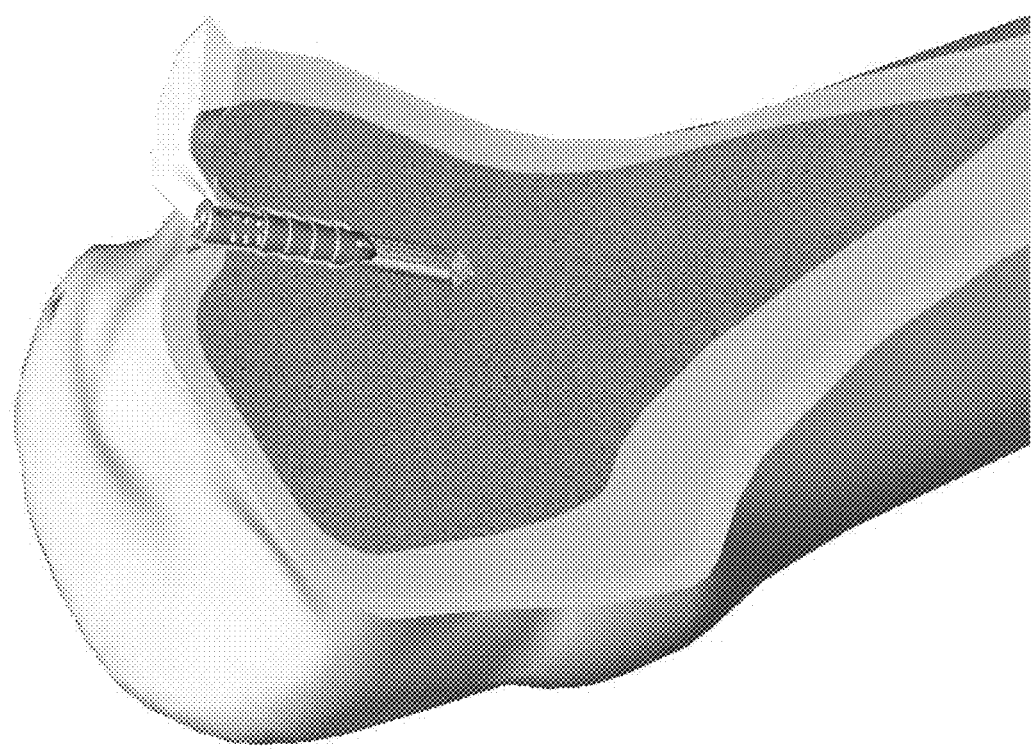
FIGS. 80, 81 and 82 depict the exemplary implant of FIGS. 78 and 79 in a vertical cut-away views, in various degrees of magnification and from different perspectives.
Figure 81:
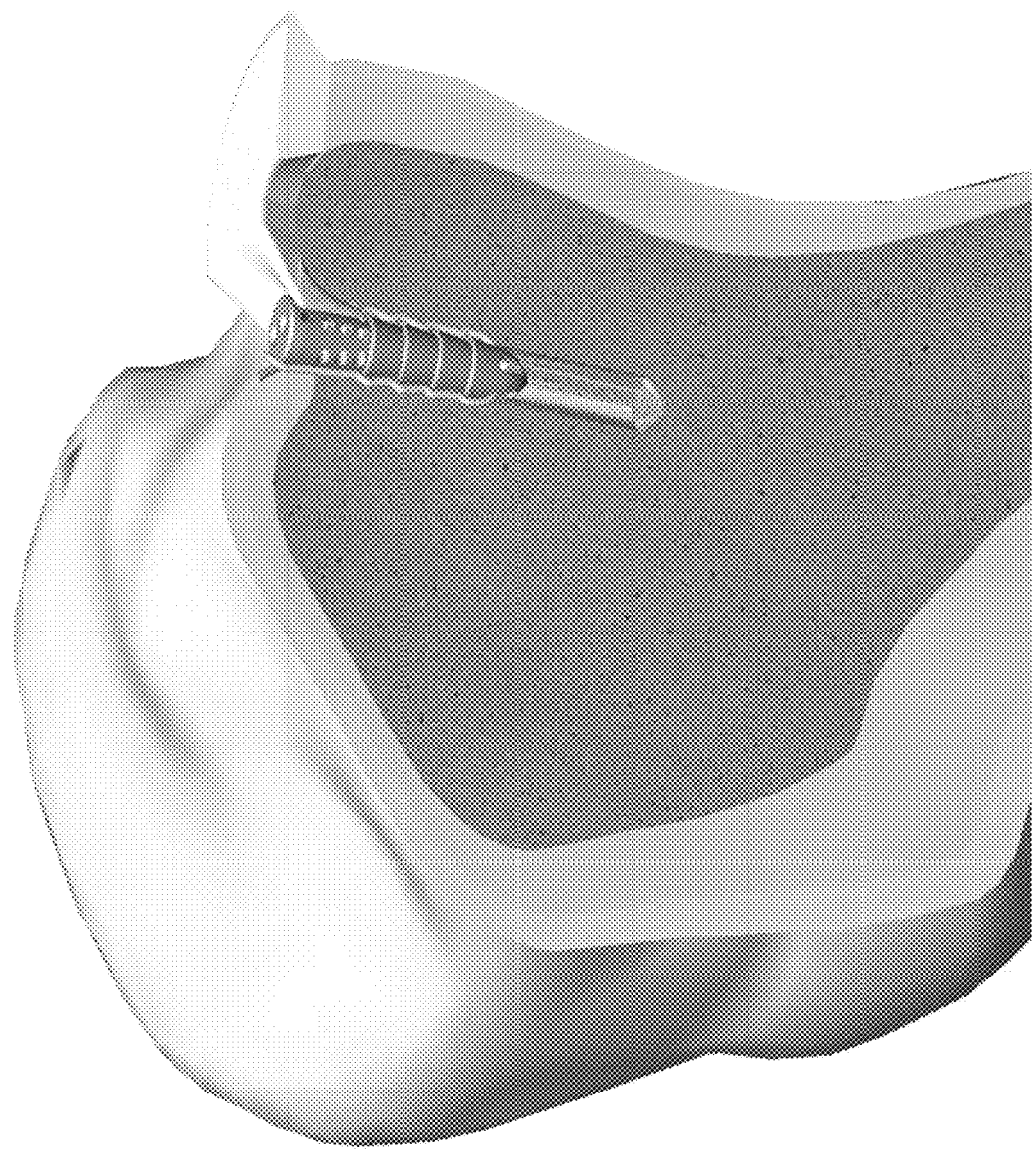
Figure 82:
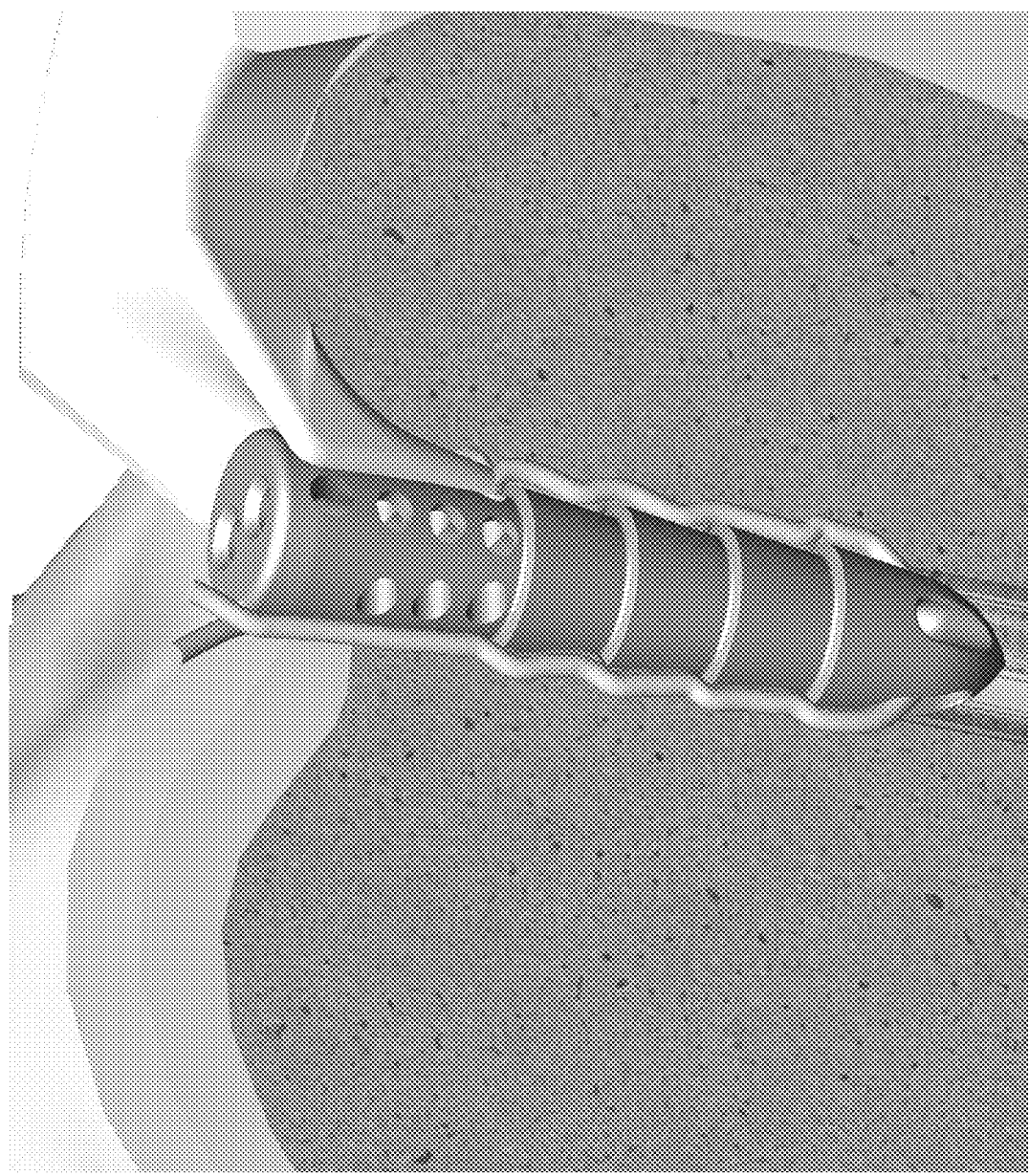
Figure 83:
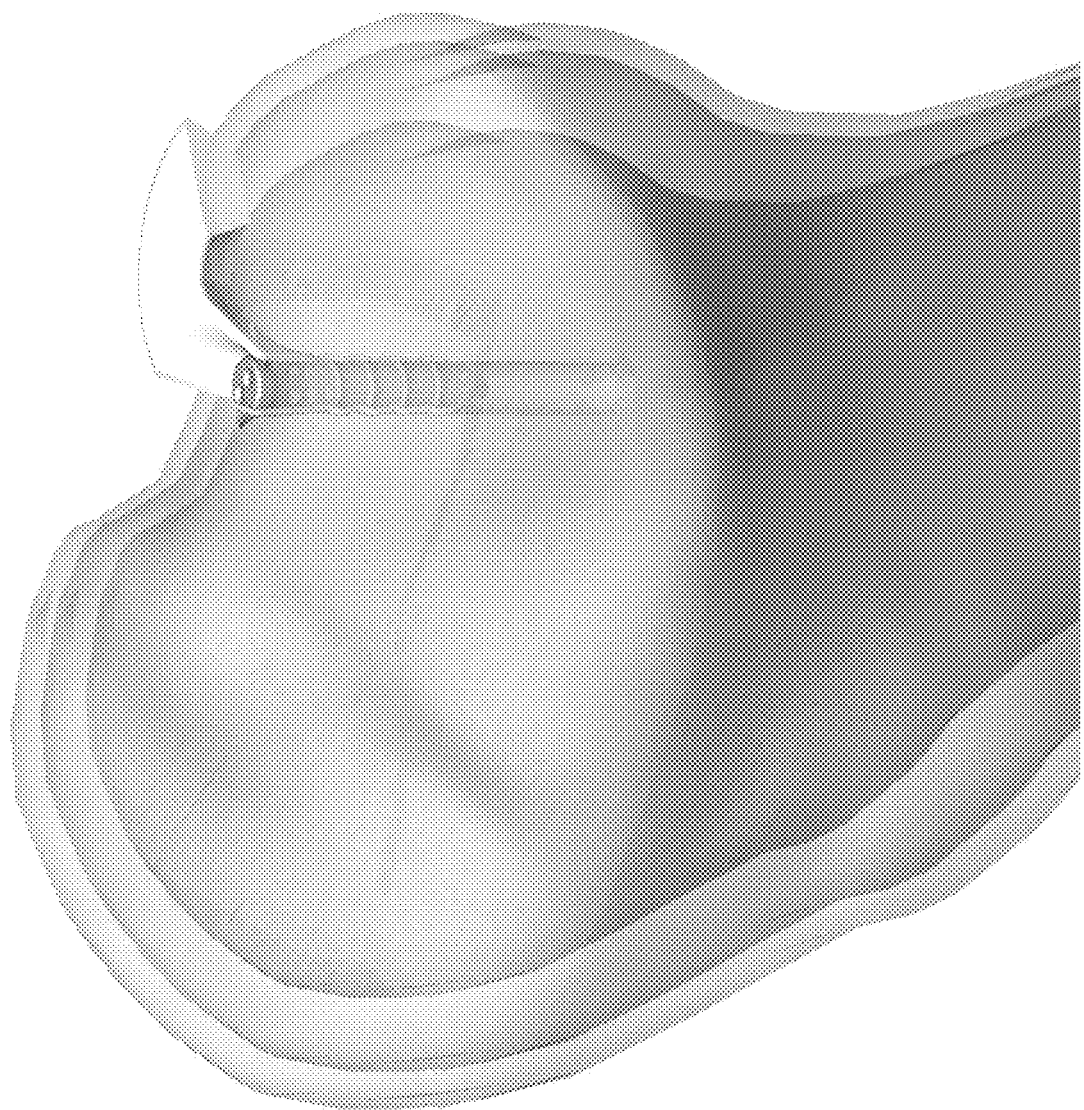
FIGS. 83, 84, 85 and 86 each depict the exemplary implant of FIGS. 78 and 79 in a transparent in situ view of a human knee, in various degrees of magnification.
Figure 84:
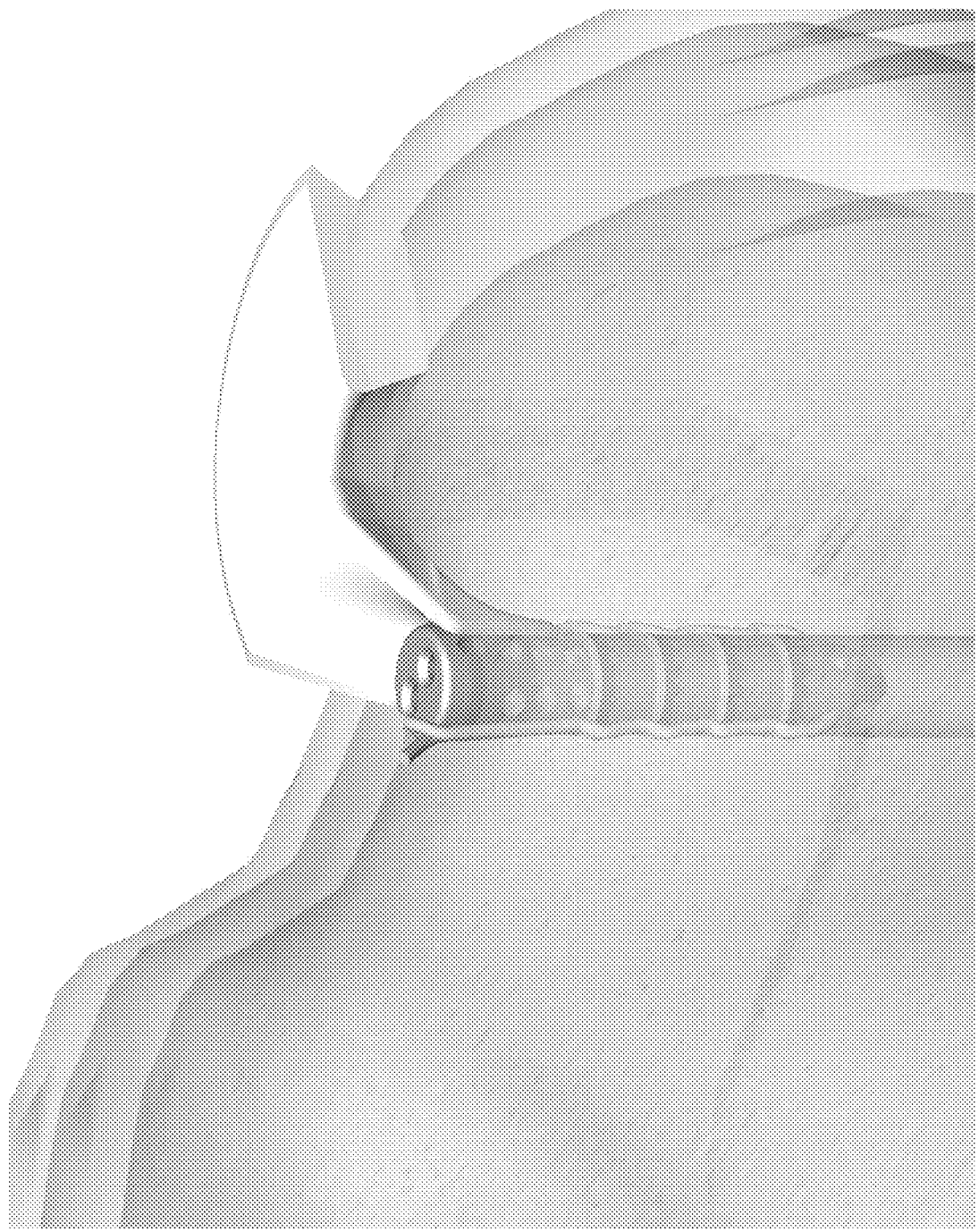
Figure 85:
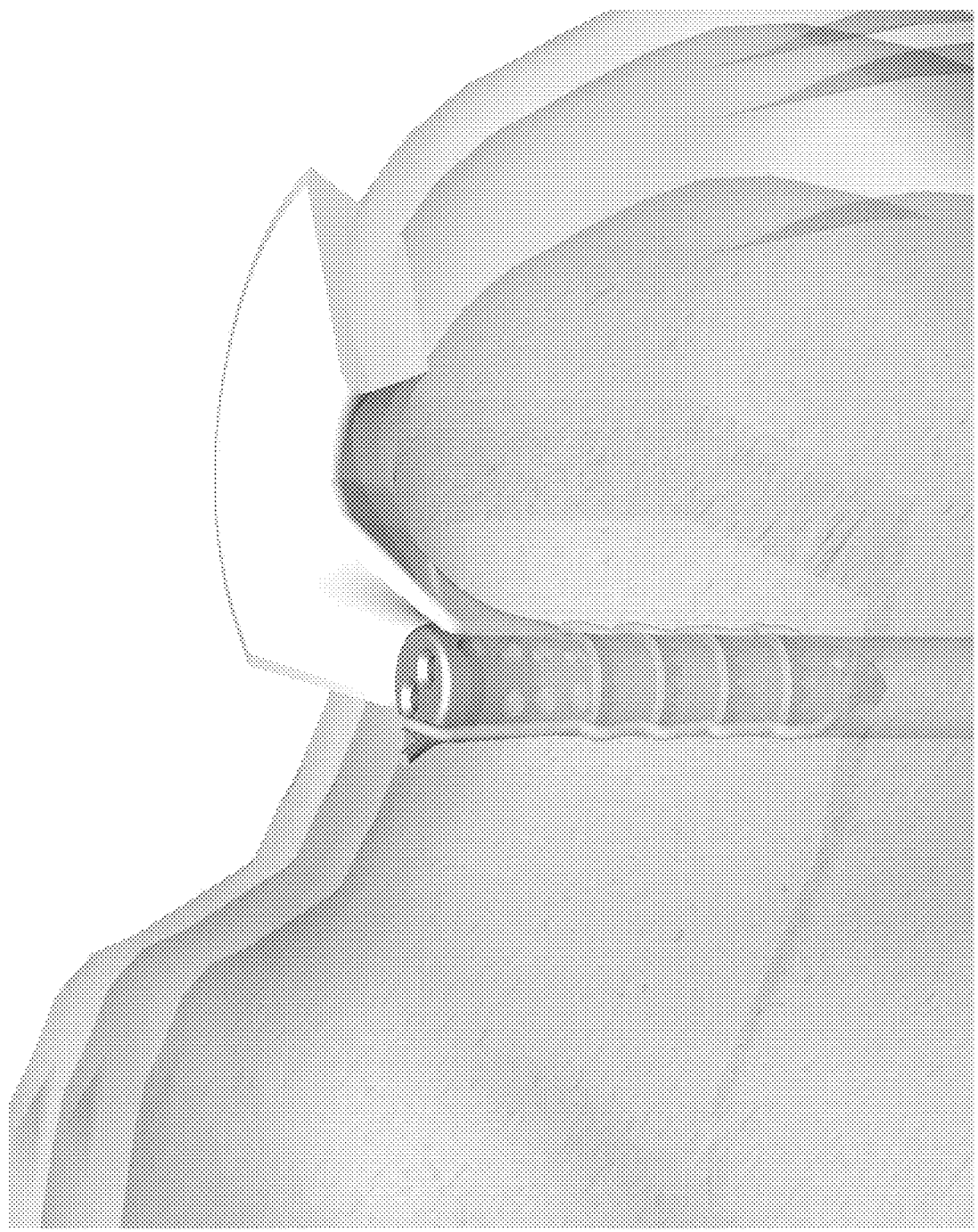
Figure 86:
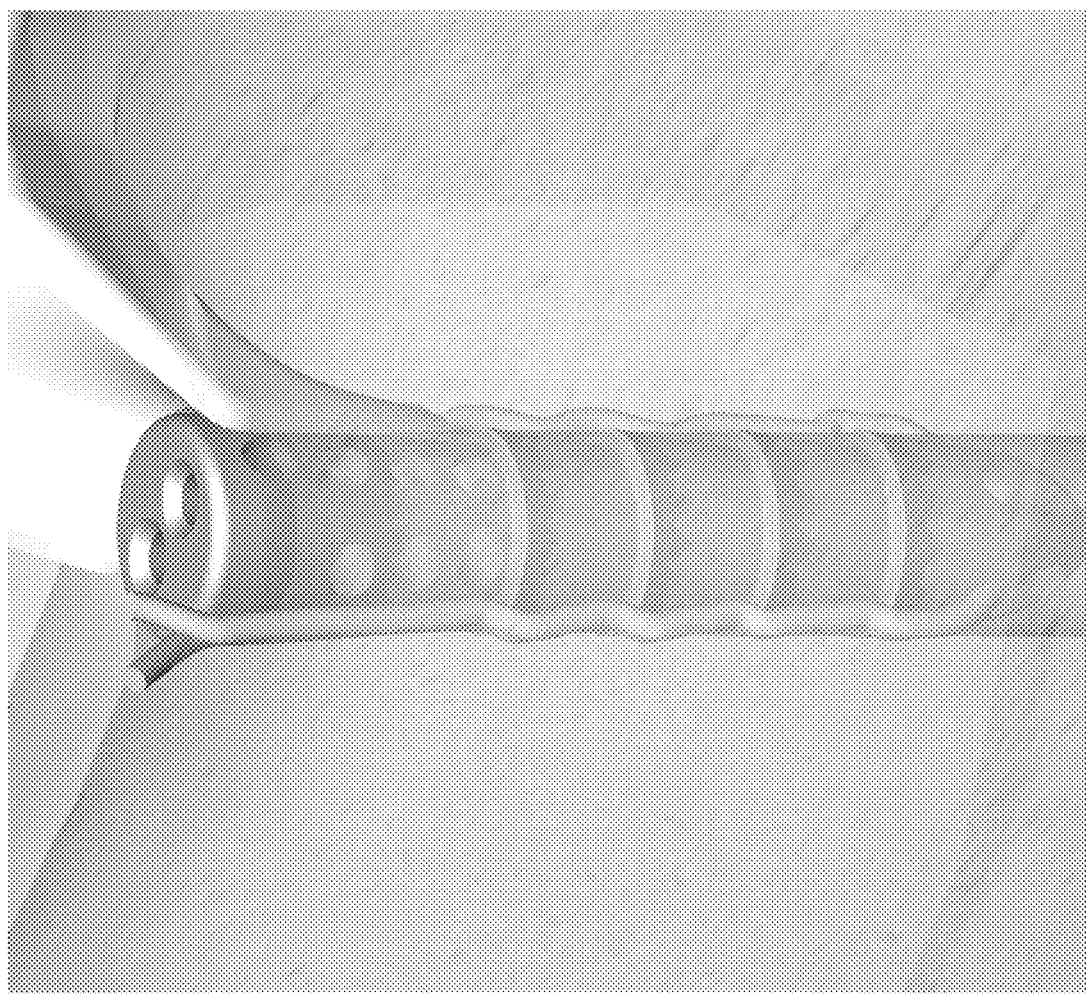

FIGS. 78-79 depict an exemplary suture anchor implant, of the type of one of Configurations A-E described above with reference to FIGS. 64-77, as inserted in an exemplary knee meniscus, in accordance with various embodiments. In this example, the implant is inserted into the posterior-medial meniscal root, as described above. As can be seen in FIGS. 78 and 79, the cap of the implant may be, for example, either flush or slightly below the surface of the surrounding tissue; therefore it will not interfere with the knee joint in any way. Also can be seen in FIG. 79, the stubs from the suture anchor will appear as shown once the device is finally implanted and secured in place, but prior to the suture leads being cut. It is thus noted that, in embodiments, when sing a suture anchor implant device, the suture is pulled into the drill hole with the meniscus. Once that is seen and confirmed to be stable, the suture may be cut down to be flush with the surface. Thus, the stubs shown in FIG. 79 would, once the surgeon confirms stability of the implant, be cut to be flush with the surface of the meniscus. Similarly, FIGS. 80-82 depict the exemplary implant of FIGS. 78 and 79 in longitudinally cut-away views, so that the example implant device may be seen as inserted into the bone. The depicted implant is, in this example, Configuration D. The proximal portion of the implant, as shown, is flush with the surrounding tissue. Alternatively, it may be slightly "sunk" below the surface. In this context it is noted that it is difficult to sink the implant too far down due to the limited room in the drill hole (unless the bone is soft and unhealthy). As may also be seen in these FIGS. 80-82, a user may first drill a hole in which to place the implant, and that hole is shown in the figure as extending slightly distally beyond the distal tip of the implant, generally, for example, by about 1 or 2 millimeters more. However, in other embodiments, it may be made just long enough to fit the implant, without the "headroom." Thus, in some embodiments, the hole need not be quite as deep as shown in FIGS. 81-82. It is also noted that for a meniscal root repair, for access, a posterior medial portal also needs to be made.

In FIG. 82 it is noted that a portion of the meniscus on the right side of the implant, as shown in the figure (white tissue on the right side f the example implant), has been pulled into the hole as the implant has been fully inserted. Also shown is the suture anchor tie protruding around the outside of the ribs of the example implant, and up through the top. In this configuration (Configuration D of FIGS. 64-77), as blood and nutrients enter the openings of the distal tip of the implant device, they proceed up through the internal canals and out the side emitters as well as the emitters on the top of the device, thereby providing nutrients to the portion of the meniscus that is pulled into the hole as well as to other portions of the meniscus nearby, so as to accomplish the desired functionality. Namely, to regenerate and heal the meniscus and thereby prevent any further complications, such as the onset of osteoarthritis.

It is here noted that It is preferred that in the insertion of any implant in accordance with various embodiments, that some of the meniscus, or other soft tissue structure that has been torn or damaged, or is suspected of being torn or damaged, be pulled down into the hole, or pulled down along the side of the implant, in the case that no hole is used (e.g., pre-drilled prior to insertion of an example implant), so that that portion of the soft tissue, as well as the portions it is connected to, are directly exposed to the blood flow out of the emitters. It is noted that this blood flow there in the hole, or there alongside the implant, to that portion of the meniscus or other soft tissue pulled down into the hole (whether drilled first, or created by the insertion of the implant) may be the most nutritive and most conducive to healing or rejuvenation. Obviously, for a tear, an implant according to various embodiments may obviate pain, as well as instability due to the tear. However, more importantly, it is believed by the inventor that arthritis, even without a root tear, likely includes microscopic damage to the blood flow and actual tissue structures. Thus, preemptively, or preventively, repairing a not torn meniscal root would likely rejuvenate it, and subsequently rejuvenate the entire meniscus. This may prevent the onset or progression of (knee) arthritis for any person that has the mild beginnings of arthritis, thus not only saving their tissues and joint, but obviating significant interventions, discomfort, and costs down the road.

Finally, FIGS. 83-86 show the same views as are present in FIGS. 80-82 except that here the implant device is shown inside an actual exemplary knee and the structures of the knee in front of the implant device are ghosted (made transparent) so that one may see precisely where the implant device sits in relation to the actual surrounding structures. It is again noted here that while the human knee has been described herein as a running example, the various implants and techniques described herein are equally applicable to various other tendons and cartilage structures, such as, for example, the rotator cuff of a shoulder joint and hips. It is thus understood that the example implant devices and methods are applicable at other surgical sites to attach other implant and tissues to bone. For example, the devices and methods may be used to attach sutures, tendons, ligaments, cables, implant anchor portions, and/or other objects to bone at surgical locations throughout a patient's body.

Implant Techniques and Procedures

A. Blade and Washer and Tack Type Implants

An exemplary implant technique is next described, which may apply to various embodiments of the "blade and washer" and "tack" type implants described above. In embodiments, a diagnostic knee arthroscopy may be first performed, as known in the art. A probe may then be used to confirm the diagnosis of a meniscal root tear, for example. It is noted that even in the case of a meniscal root revitalizing procedure, a root tear still needs to be ruled out. Next, it may be determined if one of the various angled drivers would allow repair through the standard medial portal. If that is not possible, then a Posterior Medial Portal may be created. As used herein, the term "Posterior Medial Portal" is understood to be posterior to the body of the meniscus but no further posterior to a line parallel to the meniscal root. The portal, in effect, is meant to be directly parallel to the meniscal root as it attaches to the bone (i.e., anterior to the anterior medial attachment of the posterior cruciate ligament and the shiny white fibers of the posterior horn of the medial meniscus).

In blade and washer embodiments, a soft tissue guide may allow safe entry of a delivery device, or "driver/handle" (with the anchor and washer attached). Such an exemplary guide may be made out of various types of plastic, as is known in the art. Alternatively, the entire instrument may be covered in a plastic sheath, thereby allowing it to be inserted easily into a joint (e.g., the knee), and upon, for example, pressing of a button by a user the sharp portions would emerge from the sheath, in similar fashion to extending an Exacto™ knife, for example. This would obviate the need for a separate soft tissue guide in such embodiments.

In the case of a torn meniscal root, in embodiments, the blade may pierce a portion of the meniscus and root (in a "shish kebab" manner) and be pressed against the root attachment on the bone. In embodiments, an exemplary driver/handle may be provided with a flat top at its proximal end, capable of being tapped with a mallet. The driver/handle may then be inserted into a joint, such as, for example, the knee joint, with the help of a soft tissue guide, as noted, or alternatively, as described above, ensheathed in a plastic covering. Then, for example, the flat top may be tapped with a mallet to drive the blade provided at the distal end of the driver/handle, approximately 2 cm into the bone.

Once the blade is anchored into the bone, the washer may be loosened from the driver/handle and, as noted above, a surgeon or other user grasping a slider handle, can push the washer down the shaft of the driver so that the washer rests against the bone, thereby sandwiching the meniscal root in between washer and the bone, for example. The washer may, for example, then be pushed over the proximal portion of the blade which is not inserted into the bone (i.e., the portion of the blade that remains in the meniscal root) for final placement. The final phase of this process is shown in FIGS. 10 and 11, described above. However, as noted above, in its final placement the top of the implant should preferably be either flush with the surrounding tissue or slightly "sunk" below it so as not to interfere with the cartilage. The figures above that describe the blade and washer embodiments, as well as for the integrated tack type implant embodiments, thus show the implants just before final placement in the flush or sunk position, so that the full top of the devices can readily be seen.

As regards the blade and washer embodiments, it is noted that, in embodiments, there may be connecting arms or structures between the proximal end of the driver and the slider handle, such that when a user taps on a flat top of the driver that force may be transferred to the slider handle, which may push the washer finally into place attached to the bone in similar fashion as the anchor was originally inserted into the bone.

Alternatively, for example, there may be side flat top surfaces, independently connected to the arms or structures that connect to the slide handle, and such side flat top surfaces may move independently of the central flat top, such that when malleting the washer into place by hitting these side flat top surfaces, no additional force is conveyed to the blade. It is noted that this mechanism is similar to that used in the known Arthrex™ Push-Lock system, for example. In either case, the washer may thereby be pushed into final position, surrounding the blade, and with a distal portion fixed into the bone, as shown in magnified detail in FIGS. 10 and 11. Thus, in its full extension, the sharp irrigation spikes (or blades) of the washer may also be punched into the bone. Once the washer is so affixed, the driver may then be removed and a probe used to confirm stable fixation.

It is noted that in some embodiments, multiple implants may be used, if large portions of the meniscal root are seen as needing revascularization, or, for example, there are multiple weak areas spaced apart from one another.

For ease of illustration, exemplary embodiments of the blade and washer, as well as the tack type implant (which is an integrated into one piece version of a blade and washer type implant) have been shown and described with a cylindrical blade or shaft, as the case may be. It is understood that the cross section of the blade or shaft need not be circular, and thus, in the blade and washer type implant, the central bore of the washer also need not be circular. Moreover, in the blade and washer type implant, while generally the washer may be radially symmetric, so as not to require a specific rotational direction at implant, in some embodiments, where there is a directional weakening of the meniscus, a radially asymmetric cross sectional shape of the washer may be used. Finally, in embodiments, one blade may be used with multiple shapes and sizes of washers.

Because the various embodiments of implant devices presented herein may be 3D printed as needed, and not mass produced, various modifications and optimizations on a per patient, and per joint basis may be made. Thus, shape, size, cross sectional blade or shaft, as well as microtube count may all be easily customizable in a personalized medicine implementation. Alternatively, various standard sizes may be manufactured, and pre-produced in advance, in a more standard production model.

As regards the tack type implant, it is noted that after a posterior-medial portal is made the blade may be inserted and placed over the torn (or, in the case that the procedure is performed preventively, weakened or vulnerable) meniscal root tissue. The tack implant may then be slid down, and in a "shish-kabob" fashion, the sharp tip of the tack implant (which has now pierced through the patient's tissue) may then be placed at the meniscus root attachment site and punched in with a mallet until the head is flush with the articular surface of the tibia.

B. Suture Anchor Type Implant Technique

An exemplary implant technique is next described, which applies to various exemplary embodiments of the "suture anchor" type implants described above.

An initial diagnostic arthroscopy can be performed utilizing standard portals. The meniscal root tear may be confirmed visually, and also confirmed with a probe. Next, a posterior-medial portal is made for best access for fixation. A plastic cannula may be placed in the portal to allow passage of the instrumentation. Next, a drill guide is inserted and placed at the meniscal root attachment. A drill hole is then made to a depth of slightly deeper than the length of an actual suture anchor, for example 18 mm. Next, an arthroscopic suture passer can be used to pass a suture through the torn meniscal root (or, if the procedure is done preventively, through the meniscal root at the site decided to be weakened, and in jeopardy of tearing) in a mattress fashion. The suture may then be passed through the eyelet of the anchor. While tension is held on the sutures, the anchor may be passed through the cannula with the adapter, and then in to the drill hole. The anchor may then be punched into place using a mallet. The meniscus should be pulled into the drill hole along with the suture (while still being held taught). A probe may then be used to confirm good fixation, and if confirmed, then a suture cutter may be used to cut the suture. If additional fixation is needed for a given meniscal tear (or preventively, for the portion of the meniscus that is vulnerable), then a second anchor implant device may be used. It is here noted that this illustrates one of the advantages of the exemplary suture anchor embodiment of FIGS. 64-77, in that by having the overall diameter more or less the same along the entire length of the device (as opposed to the tack type implant described above), it is small enough to allow for multiple anchor type implants to be used in a given patient, in close proximity to one another, without having to clear a safe distance between edges of the "distributor cap" structure at the top of the tack device.

As regards which suture to use, it is noted that multiple types may be utilized. For example, Arthrex™ Fiberwire™ may be used. Alternatively, there is an Arthrex™ suture tape that can be used, and in general an Ethibond™ suture is also recommended.

Diagnostic Guidelines for Preventing Onset of Osteoarthritis

As noted above, implanting an exemplary implant device may be done prophylactically, in absence of any actual meniscal tear, once evidence of early onset of osteoarthritis is seen. To illustrate such indicia, FIGS. 87 and 88 contain charts showing progression or stage of osteoarthritis based, respectively, on X-ray and MRI findings.

Figure 87:
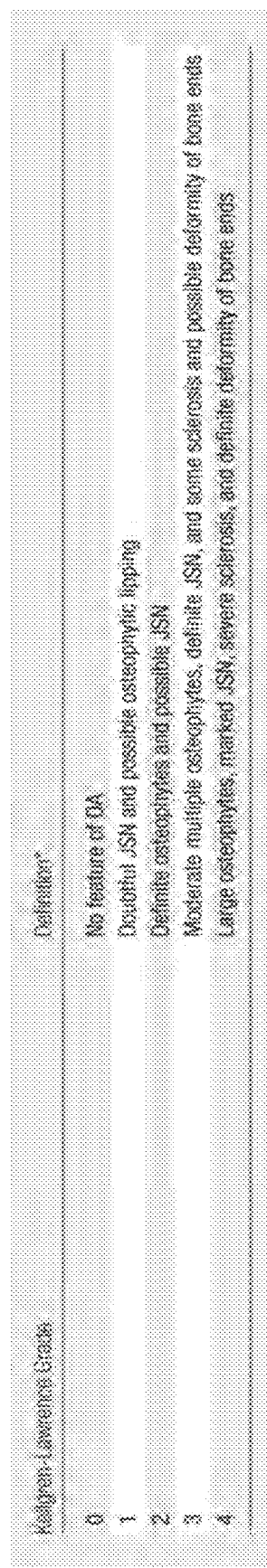
FIG. 87 is a chart showing the Kellgren-Lawrence diagnostic scale for osteoarthritis.

FIG. 87 presents the K-L grading system and is based on X-ray. The greater the number, the greater degree of disease. In FIG. 88, "JSN" refers to "joint space narrowing." For the purpose of the replenishing procedure described herein, patients at Grades 1 and 2 would be ideal. Patients at Grade 3 would be borderline, and for those at Grade 4, it may simply be too late to help.

FIG. 88 is a chart listing the MRI characteristics of OA. It is noted, however, that X-ray has a more definitive grading system. Therefore, with reference to FIG. 87, one may say that an indication for the replenishing procedure is K-L grades 1 or 2. Grade 3 is a borderline indication (depending upon the surgeon's discretion). However, in embodiments, these indications may be complimented by MRI when the K-L grade is questionable. For example, when the K-L grade is 0 but the MRI findings have 1 or more of the MRI criteria, then that would be an indication for an insertion of an implant (using one of the various exemplary embodiments described above) to rejuvenate the meniscus, in embodiments. On the other side of the spectrum, if the K-L grade is a 3 (as noted, a borderline condition), and MRI findings can be used to compliment the X-ray findings and make a judgement that either the disease is not yet severe enough, or it might be too far advanced, these findings may, for example, drive the decision as to whether to proceed or not, in such a borderline case.

Some of the foregoing examples have illustrated various embodiments of devices and methods useful to attach soft tissue to a bone by forming a tunnel through the bone, passing the strand through the bone, and then capturing both ends of the strand with a single implant. While various embodiments have been illustrated for repair of a human meniscus, they are equally applicable to various other tendons and cartilage structures, such as rotator cuff of a shoulder joint and hips. It is thus understood that the devices and methods according to various embodiments are applicable at other surgical sites to attach other implant and tissues to bone. For example, devices and methods according to various embodiments may be used to attach sutures, tendons, ligaments, cables, implant anchor portions, and/or other objects to bone at surgical locations throughout a patient's body.

In the illustrative examples, implants have been shown securing suture portions at various locations of the blade or shaft of the implant. For example, some of the examples have described or depicted fixation at a proximal portion of the blade or shaft, and/or at a distal portion of the blade or shaft. The proximal and distal portions of the blade or shaft may refer to distinct proximal and distal ends of the blade or shaft. The proximal and distal portions may refer to relative regions of the blade or shaft, such as a proximal one half and a distal one half, or, for example, a proximal one third and a distal two thirds, or still alternatively, a proximal two thirds and a distal one third of the blade or shaft of the implant device, or some other fractional part referring to distinct relative zones.

The different illustrative examples have been shown with various forms of bone fixation including threads and annular ridges of varying size and shape. These different forms of fixation may be interchanged within the scope of the invention. For example, where ridges are shown, threads may be often be substituted and where threads are shown, ridges may often be substituted, as long as the irrigation network internal to the implant device is preserved. Other forms of fixation as may be known in the art may also be substituted.

It will also be appreciated that one or more of the elements depicted in the drawings can also be implemented in a more separated or integrated manner, or even removed or rendered as inoperable in certain cases, as is useful in accordance with a particular application.

As used in the description herein and throughout any claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Although various implant devices and insertion methods and techniques have been described herein, the scope of coverage of this patent is not limited thereto. To the contrary, this patent is understood to cover all devices, methods, systems, kits and articles of manufacture fairly falling within the scope of the appended claims.

REFERENCES

1. Englund M., *The role of biomechanics in the initiation and progression of OA of the knee*. Best Pract Res Clin Rheumtol. 2010; 24 (I):3946
2. Pauli C, Grogan S P, Patil S, Otsuki S, Hasegawa A, Koziol J, et al., *Macroscopic and histopathologic analysis of human knee menisci and aging and osteoarthritis*. Osteoarthritis Cartilage. 2011; 19 (9):113441
3. Hunter D J, Zhang Y Q, et al. *The association of meniscal pathologic changes with cartilage loss in symptomatic knee osteoarthritis*. Arthritis Rheum. 2006; 54(3): 795801.
4. Papalia R, Vasta S, et al. *Meniscal root tears: from basic science to ultimate surgery*. Br. Med Bull. 2013; 106: 91115
5. Bhattacharyya T, Gale D, et al. *The clinical importance of meniscal tears demonstrated by magnetic resonance imaging in osteoarthritis of the knee*. J. Bone Joint Surgery AM 2003; 85A (l):49
6. Ding C, Martel Pelletier J, et al., *Meniscal tear as an osteoarthritis risk factor in a largely non-osteoarthritic cohort: a cross sectional study*. J Rheumatol. 2007; 34 (4):77684.
7. Moseley J B, O'Malley K, Petersen N J, et al., *A controlled trial of arthroscopic surgery for osteoarthritis of the knee*. N Engl J Med 2002; 347(2):818.
8. Kirkley A, Birmingham T B, Litchfield R B, et al., *A randomized trial of arthroscopic surgery for osteoarthritis of the knee*. N Engl J Med 2008; 359:1097107.
9. Herrlin S, Hallander M, Wange P, Weidenhielm L, Werner S., *Arthroscopic or conservative treatment of degenerative medial meniscal tears: a prospective randomised trial*.
Knee Surg Sports Traumatol Arthrosc 2007; 15(4):393-401. PM: 17216272.
10. *Biomechanical Consequences of a Tear of the Posterior Root of the Medial Meniscus* Surgical Technique Christopher D. Harner, MD; Craig S. Mauro, MD; Bryson P. Lesniak, MD; James R. Romanowski, MD J Bone Joint Surg Am, 2009 Oct. 1; 91 (Supplement 2): 257 270 http://dx.doi.Org/10.2106/JBJS.I.00500
11. *Meniscal Root Tears: Significance, Diagnosis, and Treatment*.
Sanjeev Bhatia
Christopher M LaPrade
Michael B Eilman
Robert F LaPrade
The American Journal of Sports Medicine (Impact Factor: 4.7). 03/2014; DOI: 10.1177/0363546514524162
Source: PubMed
12. The American Journal of Sports Medicine http://ajs.sagepub.com/*Biomechanical Evaluation of the Transtibial Pull Out Technique for Posterior Medial Meniscal Root Repairs Using* 1 *and* 2 *Transtibial Bone Tunnels*, Christopher M. LaPrade, Matthew D. LaPrade, Travis Lee Turnbull, Coen A. Wijdicks, and Robert F. LaPrade
Am J Sports Med published online Jan. 8, 2015,
DOI: 10.1177/0363546514563278

What is claimed is:

1. A joint implant device, comprising:
   a cylindrical anchor with a central longitudinal axis, the cylindrical anchor including:
   a distal portion that comes to a point, the distal portion configured to be inserted into cancellous bone adjacent to a joint;
   a proximal portion with a flat top end, the proximal portion comprising a top portion of the cylindrical anchor, at least a portion of the proximal portion configured to abut a meniscus or soft tissue of the joint and to allow access into a joint space of the joint, said portion of the proximal portion including a plurality of outflow tubes that respectively connect to a predetermined pattern of openings in an outer side surface of the proximal portion ("side openings"); and
   a medial portion, provided between the distal portion and the proximal portion, the medial portion having no openings provided in its outer surface,
   wherein the anchor is provided with at least two internal microtubes, each having an intake in the distal portion, and each extending longitudinally through the medial portion and into the proximal portion along an axis substantially parallel to the central longitudinal axis, and each fluidly connected to one of the outflow tubes of the proximal portion, wherein an internal diameter of the outflow tubes is less than or equal to an internal diameter of the internal microtubes, and an internal diameter of the side openings is less than or equal to the internal diameter of the outflow tubes,
   and wherein the internal microtubes, the side openings, and their respective sizes are together configured to utilize the natural pressure gradient that allows blood to flow in the joint to convey blood and nutrients from the cancellous bone to the meniscus or soft tissue.

2. The joint implant device of claim 1, wherein the at least two internal microtubes comprise a plurality of internal microtubes.

3. The joint implant device of claim 1, further comprising: an eyelet provided in the distal portion through which a suture may be provided for additional fixation into the soft tissue.

4. The joint implant device of claim 3, wherein the eyelet is provided at or near the point of the distal portion.

5. The joint implant device of claim 4, further comprising at least two protruding ribs provided on the distal portion, or provided on the distal and medial portions, above the eyelet.

6. The joint implant device of claim 1, further comprising receiving holes provided in a top surface of the flat top end, arranged to receive corresponding prongs of a delivery device.

7. The joint implant device of claim 1, wherein each of the microtubes has an inner diameter greater than or equal to 0.33 mm.

8. The implant device of claim 1, wherein the predetermined pattern of openings comprises multiple columns of openings, the columns provided at regular angular intervals along the outer surface of the proximal portion.

9. The joint implant device of claim 1, wherein each of the microtubes has an inner diameter greater than or equal to 1.0 mm, and each of the outflow tubes an inner diameter greater than 0.8 mm.

10. A kit for use in procedures to cure meniscal root tears, prevent meniscal tears, or perform soft tissue repair, comprising:
the joint implant device of claim 1; and
a delivery device provided with a handle on a proximal end thereof, a distal end of the delivery device releasably attached to the proximal end of the joint implant.

11. The kit of claim 10, wherein the handle of the delivery device comprises a surface configured to be tapped by a hammer or mallet.

12. The kit of claim 10, further comprising a soft tissue guide.

13. The kit of claim 10, wherein the cylindrical anchor further comprises at least two protruding ribs on its distal portion.

14. The kit of claim 10, wherein each of the set of microtubes of the joint implant device has an inner diameter greater than or equal to 0.33 mm.

15. The kit of claim 10, wherein at least one of:
the predetermined pattern of openings comprises multiple columns of openings, the columns provided at regular angular intervals along the outer surface of the proximal portion; or
each of the microtubes of the cylindrical anchor has an inner diameter greater than or equal to 1.0 mm, and each of the outflow tubes an inner diameter greater than 0.8 mm.

16. A joint implant device, comprising:
a cylindrical anchor with a central longitudinal axis, the cylindrical anchor having a total length, the cylindrical anchor including:
a distal portion that comes to a point, the distal portion configured to be inserted into cancellous bone adjacent to a joint;
a proximal portion with a flat top end, the proximal portion comprising a top portion of the cylindrical anchor, the proximal portion having a length not greater than 40% of the total length, at least a portion of the proximal portion configured to abut a meniscus or soft tissue of the joint and allow access into a joint space of the joint, said portion of the proximal portion that is configured to abut the meniscus or soft tissue of the joint including a plurality of outflow tubes that connect to a plurality of openings in an outer side surface of the proximal portion; and
a medial portion having a distal end and a proximal end, the medial portion connected to the distal portion at its distal end and the proximal portion at its proximal end, the medial portion including fastening features and having no openings provided in its outer surface,
wherein the anchor is provided with at least two internal microtubes, each having an intake in the distal portion, and each extending longitudinally through the medial portion and into the proximal portion along an axis substantially parallel to the central longitudinal axis, and each fluidly connected to one or more of the outflow tubes, wherein an internal diameter of the outflow tubes is less than or equal to an internal diameter of the internal microtubes, and an internal diameter of the side openings is less than or equal to the internal diameter of the outflow tubes, and
wherein the plurality of outflow tubes and the plurality of outer side surface openings are collectively configured, as to number, placement and size, to together convey blood and nutrients from the cancellous bone to the meniscus or soft tissue, under a natural dynamic pressure gradient between the cancellous bone and the meniscus or soft tissue of the joint, from the intake in the distal portion to one of the outer side surface openings of the proximal portion.

17. The joint implant device of claim 16, further comprising: an eyelet provided in the distal portion through which a suture may be provided for additional fixation into the soft tissue.

18. The implant device of claim 16, wherein the proximal portion has a length not greater than 33% of the total length.

19. The joint implant device of claim 16, wherein at least one of:
each of the microtubes has an inner diameter greater than or equal to 1.0 mm, and each of the outflow tubes an inner diameter greater than 0.8 mm, but less than 1.0 mm.

* * * * *